US012005140B2

(12) United States Patent
Boyer et al.

(10) Patent No.: US 12,005,140 B2
(45) Date of Patent: Jun. 11, 2024

(54) PHARMACEUTICAL FORMULATION

(71) Applicant: Klaria Pharma Holding AB, Uppsala (SE)

(72) Inventors: Scott Boyer, Uppsala (SE); Shengzhen Cai, Uppsala (SE); Fredrik Hübinette, Uppsala (SE); Leif Ingemarsson, Uppsala (SE)

(73) Assignee: Klaria Pharma Holding AB, Uppsala (SE)

( * ) Notice: Subject to any disclaimer, the term of this patent is extended or adjusted under 35 U.S.C. 154(b) by 0 days.

(21) Appl. No.: 17/054,945

(22) PCT Filed: May 23, 2019

(86) PCT No.: PCT/EP2019/063376
§ 371 (c)(1),
(2) Date: Nov. 12, 2020

(87) PCT Pub. No.: WO2019/224323
PCT Pub. Date: Nov. 28, 2019

(65) Prior Publication Data
US 2021/0369601 A1    Dec. 2, 2021

(30) Foreign Application Priority Data

May 23, 2018   (GB) ...................................... 1808462

(51) Int. Cl.
| | | |
|---|---|---|
| A61K 9/00 | (2006.01) | |
| A61K 31/137 | (2006.01) | |
| A61K 47/02 | (2006.01) | |
| A61K 47/18 | (2017.01) | |
| A61K 47/20 | (2006.01) | |
| A61K 47/22 | (2006.01) | |
| A61K 47/26 | (2006.01) | |
| A61K 47/36 | (2006.01) | |

(52) U.S. Cl.
CPC ............ *A61K 9/006* (2013.01); *A61K 31/137* (2013.01); *A61K 47/02* (2013.01); *A61K 47/183* (2013.01); *A61K 47/20* (2013.01); *A61K 47/22* (2013.01); *A61K 47/26* (2013.01); *A61K 47/36* (2013.01)

(58) Field of Classification Search
CPC ...... A61K 9/006; A61K 31/137; A61K 47/02; A61K 47/183; A61K 47/20; A61K 47/22; A61K 47/26; A61K 47/36
See application file for complete search history.

(56) References Cited

U.S. PATENT DOCUMENTS

| | | |
|---|---|---|
| 5,288,497 A | 2/1994 | Stanley et al. |
| 5,288,498 A | 2/1994 | Stanley et al. |
| 5,785,989 A | 7/1998 | Stanley et al. |
| 8,759,282 B2 | 6/2014 | Stenberg et al. |
| 9,192,570 B2 | 11/2015 | Wyse et al. |
| 9,833,461 B2 | 12/2017 | Modi |
| 10,039,710 B2 | 8/2018 | Potta et al. |
| 11,007,144 B2 | 5/2021 | Boyer et al. |
| 11,219,600 B2 | 1/2022 | Boyer et al. |
| 2004/0247649 A1 | 12/2004 | Pearce et al. |
| 2005/0031675 A1 | 2/2005 | Spence Leung et al. |
| 2006/0039959 A1 | 2/2006 | Wessling |
| 2006/0110331 A1 | 5/2006 | Dang et al. |
| 2008/0269347 A1 | 10/2008 | Bruss et al. |
| 2009/0186107 A1 | 7/2009 | Haber et al. |
| 2009/0221489 A1 | 9/2009 | Stenberg et al. |
| 2009/0246273 A1 | 10/2009 | Al-Ghanaeem |
| 2010/0112050 A1 | 5/2010 | Ryoo et al. |
| 2011/0033542 A1 | 2/2011 | Myers et al. |
| 2014/0005218 A1 | 1/2014 | Myers et al. |
| 2014/0178473 A1* | 6/2014 | Lim ........................ A61P 25/20 514/289 |
| 2014/0256823 A1 | 9/2014 | McCarty |
| 2014/0271788 A1 | 9/2014 | Myers et al. |
| 2015/0005356 A1 | 1/2015 | Fleming |
| 2015/0224070 A1 | 8/2015 | Boudy et al. |
| 2015/0297653 A1 | 10/2015 | Speier |

(Continued)

FOREIGN PATENT DOCUMENTS

| | | |
|---|---|---|
| CA | 2487882 A1 | 12/2003 |
| CN | 101081218 | 12/2007 |

(Continued)

OTHER PUBLICATIONS

Stepensky et al. Long-term stability study of L-adrenaline injections: Kinetics of sulfonation and racemization pathways of drug degradation. Journal of Pharmaceutical Sciences 2004, 93(4):969-980 (Year: 2004).*

Abd El Azim, H., et al., "Liposomal buccal mucuadhesive film for improved delivery and permeation of water-soluble vitamins", International Journal of Pharmaceutics, 2015, 488(1): 78-85.

Abdelkader et al., "Novel in situ gelling ocular films for the opioid growth factor-receptor antagonist-naltrexone hydrochloride: Fabrication, mechanical properties, mucoadhesion, tolerability and stability studies", *Int J Pharmaceutics*, 2014, 477(1-2), 631-642.

(Continued)

*Primary Examiner* — Robert A Wax
*Assistant Examiner* — Olga V. Tcherkasskaya
(74) *Attorney, Agent, or Firm* — Hamilton, Brook, Smith & Reynolds, P.C.

(57) ABSTRACT

The present invention relates to a film comprising an alginate salt of a monovalent cation or a mixture of alginate salts containing at least one alginate salt of a monovalent cation, and a compound of Formula (I), such as adrenaline, or a pharmaceutically acceptable salt thereof. The present invention further relates to methods for manufacturing such a film, and the use of such a film in the treatment of a human patient, in particular the use of such a film in the treatment of a condition selected from anaphylaxis, superficial bleeding and cardiac arrest.

26 Claims, 12 Drawing Sheets

(56) References Cited

U.S. PATENT DOCUMENTS

| | | |
|---|---|---|
| 2016/0051510 A1 | 2/2016 | Allen |
| 2016/0206627 A1 | 7/2016 | Gosselin et al. |
| 2017/0079907 A1 | 3/2017 | Potta et al. |
| 2017/0165315 A1 | 6/2017 | Karavas et al. |
| 2017/0290776 A1 | 10/2017 | Schobel et al. |
| 2017/0290870 A1 | 10/2017 | Schaneville |
| 2017/0348251 A1 | 12/2017 | Schobel et al. |
| 2018/0104195 A1* | 4/2018 | Schobel .............. A61K 31/137 |
| 2018/0117019 A1 | 5/2018 | Wang et al. |
| 2018/0125977 A1 | 5/2018 | Schobel et al. |
| 2020/0054550 A1 | 2/2020 | Boyer et al. |
| 2020/0246253 A1 | 8/2020 | Boyer et al. |
| 2021/0283047 A1 | 9/2021 | Boyer et al. |
| 2021/0346277 A1 | 11/2021 | Boyer et al. |
| 2022/0160618 A1 | 5/2022 | Boyer et al. |
| 2022/0273584 A1 | 9/2022 | Boyer et al. |
| 2022/0280453 A1 | 9/2022 | Boyer et al. |
| 2023/0018732 A1 | 1/2023 | Boyer et al. |

FOREIGN PATENT DOCUMENTS

| | | | |
|---|---|---|---|
| CN | 101574330 | 11/2009 | |
| CN | 102871984 | 1/2013 | |
| CN | 102961365 | 3/2013 | |
| CN | 105878171 A | 8/2016 | |
| CN | 107080745 | 8/2017 | |
| EP | 1897543 A1 | 3/2008 | |
| EP | 2431028 A2 | 3/2012 | |
| EP | 1976562 B1 | 2/2018 | |
| GB | 933462 | 8/1963 | |
| IN | 351KOL2006 | 4/2006 | |
| KR | 20080023873 | 3/2008 | |
| KR | 20140110778 | 9/2017 | |
| WO | 91/03236 A1 | 3/1991 | |
| WO | 98/01134 A1 | 1/1998 | |
| WO | 98/02182 A1 | 1/1998 | |
| WO | 01/87276 A1 | 11/2001 | |
| WO | WO 2003/101357 A1 | 5/2003 | |
| WO | WO 2004/012720 A1 | 2/2004 | |
| WO | 2004/045305 A2 | 6/2004 | |
| WO | 2004/075877 A1 | 9/2004 | |
| WO | 2005/004989 A2 | 1/2005 | |
| WO | WO 2005/018323 A1 | 3/2005 | |
| WO | WO 2005/048980 A1 | 6/2005 | |
| WO | 2006/023796 A2 | 3/2006 | |
| WO | WO 2006/095267 | 9/2006 | |
| WO | WO 2006/096913 A1 | 9/2006 | |
| WO | 2007/028247 A1 | 3/2007 | |
| WO | 2007/049102 A1 | 5/2007 | |
| WO | WO 2007/073346 A1 | 6/2007 | |
| WO | WO 2007/125533 A2 | 11/2007 | |
| WO | 2007/143674 A2 | 12/2007 | |
| WO | 2008/034881 A1 | 3/2008 | |
| WO | WO 2008/073918 A1 | 6/2008 | |
| WO | 2008/095144 A2 | 8/2008 | |
| WO | WO 2008/098195 A2 | 8/2008 | |
| WO | 2009/126132 A1 | 10/2009 | |
| WO | 2010/029374 A1 | 3/2010 | |
| WO | 2011036521 | 3/2011 | |
| WO | 2011/053251 A1 | 5/2011 | |
| WO | 2012/117257 A1 | 9/2012 | |
| WO | WO 2012/121461 A1 | 9/2012 | |
| WO | WO 2013/015545 A1 | 1/2013 | |
| WO | WO 2013/019187 A1 | 2/2013 | |
| WO | 2013/052770 A1 | 4/2013 | |
| WO | 2013/059629 A1 | 4/2013 | |
| WO | WO 2013/171146 A1 | 11/2013 | |
| WO | 2014/144241 A1 | 9/2014 | |
| WO | 2014/160404 A1 | 10/2014 | |
| WO | WO 2014/202088 A1 | 12/2014 | |
| WO | 2015/025324 A1 | 2/2015 | |
| WO | WO 2015/074663 A1 | 5/2015 | |
| WO | 2015/160941 A1 | 10/2015 | |
| WO | 2015/195708 A1 | 12/2015 | |
| WO | WO 2016/024008 A1 | 2/2016 | |
| WO | 2016/201286 A1 | 12/2016 | |
| WO | WO 2017/003935 | 1/2017 | |
| WO | 2017/020125 A1 | 2/2017 | |
| WO | 2017/120492 A1 | 7/2017 | |
| WO | 2017/132410 A1 | 8/2017 | |
| WO | WO 2017/135195 A1 | 8/2017 | |
| WO | WO 2017/180707 A1 | 10/2017 | |
| WO | WO 2018/091473 A1 | 11/2017 | |
| WO | WO-2017218918 A1 * | 12/2017 | ........... A61K 31/095 |
| WO | WO 2018/224674 | 12/2018 | |
| WO | WO 2019/219773 | 11/2019 | |
| WO | 2021/028578 A1 | 2/2021 | |
| WO | 2021/037960 A1 | 3/2021 | |
| WO | 2021090309 A1 | 5/2021 | |

OTHER PUBLICATIONS

Asthana et al., "Formulation and Evaluation of Alginate-Based Mucoadhesive Buccal Patch for Delivery of Antimigraine Drug", *Asian J Pharm Clin Res*, 2018, 11(4), 185-191.

Bachelor et al. "Organotypic human oral tissue models for evaluation of oral care products", presented at Society of Toxicology 2014 annual meeting, 2014, 1, 3-7; only abstract available via https://www.mattek.com/referencelibrary/organotypic-human-oral-tissue-models-for-evaluation-of-oral-careproducts/.

Bachynsky et al., "Factors Affecting the Efficiency of a Self-Emulsifying Oral Delivery System", *Drug Dev Ind Pharm*, 1997, 23, 809-816.

Basu et al., "Cannabinoid Receiptor 2 is Critical for the Homing and Retention of Marginal Zone B Lineage Cells and for Efficient T-Independent Immune Responses", *J Immunol*, 2011, 187(11), 5720-5732.

Begg et al., "Evidence for novel cannabinoid receptors", *Pharmacology Et Therapuetics*, 2005, 106(2), 133-145.

Ben Amar, M., "Cannabinoids in medicine: A review of their therapeutic potential", *J Ethnopharmacol*, 2006, 105(1-2), 1-25.

Bhagwati et al., "Bioavailability Enhancement of Rizatriptan Benzoate by Oral Disintegrating Strip: In Vitro and In vivo Evaluation", *Current Drug Delivery*, 2016, 13(3), 462-470.

Bouhassira et al., "Prevalence of chronic pain with neuropathic characteristics in the general population", *Pain*, 2008, 136(3), 380-387.

Bourassa et al., "Label-Free Monitoring of μ-Opioid Receptor-Mediated Signaling", *Mot Pharmacol*, 2014, 86(2), 138-149.

Chey, "Irritable Bowel Syndrome A Clinical Review", *JAMA*, 2015, 313(9), 949-958.

Date et al., "Self-nanoemulsifying drug delivery systems" formulation insights, applications and advances, *Nanomedicine*, 2010, 5(10), 1595-1616.

Davis and Brewster, "Cyclodextrin-Based Pharmaceutics: Past, Present and Future", *Nat Rev Drug Discovery*, 2004, 3, 1023-1035.

Davis and Dickey, "Regulated Airway Goblet Cell Mucin Secretion", *Annu Rev Physiol*, 2008, 70, 487-512.

Dawson et al., "The In Vitro Cell Association of Invasin Coated Polylactide-Co-Glycolide Nanoparticles", *Pharm Res*, 2000, 17(11), 1420-1425.

Dechant et al., "Sumatriptan A Review of its Pharmacodynamic and Pharmacokinetic Properties, and Therapeutic Efficacy in the Acute Treatment of Migraine and Cluster Headache", *Drugs*, 1992, 43(5), 776-798.

Derry et al., "Sumatriptan (all routes of administration) for acute migraine attacks in adults—overview of Cochrane reviews (Review)", *Cochrane Database of Systematic Reviews*, 2014, 5, CD009108.

Dowling et al., "Population Phamacokinetics of Intravenous, Intramuscular, and Intranasal Naloxone in Human Volunteers", *Ther Drug Monit*, 2008, 30(4), 490-496.

Dusquesnoy et al.,"Comparative clinical pharmacokinetics of single doses of sumatriptan following subcutaneous, oral, rectal and intranasal administration", *Eur J Pharm Sci*, 1998, 6(2), 99-104.

ElSohly and Slade, "Chemical constituents of marijuana: The complex mixture of natural cannabinoids" *Life Sciences*, 2005, 78, 539-548.

European Pharmacopoeia, 2013, 2, 1490-1492.

(56) References Cited

OTHER PUBLICATIONS

Ferrari et al., "Interindividual variability of oral sumatriptan pharmacokinetics and of clinical response in migraine patients", *Eur J Clin Pharmacol*, 2008, 64, 489-495.
FMC Biopolymer, Product Specification Bulletin for Protanal® LFR 5/60, version 3, Oct. 12, 2013.
Fowler et al., "The Clinical Pharmacology, Pharmacokinetics and Metabolism of Sumatriptan", *Eur Neural*, 1991, 31, 291-294.
Friedl et al.,"Development and Evaluation of a Novel Mucus Diffusion Test System Approved by Self-Nanoemulsifying Drug Delivery systems", *Pharmaceutics, drug delivery and pharmaceutical technology*, 2013, 102, 4406-4413.
Gizurason et al., "Anatomical and Histological Factors Affecting Intranasal Drug and Vaccine Delivery", *Current Drug Delivery*, 2012, 9, 566-582.
Grubstein and Milano, "Stabilization of epinephrine in a local anesthetic injectable solution using reduced levels of sodium metabisulfite and edta", *Drug Development and Industrial Pharmacy*, 1992, 18(14), 1549-1566.
Gupta et al.,"Design and Development of Oral Transmucosal Film for Delivery of Salbutamol Sulphate", *Journal of Pharmaceutical, Chemical and Biological Sciences*, 2014, 2(2), 118-129.
Haas and Harper, "Ketamine: A Review of Its Pharmacologic Properties and Use in Ambulatory Anesthesia", *Anesth Prag*, 1992, 39, 61-68.
He et al., "Adapting liposomes for oral drug delivery", *Acta Pharmaceutica Sinica B*, 2019, 36-48.
Hussain et al., "Utilizing Bacterial Mechanisms of Epithelial Cell Entry: Invasin-induced Oral Uptake of Latex Nanoparticles", *Pharm Res*, 1998, 15(1), 153-156.
International Preliminary Report on Patentability for International Application No. PCT/EP2017/079217, "Pharmaceutical Formulation", dated May 21, 2019.
International Preliminary Report on Patentability for International Application No. PCT/EP2018/065223, "Pharmaceutical Formulation", dated Dec. 10, 2019.
International Preliminary Report on Patentability for International Application No. PCT/EP2019/062534, "Pharmaceutical Formulation" dated Nov. 17, 2020.
International Preliminary Report on Patentability for International Application No. PCT/EP2019/063376, "Pharmaceutical Formulation" dated Jul. 29, 2019.
International Search Report for International Application No. PCT/EP2017/079217, "Pharmaceutical Formulation", dated Jan. 30, 2019.
International Search Report for International Application No. PCT/EP2018/065223, "Pharmaceutical Formulation", dated Aug. 10, 2018.
International Search Report for International Application No. PCT/EP2019/063376, "Pharmaceutical Formulation" dated Jul. 29, 2019.
International Search Report for International Application No. PCT/EP2019/062534, "Pharmaceutical Formulation" dated Aug. 26, 2019.
Kaminski, "Inhibition of the cAMP signaling cascade via cannabinoid receptors: a putative mechanism of immune modulation by cannabinoid compounds", *Toxicology Lett*, 1998, 102-103, 59-63.
Lee and Mooney, "Alginate: properties and biomedical applications", *Prag Polym Sci*, 2012, 37(1 ), 106-126.
Lim, K., et al., "a Systematic Review of the Effectiveness of Medical Cannabis for Psychiatric, Movement and Neurodegenertive Disorders", Clinical Psychopharmacology and Neuroscience 2017; 15(4): 301-312.
Maas et al., "A model-based approach to treatment comparison in acute migraine", *Br J Clin Pharm*, 2007, 62(5), 591-600.
Managaro and Wertz, "The Effects of Permeabilizers on the In Vitro Penetration of Propranolol Through Porcine Buccal Epithelium", *Mil Med*, 1996, 161 (11 ), 669-672.
Marasini et al., "Development and Optimization of Self-Nanoemulsifying Drug Delivery system with Enhanced Bioavailability by Box-Behnken Design and Desirability Function", *J Pharm Sci*, 2012, 101, 4584-4596.

Marttin et al., "The effect of methylated β-cyclodextrins on the tight junctions of the rat nasal respiratory epithelium: Electron Microscopic and confocal laser scanning microscopic visualization studies", *J Control Release*, 1999, 57, 205-213.
Mclean-Tooke et al., "Adrenaline in the treatment of anaphylaxis: what is the evidence?" *BMJ*, 2003, 327(7427), 1332-1335.
Mechoulam et al., "Cannabidiol—Recent Advances" *Chemistry Et Biodiversity*, 2007, 4, 1678-1692.
Merkus et al., "Cyclodestrins in nasal drug delivery", *Adv Drug Del Rev*, 1999, 36, 41-57.
Muller et al., "Ketamine enantiomers in the rapid and sustained antidepressant effects", *Ther Adv Psychopharmacol*, 2016, 6, 185-192.
Nadel, "Acute effects of inhalation of cigarette smoke on airway conductance", *J Appl Physiol*, 1961, 16, 713-716.
Nicholson, Ulcerative Colitis Statistics, 2016, accessed at InflammatoryBowelDisease.net, Sep. 30, 2019, 2 pages.
Non-Final Office Action for U.S. Appl. No. 16/349,840 "Pharmaceutical Formulation" dated Oct. 6, 2020.
Notice of Allowance for U.S. Appl. No. 16/349,840 "Pharmaceutical Formulation" dated Jan. 14, 2021.
Oesterling, "The adverse effect of ascorbic acid on the stability of adrenaline and noadrenaline solutions", *Biochim Biophys Acta*, 1957, 24(1), 178-187.
Office Action for U.S. Appl. No. 16/607,892, "Pharmaceutical Formulation" dated Feb. 25, 2021.
Owen et al., "The Preclinical toxicological evaluation of sumatriptan", *Human Et Experimental Toxicology*, 1995, 14, 959-973.
Ozaki et al., "Inhibition of Crystal Nucleation and Growth by Water-Soluble Polymers and its Impact on the Supersaturation Profiles of Amorphous Drugs", *J Pharm Sci*, 2013, 102, 2273-2281.
Parish et al.,"A systematic review of epinephrine degradation with exposure to excessive heat or cold", *Annals of Allergy, Asthma Et Immunology*, 2016, 117(1), 79-87.
Paudel et al., "Cannabidiol bioavailability after nasal and transdermal application: effect of permeation enhancers", *Drug Dev Ind Pharm*, 2010, 36, 1088-1097.
Pertwee, "The pharmacology of cannabinoid receptors and their ligands: an overview", *IntJObesity*, 2006, 30, S13-S18.
Pouton, "Formulation of poorly water-soluble drugs for oral administration: Physicochemical and physiological issues and the lipid formulation classification system", *European Journal of Pharmaceutical Sciences*, 2006, 29(3-4), 278-287.
Prachayasittikul et al., "EDTA-induced Membrane Fluidization and Destabilization: Biophysical Studies on Artificial Lipid Membranes", *Acta biochimica et biophysica Sinica*, 2007, 39(11 ), 901-913.
Pradhan et al., "Fabrication of a uniformly sized fenofibrate microemulsion by membrane emulsification", *J Microencapsul*, 2013, 30, 42-48.
Sayed et al., "Fast-Dissolving Sublingual Films of Terbutaline Sulfate: Formulation and In Vitro/In Vivo Evaluation", *Mot Pharmaceutics*, 2013, 10(8), 2942-2947.
Shannon, R.D. "Revised Effective Ionic Radii and Systematic Studies of Interatomic in Halides and Chalcogenides", Act Cryst. (1976) A 22, 751.
Sharma et al., "Development and Characterization of Self Emulsifying Drug Delivery system of a Poorly Water Soluble Drug Using Natural Oil", *Acta Pol Pharm*, 2012, 69, 713-717.
Shojaei, "Buccal Mucosa As a Route for Systemic Drug Delivery: A Review", *J Pharmaceut Sci*, 1998, 1 (1) 15-30.
Shtenberg et al., "Mucoadhesive alginate pastes with embedded liposomes for local oral drug delivery", *Int J Biol Macromol*, 2018, 111, 62-69.
Simons, "Epinephrine absorption in children with a history of anaphylaxis", *J Clin Immunol*, 1998, 101, 33-37.
Sinner and Graf, "Ketamine" in Modern Anesthetics: *Handbook of Experimental Pharmacoogy. Eds.* Schuttler and Schwilden, 182, 313-333 (2008).
Skulason et al., "Evaluation of polymeric films for buccal drug delivery", *Pharmazie*, 2009, 64(3), 197-201.

(56) References Cited

OTHER PUBLICATIONS

Sperger et al., "Analysis of Composition, Molecular Weight, and Water Content Variations in Sodium Alginate Using Solid-State NMR Spectroscopy", *J Pharmaceut Sci*, 2011, 100, 3441-3452.

Squier and Wertz. "Structure and function of the oral mucosa and implications for drug delivery" in *Oral mucosa[ drug delivery*. Ed. Rathbone; pub. Dekker, 1996, 1-25.

Stepensky et al., "Long-Term Stability Study of 1-Adrenaline Injections: Kinetics of Sulfonatation and Racemization Pathways of Drug Degradation", *J Pharmaceut Sci*, 2004, 93(4), 969-980.

Stout and Cimino, "Analysis of Composition, Molecular Weight, and Water Content Variations in Sodium Alginate Using Solid-State NMR Spectroscopy", *Drug Met Rev*, 2014, 46(1), 86-95.

Tashkin, "Acute Effects of Smoked Marijuana and Oral $\Delta^\circ$-Tetrahydrocannabinol on Specific Airway Conductance in Asthmatic Subjects[1-3]", *Am Rev Respir Dis*, 1974, 109, 420-428.

Tayel et al., "Sumatriptan succinate sublingual fast dissolving thin films: formulation and in vitro/invivo evaluation", *Pharm Dev Technol*, 2016, 31, 328-337.

Thakur et al., "Transdermal and Buccal Delivery of Methylxanthines Through Human Tissue in Vitro", *Drug Dev. Ind. Pharm.*, 2007, 33(5), 513-521.

Tuleu et al., "Short term stability of pH-adjusted lidocaine-adrenaline epidural solution used for emergency caesarean section", *International Journal of Obstetric Anesthesia*, 2008, 17(2), 118-122.

Tylleskar et al., "Pharmacokinetics of a new, nasal formulation of naloxone", *Eur J Clin Pharmacol*, 2017, 73, 555-562.

Written Opinion for International Application No. PCT/EP2017/079217, "Pharmaceutical Formulation", dated May 21, 2019.

Written Opinion for International Application No. PCT/EP2018/065223, "Pharmaceutical Formulation", dated Aug. 10, 2018.

Written Opinion of the International Searching Authority for International Application No. PCT/EP2019/062534, "Pharmaceutical Formulation" dated Jul. 29, 2019.

Written Opinion of the International Searching Authority for International Application No. PCT/EP2019/063376, "Pharmaceutical Formulation" dated Jul. 29, 2019.

www.epipen.com/hcp/media/files/epipen/prescribing information. pdf Aug. 2012, 2 pages.

Zgair et al., "Development of a simple and sensitive HPLC-UV method for the simultaneous determination of cannabidiol and $\Delta^9$-tetrahydrocannabinol in rat plasma" *J Pharmaceut Biomed Anal*, 2015, 114, 145-151.

Manfredi, P.L., et al., "Sumatriptan for Headache Caused by Head and Neck Cancer", Headache 2000; 40:758-760.

Notice of Allowance for U.S. Appl. No. 16/607,892 "Pharmaceutical Formulation" dated Oct. 1, 2021.

Dixit et al., "Iontophoresis—An Approach for Controlled Drug Delivery: A Review", Current Drug Delivery, 2007, 4, pp. 1-10.

Harding, S.E., et al., "Molecular Weidht Determination of Polysaccharides", Advances in Carbohydrate Analysis, 1991, vol. 1, pp. 69-73.

Martinsen, A., et al., "Comparision of Different Methods for Determination of Molecular Weight and Molecular Weight Distribution of Alginates", Carbohydrate Polymers 15 (1991) 171-193.

Rawas-Qalaji, et al., "Fast-disintegrating Sublingual Tablets: Effect of Epinephrine Load on Tablet Characteristics", AAPS PharmSciTech 2006; 7 (2) Article 41.

Non-Final Office Action for U.S. Appl. No. 17/054,941 "Pharmaceutical Formulation" dated Dec. 13, 2021.

International Preliminary Report on Patentability for international application No. PCT/EP2020/072894, entitled "Film Formulation Comprising Carriers," dated Feb. 24, 2022.

International Search Report for international application No. PCT/EP2020/072894, entitled "Film Formulation Comprising Carriers," dated Oct. 26, 2020.

Written Opinion for international application No. PCT/EP2020/072894, entitled "Film Formulation Comprising Carriers," dated Oct. 26, 2020.

International Search Report for international application No. PCT/EP2020/073940, entitled "Film Formulation Comprising Carriers," dated Dec. 6, 2020.

Written Opinion for international application No. PCT/EP2020/073940, entitled "Pharmaceutical Formulation," dated Dec. 6, 2020.

International Preliminary Report on Patentability for international application No. PCT/EP2020/073940, entitled "Film Formulation Comprising Carriers," date of issuance: Mar. 1, 2022.

Klaria Pharma Holding AB, Experimental Report filed on Jul. 28, 2020 in relation to European patent application No. 17804124.0.

Non-Final Office Action for U.S. Appl. No. 17/215,963, "Pharmaceutical Formulation", dated Apr. 13, 2022.

Brookfield AMETEK, "More Solutions to Sticky Problems", accessed at https://www.brookfieldengineering.com/-/media/ametekbrookfield/tech%20sheets/more%20solutions%202017.pdf?la=en, 2017, 31 pages (2017).

"Alzheimer's Association: 10 Early Signs and Symptoms of Alzheimer's," accessed at https://www.alz.org/10-signs-symptoms-alzheimers-dementia.asp (2018), 9 pages.

FMC Corporation, FMC Biopolymer, Product Specification for Manucol® LB, (2013).

Pubchem, Compound Summary for Naloxone, https://pubchem.ncbi.nlm.nih.gov/compound/naloxone, C19H21NO497, downloaded on Aug. 13, 2019.

Glaxosmithkline, UK, Imigran® 10 mg Nasal Spray—Summary of Product Characteristics updated Feb. 26, 2015 (SmPC), https://www.medicines.org.uk/emc/product/2214/smpc.ines.org.uk/emc/product/2214/smpc.

Glaxosmithkline, UK, Imigran® Injection, Subject—Summary of Product Characteristics May 4, 2018 (SmPC), https://www.medicines.org.uk/emc/product/944/smpc.

Glaxosmithkline, UK, Imigran® Tablets, 50 mg—Summary of Product Characteristics updated Oct. 6, 2020 (SmPC), https://www.medicines.org.uk/emc/product/945/smpc.

Glaxosmithkline, UK, Imigran Tablets 50 mg, Summary of Product Characteristics updated Oct. 3, 2016, https://www.medicines.org.uk/emc/product/945/smpc.

Klaria Pharma Holding AB, Klaria press releases dated Oct. 29, 2015, Feb. 24, 2016, Apr. 19, 2016, Nov. 5, 2016, Jan. 7, 2016 and Aug. 15, 2016.

Light, M.K., et al., The Marijuana Policy Group, Market Size and Demand for Marijuana in Colorado, Prepared for the Colorado Department of Revenue, http://www.cannabisconsumer.org/uploads/9/7/9/6/97962014/market size and demand study, July 9, 2014%5B1%5D.pdf.

NIDDK (National Institute of Diabetes and Digestive and Kidney Diseases), Definition and Facts for Crohn's Disease, accessed at https://www.niddk.nih.gov/health-information/digestive-diseases/crohns-disease/definition-facts (2017), 3 pages.

Drugs.com: Imitrex: Uses, Dosage, Side Effects and Warnings: https://www.drugs.com/imitrex.html, Aug. 13, 2019, 6 pages.

Drugs.com, Sumatriptan Monograph for Professionals, https://www.drugs.com/monograph/sumatriptan.html, downloaded Aug. 13, 2019, 28 pages.

Manna Molecular Science, LLC, Forms of Cannabis Intake http://www.mannamolecular.com/2016/09/forms-of-cannabis-intake, downloaded Aug. 13, 2019, 6 pages.

Finkelstein, S., "Nasal Spray for Migraines", www.migraine.com/migraine-treatment/nasal-spray, downloaded Aug. 13, 2019, 6 pages.

Third Party Observation for EP Application No. 19728321.1 (EP 3793517) "Pharmaceutical Formulation" dated Aug. 23, 2021.

Final Office Action for U.S. Appl. No. 17/054,941 "Pharmaceutical Formulation" dated Aug. 2, 2022.

Murata, Y., et al., Preparation of Fast Dissolving Films for Oral Dosage from Natural Polysaccharides, Materials, 2010, 3, 4291-4299.

Alayoubi, A., et al., "Development of a fast dissolving film of epinephrine hydrochloride as a potential anaphylactic treatment for pediatrics", harm Dev Technol, Jan. 6, 2016, 7 pages.

Non-Final Office Action for U.S. Appl. No. 17/054,941 "Pharmaceutical Formulation" dated Apr. 27, 2023.

Non-Final Office Action for U.S. Appl. No. 17/457,460 "Pharmaceutical Formulation" dated Jun. 22, 2023.

(56) References Cited

OTHER PUBLICATIONS

Chen, Ming J. et al. (2006). "Film-Forming Polymers in Fast-Dissolve Oral Films", Annual Meeting and Exposition of the American Association of Pharmaceutical Scientists, Oct. 29-Nov. 2, 2006, San Antonio, TX, USA.

USPTO Notice of Allowance for U.S. Appl. No. 17/457,460, filed Dec. 3, 2021, titled "Pharmaceutical Formulation", dated Oct. 25, 2023.

\* cited by examiner (A)

(B)

(A)

(B)

PHARMACEUTICAL FORMULATION

RELATED APPLICATIONS

This application is the U.S. National Stage of International Application No. PCT/EP2019/063376, filed May 23, 2019, which designates the U.S., published in English, and claims priority under 35 U.S.C. § 119 or 365(c) to GB Application No. 1808462.4, filed May 23, 2018. The entire teachings of the above applications are incorporated herein by reference.

FIELD OF THE INVENTION

The present invention relates to a film comprising an alginate salt of a monovalent cation or a mixture of alginate salts containing at least one alginate salt of a monovalent cation, and a compound of Formula (I), such as adrenaline, or a pharmaceutically acceptable salt thereof. The present invention further relates to methods for manufacturing such a film, and the use of such a film in the treatment of disease, in particular the treatment of anaphylaxis, superficial bleeding and cardiac arrest.

BACKGROUND TO THE INVENTION

Adrenaline is a hormone and neurotransmitter that is normally produced in the human body by the adrenal glands and certain neurones. It plays an important role in the "flight or fight" response by (e.g.) increasing blood flow to muscles, heart rate, output of the heart, respiratory rate, bronchodilation, pupil dilation, and blood sugar levels. At the molecular level, adrenaline acts on $\alpha$- and $\beta$-adrenergic receptors.

Adrenaline is also useful as a medicament in the treatment of a number of conditions. In particular, it is used to treat conditions including anaphylaxis, superficial bleeding and cardiac arrest. In anaphylaxis, which is a severe, life threatening systemic reaction, adrenaline is indicated in the emergency treatment of allergic reactions including anaphylaxis to stings, contrast agents, medicines or in people with a history of anaphylactic reactions to known triggers. It is believed that adrenaline mediates the effects of anaphylaxis through (a) stimulation of $\alpha$-adrenoceptors, increasing peripheral vascular resistance thus improving blood pressure and coronary perfusion, reversing peripheral vasodilation, and decreasing angioedema, (b) stimulation of $\beta_1$ adrenoceptors, giving positive inotropic and chronotropic cardiac effects, and (c) stimulation of $\beta_2$ adrenoceptors, causing bronchodilation and increasing intracellular cyclic adenosine monophosphate production in mast cells and basophils, reducing release of inflammatory mediators. [1] The recommend dose of adrenaline in the treatment of anaphylaxis is around 0.3-1.0 mg in adults, and 0.01 mg/kg in infants and children. [1] Adrenaline is also useful in the treatment of superficial bleeding, including abrasions and nosebleeds. Adrenaline reduces blood flow to the skin by constriction of small blood vessels, and therefore local or systemic application of adrenaline may be used to divert blood flow away from the site of injury and hence reduce bleeding from wounds. Adrenaline has also been used as a suppository to constrict blood vessels and thereby shrink haemorrhoids. In a related use, adrenaline can also be mixed with local anaesthetics (e.g. lignocaine) to prevent the diffusion of the anaesthetic away from the site of action, prolong its numbing effect, and lessen toxicity and arrest bleeding by constricting the small blood vessels. [2]

The only currently available formulations of adrenaline for e.g. treatment of anaphylaxis are injectable formulations; in particular, intramuscular injection is recommended. However, intramuscular injection is invasive and carries a risk of needle-stick injuries in first responders and caregivers. Furthermore, intramuscular injection can be difficult as the depth of subcutaneous fat varies between patients, and may result instead in subcutaneous or intravenous injection. Subcutaneous injection is thought to be associated with a significantly delayed time of peak plasma concentration of adrenaline compared with intramuscular injection. [3] Meanwhile, intravenous dosing of adrenaline may be associated in many patients with undesirable side effects, sometimes even severe or fatal, and should be reserved only for those patients with unresponsive anaphylaxis. [1]

Further, solution formulations of adrenaline are known to have low stability, resulting in a low shelf life of formulations. In particular, oxidation is the primary route for degradation of adrenaline in aqueous solution. This process is accelerated by exposure to light, oxygen, neutral or alkaline pH, or increased temperature. The influence of pH is thought to be the primary determinant of adrenaline stability. The stability of adrenaline is optimal around pH 3-4 and acceptable below pH 5.5. [4]

In summary, no formulation of adrenaline is currently available which can be administered in a non-invasive fashion, is needle-free and which results in acceptable bioavailability and blood plasma concentrations of adrenaline with low variability between patients, and which is sufficiently stable so as to have an acceptable shelf life as a medicinal product.

SUMMARY OF THE INVENTION

The present invention is based on the unexpected finding that formulations of a compound of Formula (I), such as adrenaline, or pharmaceutically acceptable salts thereof, in a film suitable for administration to an oral cavity can provide an advantageous balance of properties. This balance of properties is desirable for use in the treatment of conditions such as anaphylaxis, superficial bleeding and cardiac arrest. In particular, where the film formulation comprises adrenaline or a pharmaceutically acceptable salt thereof, the properties of the film compare favourably with those of intramuscular adrenaline-containing formulations. The film formulations of adrenaline can potentially provide a needle-free alternative to intramuscular formulations, whilst enabling acceptable plasma levels of adrenaline to be delivered to patients, with low variability between patients. Further, the film formulations of adrenaline were found to be essentially stable for 83 days at room temperature.

Hence, the invention provides for the first time a film suitable for administration to an oral cavity comprising a compound of Formula (I), such as adrenaline, its use in the treatment of patients suffering from conditions such as anaphylaxis, superficial bleeding and cardiac arrest, and methods for its manufacture.

In one aspect, the present invention provides a film suitable for administration to an oral cavity comprising:
(i) an alginate salt of a monovalent cation or a mixture of alginate salts containing at least one alginate salt of a monovalent cation; and (ii) an active pharmaceutical ingredient (API) which is a compound of Formula (I) or a pharmaceutically acceptable salt thereof

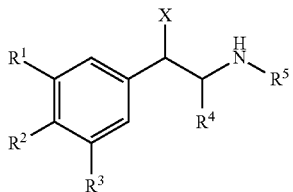

(I)

wherein:
X is selected from hydrogen and OH;
R$^1$ is selected from hydrogen, OH and CH$_2$OH;
R$^2$ and R$^3$ are independently selected from hydrogen and OH;
R$^4$ is selected from hydrogen and methyl; and
R$^5$ is selected from hydrogen and C$_{1-4}$ alkyl;
further wherein the alginate salt of a monovalent cation (a) comprises from 25 to 35% by weight of β-D-mannuronate and/or from 65 to 75% by weight of α-L-guluronate, and (b) has a mean molecular weight of from 30,000 g/mol to 90,000 g/mol.

In another aspect, the present invention provides a film according to the invention for use in the treatment of a human patient.

In another aspect, the present invention provides a film according to the invention for use in the treatment of anaphylaxis, superficial bleeding or cardiac arrest, in a human patient.

In a further aspect, the present invention provides a method of treating anaphylaxis, superficial bleeding or cardiac arrest in a human patient, wherein said method comprises administration of at least one film according to the invention to the human patient.

In another aspect, the present invention provides the use of a film according to the invention for the manufacture of a medicament for the treatment of anaphylaxis, superficial bleeding or cardiac arrest in a human patient.

In another aspect, the present invention provides a method of manufacturing a film according to the invention, said method comprising the following steps:

(a) either the steps of:
  (i) optionally, mixing at least one antioxidant in water;
  (ii) mixing the API in water, or in the solution obtained in step (i), and optionally subsequently adjusting the pH of the solution to the desired level by addition of an appropriate acid or base, typically a diluted aqueous acid or alkali, more typically a diluted aqueous alkali, and preferably adjusting the pH of the solution to from 3.8 to 5.5;
  (iii) optionally, mixing one or more excipients into the solution obtained in step (ii); and
  (iv) adding the alginate salt of monovalent cation under suitable conditions to result in the formation of a viscous cast;
or alternatively the steps of:
  (i) mixing one or more excipients in water;
  (ii) separately, dissolving the API in water, or an aqueous solution containing one or more antioxidants, and optionally adjusting the pH of the solution to the desired level by addition of an appropriate acid or base, typically a diluted aqueous acid or alkali, more typically a diluted aqueous alkali, and preferably adjusting the pH of the solution to from 3.8 to 5.5;
  (iii) mixing the solution obtained in step (i) with the alginate salt of monovalent cation; and
  (iv) adding the alginate salt of monovalent cation under suitable conditions to result in the formation of a viscous cast;
(b) optionally, leaving the cast to de-aerate;
(c) pouring the cast onto a surface and spreading the cast out to the desired thickness;
(d) drying the cast layer, typically at a temperature of from 30 to 60° C. until the residual water content of the film is from 0 to 20% by weight and a solid film is formed; and
(e) optionally, cutting the solid film into pieces of the desired size, further optionally placing these pieces into pouches, preferably wherein the pouches are made from PET-lined aluminium, sealing the pouches and further optionally, labelling them.

DETAILED DESCRIPTION OF THE INVENTION

Figure 1:
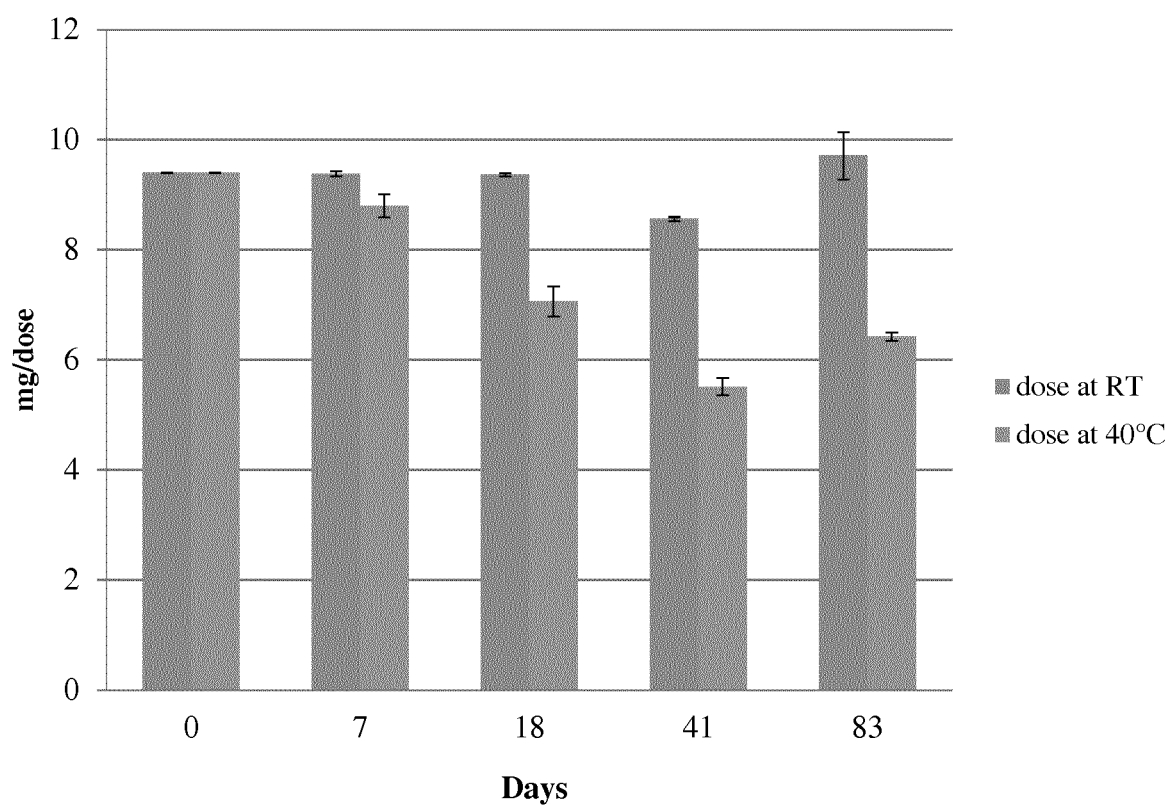
FIG. 1 shows the amount of adrenaline present (as mg/dose) in a film formulation also comprising ascorbic acid at various time points when stored either at room temperature (25° C.; bars on left-hand side of each pair) or 40° C. (bars on right-hand side of each pair) over a period of 83 days.

The present invention is concerned with a film, suitable for administration to an oral cavity, which can be used for delivery of a compound of Formula (I), such as adrenaline, or a pharmaceutically acceptable salt thereof to a human patient. Such a film may also be referred to as an oral dissolvable film (ODF) and/or an oral transmucosal film (OTF). The film is typically an alginate film which is applied by the patient themselves or another person, e.g. a medical practitioner, a nurse, a carer, a social worker, a colleague of the patient or a family member of the patient, to the mucosa of the oral cavity. The film is bioadhesive and adheres to the surface of the oral cavity upon application. After application, the alginate film begins to dissolve, releasing the active pharmaceutical ingredient. The present invention is useful in particular in the treatment of anaphylaxis, superficial bleeding and cardiac arrest.

For the avoidance of doubt, all alternative and preferred features relating to the film per se apply equally to the use of said film in the treatment of a human patient.

Definitions

As defined herein, the term "alkyl" refers to a linear or branched saturated monovalent hydrocarbon radical having the number of carbon atoms indicated in the prefix. Thus, the term "$C_{1-4}$ alkyl" refers to a linear saturated monovalent hydrocarbon radical of one to four carbon atoms or a branched saturated monovalent hydrocarbon radical of three or four carbon atoms, e.g. methyl, ethyl, n-propyl, iso-propyl, n-butyl, iso-butyl and tert-butyl.

As defined herein, the term "acyl" refers to a —COR radical, wherein R is alkyl, haloalkyl, cycloalkyl, cycloalkylalkyl, aryl, aralkyl, heteroaryl, heteroaralkyl, heterocyclyl, or heterocyclylalkyl, each as defined herein, or poly(ethylene glycol), and wherein R is optionally further substituted with one, two, three, four or more substituents independently selected from alkyl, alkoxy, halo, haloalkoxy, —OH, —NH$_2$, alkylamino, —COOH, or alkoxycarbonyl.

As defined herein, the term "alkoxy" refers to an —OR radical where R is alkyl as defined above, e.g., methoxy, ethoxy, n-propoxy, iso-propoxy, n-butyl, iso-butyl, tert-butyl and the like.

As defined herein, the term "alkoxycarbonyl" refers to a —C(O)OR radical where R is alkyl, haloalkyl, cycloalkyl, cycloalkylalkyl, aryl, aralkyl, heteroaryl, heteroaralkyl, heterocyclyl, or heterocyclylalkyl, each as defined herein, or poly(ethylene glycol), and wherein R is optionally further substituted with one, two, three, four or more substituents independently selected from alkyl, alkoxy, halo, haloalkoxy, —OH, —NH$_2$, alkylamino, —COOH, or alkoxycarbonyl.

As defined herein, the term "alkylamino" refers to an —NHR radical where R is alkyl as defined above, e.g. methylamino, ethylamino, n-propylamino, iso-propylamino, and the like.

As defined herein, the term "aryl" refers to a monovalent monocyclic or bicyclic aromatic hydrocarbon radical of 6 to 10 ring atoms, e.g. phenyl or naphthyl, and the like.

As defined herein, the term "aralkyl" refers to an -(alkylene)-R radical where R is aryl as defined above.

As defined herein, the term "carbamate" refers to a —C(O)NR$^x$R$^y$ radical where R$^x$ and R$^y$ are independently hydrogen, alkyl, haloalkyl, cycloalkyl, cycloalkylalkyl, aryl, aralkyl, heteroaryl, heteroaralkyl, heterocyclyl, or heterocyclylalkyl, each as defined herein, or poly(ethylene glycol), and wherein R$^x$ and R$^y$ are optionally further substituted with one, two, three, four or more substituents independently selected from alkyl, alkoxy, halo, haloalkoxy, —OH, —NH$_2$, alkylamino, —COOH, or alkoxycarbonyl.

As defined herein, the term "cycloalkyl" refers to a cyclic saturated monovalent hydrocarbon radical of three to ten carbon atoms wherein one or two carbon atoms may be replaced by an oxo group, e.g. cyclopropyl, cyclobutyl, cyclopentyl, or cyclohexyl, and the like.

As defined herein, the term "cycloalkylalkyl" refers to an -(alkylene)-R radical where R is cycloalkyl as defined above, e.g. cyclopropylmethyl, cyclobutylmethyl, cyclopentylethyl, or cyclohexylmethyl, and the like.

As defined herein, the term "halo" refers to fluoro, chloro, bromo, or iodo, preferably fluoro or chloro.

As defined herein, the term "haloalkyl" refers to an alkyl radical as defined above, which is substituted with one or more halogen atoms, preferably one to five halogen atoms, preferably fluorine or chlorine, including those substituted with different halogens, e.g. —CH$_2$Cl, —CF$_3$, —CHF$_2$, —CH$_2$CF$_3$, —CF$_2$CF$_3$, —CF(CH$_3$)$_2$, and the like.

As defined herein, the term "haloalkoxy" refers to an —OR radical where R is haloalkyl as defined above, e.g. —OCF$_3$, —OCHF$_2$, and the like.

As defined herein, the term "heteroaryl" refers to a monovalent monocyclic or bicyclic aromatic radical of 5 to 10 ring atoms where one or more, preferably one, two, or three, ring atoms are heteroatom selected from N, O, or S, the remaining ring atoms being carbon. Representative examples include, but are not limited to, pyrrolyl, thienyl, thiazolyl, imidazolyl, furanyl, indolyl, isoindolyl, oxazolyl, isoxazolyl, benzothiazolyl, benzoxazolyl, quinolinyl, isoquinolinyl, pyridinyl, pyrimidinyl, pyrazinyl, pyridazinyl, triazolyl, tetrazolyl, and the like.

As defined herein, the term "heteroaralkyl" refers to an -(alkylene)-R radical where R is heteroaryl as defined above.

As defined herein, the term "heterocycyl" refers to a saturated or unsaturated monovalent monocyclic group of 4 to 8 ring atoms in which one or two ring atoms are heteroatoms selected from N, O, or $S(O)_n$, where n is an integer from 0 to 2, the remaining ring atoms being C. The heterocyclyl ring is optionally fused to a (one) aryl or heteroaryl ring as defined herein provided the aryl and heteroaryl rings are monocyclic. Additionally, one or two ring carbon atoms in the heterocyclyl ring can optionally be replaced by a —CO— group. More specifically the term heterocyclyl includes, but is not limited to, pyrrolidino, piperidino, homopiperidino, 2-oxopyrrolidinyl, 2-oxopiperidinyl, morpholino, piperazino, tetrahydropyranyl, thiomorpholino, and the like. When the heterocyclyl ring is unsaturated it can contain one or two ring double bonds, provided that the ring is not aromatic.

As defined herein, the term "heterocycloalkyl" refers to an -(alkylene)-R radical where R is heterocyclyl ring as defined above, e.g. tetraydrofuranylmethyl, piperazinylmethyl, morpholinylethyl, and the like.

As defined herein, "room temperature" refers to a temperature of 25° C.

As defined herein, the term "oral cavity" is understood to mean the cavity of the mouth, and includes the inner upper and lower lips, all parts of the inner cheek, the sublingual area under the tongue, the tongue itself, as well as the upper and lower gums and the hard and soft palate.

As defined herein, the term "oral mucosa" is understood to mean the mucous membrane lining the inside of the mouth, and includes (but does not exclusively refer to) mucosa in the buccal, labial, sublingual, ginigival or lip areas, the soft palate and the hard palate.

Films of the Present Invention

The present invention provides a film suitable for administration to an oral cavity comprising:
(i) an alginate salt of a monovalent cation or a mixture of alginate salts containing at least one alginate salt of a monovalent cation; and
(ii) an active pharmaceutical ingredient (API) which is a compound of Formula (I) or a pharmaceutically acceptable salt thereof

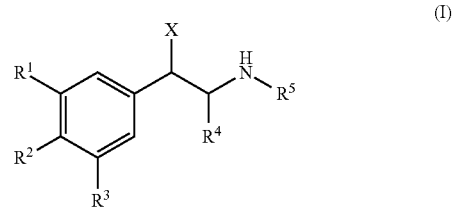

(I)

wherein:
X is selected from hydrogen and OH;
$R^1$ is selected from hydrogen, OH and $CH_2OH$;
$R^2$ and $R^3$ are independently selected from hydrogen and OH;
$R^4$ is selected from hydrogen and methyl; and
$R^5$ is selected from hydrogen and $C_{1-4}$ alkyl.

Preferably, the compound of Formula (I) is adrenaline. More preferably, the compound of Formula (I) is (−)-adrenaline. Alternatively, the compound of Formula (I) is a racemic mixture of (−)-adrenaline and (+)-adrenaline.

The function of said alginate salt of a monovalent cation or mixture of alginate salts containing at least one alginate salt of a monovalent cation within the film is to act as a film-forming agent. As used herein, the term "film-forming agent" refers to a chemical or group of chemicals that form a pliable, cohesive and continuous covering when applied to a surface.

Alginate, the salt of alginic acid, is a linear polysaccharide naturally produced by brown seaweeds (Phaeophyceae, mainly *Laminaria*). Typically the alginate employed in the present invention comprises from 100 to 3000 monomer residues linked together in a flexible chain. These residues are of two types, namely β-(1,4)-linked D-mannuronic acid (M) residues and α-(1,4)-linked L-guluronic acid (G) residues. Typically, at physiological pH, the carboxylic acid group of each residue in the polymer is ionised. The two residue types are epimers of one another, differing only in their stereochemistry at the C5 position, with D-mannuronic acid residues being enzymatically converted to L-guluronic acid residues after polymerization. However, in the polymer chain the two residue types give rise to very different conformations: any two adjacent D-mannuronic acid residues are $^4C_1$-diequatorially linked whilst any two adjacent L-guluronic acid residues are $^4C_1$-diaxially linked, as illustrated in Formula (II) below.

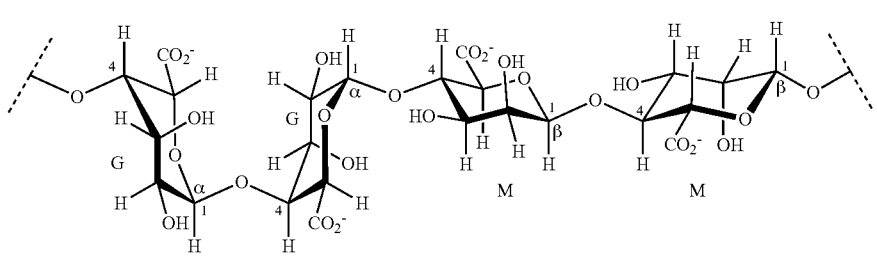

Formula (II)

Typically in the alginate polymer, the residues are organised in blocks of identical or strictly alternating residues, e.g. MMMMM . . . , GGGGG . . . or GMGMGM . . . . Different monovalent and polyvalent cations may be present as counter ions to the negatively-charged carboxylate groups of the D-mannuronic acid and L-guluronic acid residues of the alginate polymer. Typically, the film comprises an alginate salt wherein the counter ions of the alginate polymer are monovalent cations. The cations which are the counterions of a single alginate polymer molecule may all be the same as one another or may be different to one another. Preferably, the counterions of the alginate polymer are selected from the group consisting of $Na^+$, $K^+$ and $NH_4^+$. More preferably, the counterions of the alginate polymer are $Na^+$. Alternatively, the film may comprise a mixture of alginate salts containing at least one alginate salt of a monovalent cation. The mixture of alginate salts may comprise an alginate salt of a cation selected from the group consisting of $Na^+$, $K^+$ and $NH_4^+$.

Typically, the film comprises an alginate composition which has a dynamic viscosity, as measured on a 10% aqueous solution (w/w) thereof at a temperature of 20° C. with a Brookfield LVF viscometer (obtained from Brookfield Engineering Laboratories, Inc.), using a spindle No. 2 at a shear rate of 20 rpm, of 100-1000 mPa·s, or 200-800 mPa·s, or 300-700 mPa·s.

Preferably, the film comprises an alginate composition having a mean guluronate (G) content of from 50 to 85%, more preferably from 60 to 80%, and most preferably from 65 to 75% by weight. Preferably, the film comprises an alginate composition having a mean maluronate (M) content of from 15 to 50%, more preferably from 20 to 40%, and most preferably from 25 to 35% by weight. Preferably, the film comprises an alginate composition having a mean molecular weight ranging from 30,000 g/mol to 90,000 g/mol, such as from 35,000 g/mol to 85,000 g/mol, or from 40,000 g/mol to 70,000 g/mol, or from 40,000 g/mol to 50,000 g/mol. Preferably, the film comprises an alginate composition having a mean guluronate (G) content of from 50 to 85%, a mean maluronate (M) content of from 15 to 50%, and a mean molecular weight ranging from 30,000 g/mol to 90,000 g/mol. More preferably, the film comprises an alginate composition having a mean guluronate (G) content of from 60 to 80%, a mean maluronate (M) content of from 20 to 40%, and a mean molecular weight ranging from 30,000 g/mol to 90,000 g/mol. Most preferably, the film comprises an alginate composition having a mean guluronate (G) content of from 65 to 75%, a mean maluronate (M) content of from 25 to 35%, and a mean molecular weight ranging from 30,000 g/mol to 90,000 g/mol. Without wishing to be bound by any particular theory, it is believed that it is a combination of both (a) the particular mean relative proportions of maluronate and guluronate in the alginate composition and (b) the particular mean molecular weight of the alginate composition that endow the film with its desirable bioadhesive properties.

The alginate salt of a monovalent cation or the mixture of alginate salts containing at least one alginate salt of a monovalent cation may be the sole film-forming agent present in the film. Alternatively, the film may comprise one or more further film-forming agents in addition to the alginate salt of a monovalent cation or the mixture of alginate salts containing at least one alginate salt of a monovalent cation.

It is preferred that the film comprises PROTONAL® LFR 5/60 sodium alginate or PROTONAL® LF 10/60 sodium alginate (both commercially available sodium alginate products from FMC BioPolymer) as the alginate salt. PROTONAL® LFR 5/60 sodium alginate is a low molecular weight and low viscosity sodium alginate extracted from the stem of *Laminaria hyperborean*. PROTONAL® LF 10/60 sodium alginate is a sodium alginate having a G/M % ratio of 65-75/25-35 and a viscosity of from 20-70 mPas as measured on a 1% aqueous solution thereof at a temperature of 20° C. with a Brookfield LVF viscometer, using a spindle No. 2 at a shear rate of 20 rpm. PROTONAL® LF 10/60 sodium alginate has both a higher mean molecular weight and a higher viscosity than PROTONAL® LFR 5/60 sodium alginate.

Without wishing to be bound by any particular theory, a film comprising a higher viscosity alginate salt is believed to have a longer residence time (i.e. dissolving time) after application to the oral cavity via adhesion to a mucous membrane of said cavity than a film comprising a lower viscosity alginate salt of a similar thickness. It is contemplated that the viscosity of the alginate composition within the film may be adjusted by mixing any number of alginates having different viscosities. Typically, a film of about 1 mm thickness comprising PROTONAL® LFR 5/60 sodium alginate as the sole alginate component has a residence time of approximately 3-10 minutes after adhesion to a mucous membrane of the oral cavity. In contrast, a film of about 1 mm thickness comprising PROTONAL® LF 10/60 sodium alginate as the sole alginate component has a residence time of approximately 30 minutes after adhesion to a mucous membrane of the oral cavity.

Therefore, if a long residence time of the film within the oral cavity is desired, it is generally preferred that the film comprises PROTONAL® LF 10/60 sodium alginate as the alginate salt. However, compared to films comprising PROTONAL® LFR 5/60 sodium alginate as the alginate salt, films comprising PROTONAL® LF 10/60 sodium alginate as the alginate salt typically exhibit inferior adhesion properties when applied to a mucous membrane of the oral cavity. More generally, it is believed that film-forming agents having longer average chain lengths exhibit poorer adhesion to mucosa than film-forming agents having shorter average chain lengths. Without wishing to be bound by any particular theory, it is believed that better mucoadhesion of a film to the mucous membrane of the oral cavity enables a more efficient delivery of any active ingredients contained within the film to their site of action. Therefore, if a long residence time of the film within the oral cavity is not particularly necessary, it may be preferable to use PROTONAL® LFR 5/60 sodium alginate as the alginate salt.

It is particularly preferred that the film comprises PROTONAL® LFR 5/60 sodium alginate as the alginate salt.

The film may also comprise a film-forming agent other than the alginate salt of a monovalent cation or the mixture of alginate salts containing at least one alginate salt of a monovalent cation. Such other film-forming agents include agents such as poly(vinyl pyrrolidone) (PVP), hydroxypropylmethylcellulose (HPMC), pullulan, and so forth. However, if any other film-forming agent is present in the film in addition to the alginate salt of a monovalent cation or the mixture of alginate salts containing at least one alginate salt of a monovalent cation, then typically the alginate salt of a monovalent cation or the mixture of alginate salts containing at least one alginate salt of a monovalent cation will be present in the film in excess over any other film-forming agent present. Preferably, the ratio (by weight) of the alginate salt of a monovalent cation or the mixture of alginate salts containing at least one alginate salt of a monovalent cation present in the film to the combined total of all other film-forming agents (such as PVP, HPMC and/or pullulan)

present in the film is 1:1 or greater, or 2:1 or greater, or 3:1 or greater, or 4:1 or greater, or 5:1 or greater, or 10:1 or greater, or 20:1 or greater, or 50:1 or greater, or 100:1 or greater, or 500:1 or greater, or 1000:1 or greater, or 10000:1 or greater. Preferably, the alginate salt of a monovalent cation or the mixture of alginate salts containing at least one alginate salt of a monovalent cation will constitute at least 50% by weight of the total of the film-forming agents present in the film, more preferably at least 60% by weight, at least 70% by weight, at least 80% by weight, at least 90% by weight, at least 95% by weight, at least 98% by weight, at least 99% by weight, at least 99.5% by weight, at least 99.9% by weight, at least 99.95% by weight, or at least 99.99% by weight of the total of the film-forming agents present in the film.

Preferably, the alginate salt of a monovalent cation or the mixture of alginate salts containing at least one alginate salt of a monovalent cation is substantially the only film-forming agent present in the film. More preferably, the alginate salt of a monovalent cation or the mixture of alginate salts containing at least one alginate salt of a monovalent cation is the only film-forming agent present in the film. Alternatively, the film preferably does not comprise any, or substantially any, poly(vinyl pyrrolidone). Alternatively, the film preferably does not comprise any, or substantially any, pullulan. Alternatively, the film preferably does not comprise any, or substantially any, hydroxypropylmethylcellulose.

As used herein, a reference to a film that does not comprise "substantially any" of a specified component refers to a film that may contain trace amounts of the specified component, provided that the specified component does not materially affect the essential characteristics of the film. Typically, therefore, a film that does not comprise substantially any of a specified component contains less than 5 wt % of the specified component, preferably less than 1 wt % of the specified component, most preferably less than 0.1 wt % of the specified component.

It is a finding of the present invention that the use of an alginate salt of a monovalent cation or a mixture of alginate salts containing at least one alginate salt of a monovalent cation as the film-forming agent has benefits over the use of alternative film-forming agents, such as PVP, HPMC and/or pullulan. In particular, the use of alginate as the primary film-forming agent ensures that the films of the present invention have superior adhesive properties over films comprising primarily other film-forming agents such as PVP, HPMC or pullulan. The films of the present invention are bioadhesive; that is to say that the films of the present invention can firmly adhere to a moist surface (i.e. mucosa) in the oral cavity of a mammal subject before it has fully dissolved. Films in which alginate is not the primary film-forming agent do not generally have this desirable property. A further advantageous finding of the present invention is that the choice of alginate as the primary film-forming agent enables therapeutically effective doses of an active pharmaceutical ingredient (e.g., adrenaline) to be loaded into the films whilst retaining homogeneity and other desirable physical properties of the films.

Without wishing to be bound by any particular theory, it is believed that one of the reasons that alginate is a preferable film-forming agent to, e.g., PVP, HPMC and pullulan, is that the negatively charged alginate salt may act as a counterion to a positively charged amine salt of the compound of Formula (I) (i.e. the API), thus producing a solid, amorphous dispersion during the film manufacture (i.e. enabling the production of clear film with desirable physical characteristics).

Typically, the film comprises from 25% to 99% by weight of the alginate salt of a monovalent cation or the mixture of alginate salts containing at least one alginate salt of a monovalent cation, preferably from 27% to 95% by weight, more preferably from 29% to 93% by weight, still more preferably from 30% to 91% by weight, and most preferably from 35% to 90% by weight.

The film according to the present invention may also contain a residual water content. Typically, the film comprises from 0% to 20% by weight of residual water. More typically, the film comprises from 5% to 15% by weight of residual water. Preferably, the film comprises from 9% to 11% by weight of residual water. Most preferably, the film comprises about 10% by weight of residual water.

The film according to the present invention also comprises an active pharmaceutical ingredient (API) which is a compound of Formula (I) or a pharmaceutically acceptable salt thereof

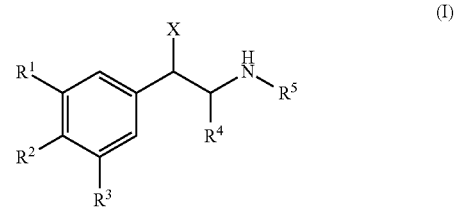

(I)

wherein:
X is selected from hydrogen and OH;
$R^1$ is selected from hydrogen, OH and $CH_2OH$;
$R^2$ and $R^3$ are independently selected from hydrogen and OH;
$R^4$ is selected from hydrogen and methyl; and
$R^5$ is selected from hydrogen and $C_{1-4}$ alkyl.

Thus, $R^2$ is selected from hydrogen and OH. $R^3$ is selected from hydrogen and OH.

Preferably, in the compound of Formula (I), X is OH. Preferably, in the compound of Formula (I), $R^1$ is OH. Preferably, in the compound of Formula (I), $R^2$ is OH. Preferably, in the compound of Formula (I), $R^3$ is hydrogen. Preferably, in the compound of Formula (I), $R^4$ is hydrogen. Preferably, in the compound of Formula (I), $R^5$ is hydrogen or methyl, and is more preferably methyl.

Preferably, the compound of Formula (I) is selected from the group consisting of adrenaline, noradrenaline, ephedrine, pseudoephedrine, amphetamine, salbutamol, terbutaline, orciprenaline, isoprenaline and tyramine.

More preferably, the compound of Formula (I) is adrenaline. The structure of adrenaline is provided below as Formula (III).

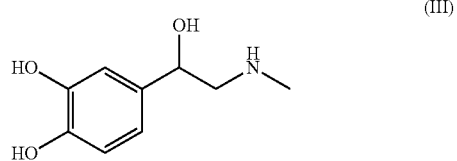

(III)

The compounds of Formula (I) may contain one or more stereogenic centres. For example, when substituent X in Formula (I) is OH, the carbon atom to which X is bonded is a stereogenic centre. Similarly, when substituent $R^4$ in Formula (I) is methyl, the carbon atom to which $R^4$ is bonded is a stereogenic centre. Certain compounds of Formula (I) may therefore be isolated in optically active or racemic forms. It is well-known in the art how to prepare optically active forms, such as by resolution of materials. For the avoidance of doubt, Formula (I) encompasses all enantiomeric, diastereomeric, and racemic forms of the compounds thereof, as well as all mixtures of enantiomers and diastereomers of the compounds thereof.

Thus, for example, when the compound of Formula (I) is adrenaline, this means that the compound of Formula (I) may be (+)-adrenaline, (−)-adrenaline, or a mixture of (+)-adrenaline and (−)-adrenaline.

Most preferably, the compound of Formula (I) is (−)-adrenaline. The structure of (−)-adrenaline is provided below as Formula (IV).

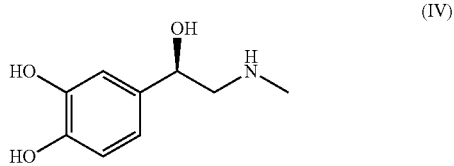

(IV)

Adrenaline may also be referred to as epinephrine. For the avoidance of doubt, as used herein, the terms "adrenaline" and "epinephrine" are interchangeable. (−)-Adrenaline may also be referred to as (−)-epinephrine, L-adrenaline, L-epinephrine, L-(−)-adrenaline, L-(−)-epinephrine or (R)-(−)-3,4-Dihydroxy-α-(methylaminomethyl)benzyl alcohol. For the avoidance of doubt, as used herein, these terms are therefore interchangeable.

The API may be a pharmaceutically acceptable polymorph, co-crystal, hydrate or solvate of the compound of Formula (I) or pharmaceutically acceptable salt thereof, preferably a pharmaceutically acceptable polymorph, co-crystal, hydrate or solvate of adrenaline or a pharmaceutically acceptable salt thereof, more preferably a pharmaceutically acceptable polymorph, co-crystal, hydrate or solvate of (−)-adrenaline or a pharmaceutically acceptable salt thereof.

Alternatively, the API may be a prodrug of a compound of Formula (I) or a pharmaceutically acceptable salt thereof, preferably a prodrug of adrenaline, more preferably a prodrug of (−)-adrenaline. The term "prodrug" of a compound of Formula (I), as used herein, refers to any compound or pharmaceutically acceptable salt thereof which, after administration to the human body, may be metabolised in vivo to a compound of Formula (I). Typical prodrugs include acyl, ester, alkoxycarbonyl and carbamate derivatives of the compound of Formula (I). For example, prodrugs of adrenaline include dipivefrine.

Thus, the API may be a compound of Formula (V)

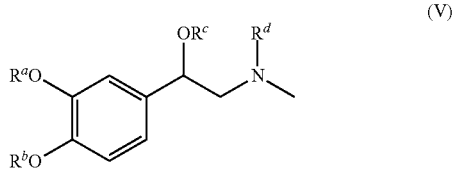

(V)

wherein:

$R^a$, $R^b$ and $R^c$ are independently hydrogen or a bio-labile linker, such as acyl, alkoxycarbonyl, carbamate, phosphate, diphosphate, or triphosphate; and $R^d$ is hydrogen or a bio-labile linker, such as acyl, alkoxycarbonyl or carbamate; provided that not all of $R^a$, $R^b$, $R^c$ and $R^d$ are hydrogen.

Thus, $R^a$ is hydrogen or a bio-labile linker, such as acyl, alkoxycarbonyl, carbamate, phosphate, diphosphate, or triphosphate. $R^b$ is hydrogen or a bio-labile linker, such as acyl, alkoxycarbonyl, carbamate, phosphate, diphosphate, or triphosphate. $R^c$ is hydrogen or a bio-labile linker, such as acyl, alkoxycarbonyl, carbamate, phosphate, diphosphate, or triphosphate.

Preferably, when the API is a compound of Formula (V), $R^c$ and $R^d$ are hydrogen.

Typically, the API is a pharmaceutically acceptable salt of the compound of Formula (I). Typically, the pharmaceutically acceptable salt of the compound of Formula (I) is selected from the group consisting of acetate, propionate, isobutyrate, benzoate, succinate, suberate, tartrate, citrate, fumarate, malonate, maleate, adipate, di-mesylate, sulfate, benzenesulfonate, nitrate, carbonate, hydrochloride, hydrobromide, phosphate, aluminium, ammonium, calcium, copper, ferric, ferrous, lithium, magnesium, manganic, manganous, potassium, sodium, zinc, arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine and tromethamine salts of the compound of Formula (I). Preferred salt forms of the compound of Formula (I) include acetate, propionate, isobutyrate, benzoate, succinate, suberate, tartrate, citrate, fumarate, malonate, maleate, adipate, di-mesylate, sulfate, benzenesulfonate, nitrate, carbonate, hydrochloride, hydrobromide, and phosphate salts of the compound of Formula (I). More preferred salt forms of the compound of Formula (I) include tartaric acid salts, dicarboxylic acid salts, hydrochloric acid salts, phosphoric acid salts, sulfuric acid salts or benzenesulfonic acid salts of the compound of Formula (I).

As defined herein, the term "compound of Formula (I)" refers to the form of the compound of Formula (I) in which the molecules are present in neutral (i.e. unionized) form. The term "pharmaceutically acceptable salt of the compound of Formula (I)" refers to any salt of the compound of Formula (I). For example, when the compound of Formula (I) is adrenaline, the term "pharmaceutically acceptable salt of adrenaline" refers to any salt of adrenaline in which the secondary amine group of adrenaline is protonated, or in which one or both of the hydroxyl (phenolic) groups in adrenaline are deprotonated. Preferably, the term "pharmaceutically acceptable salt of adrenaline" refers to any salt of adrenaline in which the secondary amine group is protonated.

Typically, the API is a pharmaceutically acceptable salt of adrenaline selected from the group consisting of acetate, propionate, isobutyrate, benzoate, succinate, suberate, tartrate, citrate, fumarate, malonate, maleate, adipate, di-mesylate, sulfate, benzenesulfonate, nitrate, carbonate, hydrochloride, hydrobromide, and phosphate salts of adrenaline. Preferred salt forms of adrenaline include dicarboxylic acid salts, hydrochloric acid salts, phosphoric acid salts, sulfuric acid salts, benzenesulfonic acid salts or tartaric acid salts of adrenaline. More preferably, the pharmaceutically acceptable salt of adrenaline is a dicarboxylic acid salt or tartaric acid salt of adrenaline, most preferably a tartaric acid salt of adrenaline.

Typically, the API is a pharmaceutically acceptable salt of (−)-adrenaline selected from the group consisting of acetate, propionate, isobutyrate, benzoate, succinate, suberate, tartrate, citrate, fumarate, malonate, maleate, adipate, di-mesylate, sulfate, benzenesulfonate, nitrate, carbonate, hydrochloride, hydrobromide, and phosphate salts of (−)-adrenaline. Preferred salt forms of (−)-adrenaline include dicarboxylic acid salts, hydrochloric acid salts, phosphoric acid salts, sulfuric acid salts, benzenesulfonic acid salts or tartaric acid salts of (−)-adrenaline. More preferably, the pharmaceutically acceptable salt of (−)-adrenaline is a dicarboxylic acid salt or tartaric acid salt of (−)-adrenaline, most preferably a tartaric acid salt of (−)-adrenaline.

Typically, the API is a pharmaceutically acceptable salt of a racemic mixture of (−)-adrenaline and (+)-adrenaline selected from the group consisting of acetate, propionate, isobutyrate, benzoate, succinate, suberate, tartrate, citrate, fumarate, malonate, maleate, adipate, di-mesylate, sulfate, benzenesulfonate, nitrate, carbonate, hydrochloride, hydrobromide, and phosphate salts of a racemic mixture of (−)-adrenaline and (+)-adrenaline. Preferred salt forms of the racemic mixture of (−)-adrenaline and (+)-adrenaline include dicarboxylic acid salts, hydrochloric acid salts, phosphoric acid salts, sulfuric acid salts, benzenesulfonic acid salts or tartaric acid salts of the racemic mixture of (−)-adrenaline and (+)-adrenaline. More preferably, the pharmaceutically acceptable salt of the racemic mixture of (−)-adrenaline and (+)-adrenaline is a dicarboxylic acid salt or tartaric acid salt of the racemic mixture of (−)-adrenaline and (+)-adrenaline, most preferably a tartaric acid salt of the racemic mixture of (−)-adrenaline and (+)-adrenaline.

The API may be present within the film in varying amounts. Typically, the film comprises from 0.001% to 75% by weight of the API, preferably from 0.01% to 60% by weight of the API, more preferably from 0.15% to 50% by weight of the API, still more preferably from 0.2% to 45% by weight of the API and most preferably from 0.25% to 40% by weight of the API.

Typically, the compound of Formula (I) or pharmaceutically acceptable salt thereof is the only API present in the film. However, the film may alternatively comprise one or more further active pharmaceutical ingredients in addition to the compound of Formula (I) or pharmaceutically acceptable salt thereof.

Preferably, the film comprises from 25% to 99% by weight of the alginate salt of a monovalent cation or the mixture of alginate salts containing at least one alginate salt of a monovalent cation, from 0% to 20% by weight of water, and from 0.001% to 75% by weight of the API. More preferably, the film comprises from 29% to 93% by weight of the alginate salt of a monovalent cation or the mixture of alginate salts containing at least one alginate salt of a monovalent cation, from 5% to 15% by weight of water, and from 0.15% to 50% by weight of the API. Even more preferably, the film comprises from 30% to 91% by weight of the alginate salt of a monovalent cation or the mixture of alginate salts containing at least one alginate salt of a monovalent cation, from 9% to 11% by weight of water, and from 0.2% to 45% by weight of the API.

A film according to the present invention may optionally further comprise other components in addition to the API, water and the film-forming agent. Typically, a film according to the present invention further comprises one or more of the following:
- (i) at least one antioxidant;
- (ii) at least one pharmaceutically acceptable solvent;
- (iii) at least one buffering component;
- (iv) at least one excipient, such as one or more plasticizers, fillers, taste-masking agents or flavouring agents;
- (v) at least one acidifying agent or basifying agent;
- (vi) at least one permeation enhancer;
- (vii) a self-emulsifying drug delivery system (SEDDS), such as a self-microemulsifying drug delivery system (SMEDDS) or a self-nanoemulsifying drug delivery system (SNEDDS);
- (viii) at least one chelating agent;
- (ix) at least one antimicrobial agent; and
- (x) at least one inorganic salt.

The film may additionally comprise any suitable antioxidant. An "antioxidant", as defined herein, is any compound that inhibits the oxidation of other chemical species. Examples of suitable antioxidants include, but are not limited to: ascorbic acid; citric acid; sodium bisulfite; sodium metabisulfite; ethylenediaminetetraacetic acid (EDTA); butyl hydroxitoluene; and combinations thereof. Preferably, the antioxidant, if present, is ascorbic acid, sodium bisulfite, sodium metabisulfite, EDTA or a combination thereof. Thus, typically, at least one antioxidant is present in the films of the present invention. Preferably, the film comprises at least two antioxidants. More preferably, the film comprises at least three antioxidants. Most preferably, said antioxidants are selected from ascorbic acid, citric acid, sodium bisulfite, sodium metabisulfite, EDTA and butyl hydroxytoluene.

More preferably, the antioxidant, if present, is ascorbic acid. Yet more preferably, both ascorbic acid and sodium bisulfite are present as antioxidants. Alternatively, both ascorbic acid and sodium metabisulfite are present as antioxidants. Even more preferably, all of ascorbic acid, sodium bisulfite and EDTA are present as antioxidants. Alternatively, all of ascorbic acid, sodium metabisulfite and EDTA are present as antioxidants.

Thus, in a particularly preferred film of the present invention, the film comprises (i) ascorbic acid and (ii) sodium bisulfite or sodium metabisulfite. Alternatively, the film may comprise (i) ascorbic acid and (ii) EDTA. Alternatively, the film may comprise (i) sodium bisulfite or sodium metabisulfite and (ii) EDTA. In even more preferred films of the present invention, the films comprises (i) ascorbic acid, (ii) sodium bisulfite or sodium metabisulfite, and (iii) EDTA.

The film may comprise from 0.01% to 10% by weight of each antioxidant present. Preferably, the film may comprise from 0.1% to 8% by weight of each antioxidant present, more preferably from 0.25% to 6% by weight of each antioxidant present, and yet more preferably from 0.5% to 5% by weight of each antioxidant present. The ratio of total antioxidants present in the film to API present in the film (by weight) is typically from 0.01:1 to 10:1, preferably from 0.05:1 to 10:1, more preferably from 0.1:1 to 10:1, yet more preferably from 0.25:1 to 10:1, still more preferably from 0.5:1 to 10:1, even more preferably from 1:1 to 3:1, and most preferably about 2:1. The ratio of total antioxidants present in the film to API present in the film (by molar amounts) is typically from 0.01:1 to 5:1, preferably from 0.02:1 to 2:1, more preferably from 0.03:1 to 1:1, yet more preferably from 0.05:1 to 0.5:1, even more preferably from 0.08:1 to 0.3:1, and most preferably from 0.1:1 to 0.2:1.

If ascorbic acid is present as an antioxidant, typically it is present in a molar amount of from 0.0005 to 0.5 per mole of API present in the film, preferably of from 0.001 to 0.1, more preferably of from 0.005 to 0.05, yet more preferably of from 0.008 to 0.02, and most preferably of 0.01 or less.

If sodium bisulfite or sodium metabisulfite is present as an antioxidant, typically it is present in a molar amount of from 0.001 to 1.0 per mole of API present in the film, preferably of from 0.005 to 0.5, more preferably of from 0.01 to 0.2, yet more preferably of from 0.025 to 0.1, and most preferably of about 0.05.

If EDTA is present as an antioxidant, typically it is present in a molar amount of from 0.001 to 1.0 per mole of API present in the film, preferably of from 0.005 to 0.5, more preferably of from 0.01 to 0.3, yet more preferably of from 0.02 to 0.2, and most preferably of 0.03 or greater. If EDTA is present as an antioxidant, typically it is present in the film in an amount by weight of from 0.01% to 5%, preferably from 0.03% to 1%, more preferably from 0.06% to 0.5%, and most preferably from 0.12% to 0.25%.

The film may additionally comprise any pharmaceutically acceptable solvent. Such a solvent may be a non-aqueous solvent, or a combination of water and a non-aqueous solvent. Examples of non-aqueous solvents should be non-toxic and include, but are not limited to, ethanol, acetone, benzyl alcohol, diethylene glycol monoethyl ether, glycerine, hexylene glycol, isopropyl alcohol, polyethylene glycols, methoxypolyethylene glycols, diethyl sebacate, dimethyl isosorbide, propylene carbonate, dimethyl sulfoxide, transcutol, triacetin, fatty acid esters, and oils such as soybean oil, peanut oil, olive oil, palm oil, rapeseed oil, corn oil, coconut oil, other vegetable oils and the like.

The film may additionally comprise any suitable buffering component. A "buffering component", as defined herein, refers to any chemical entity, which when dissolved in solution, enables said solution to resist changes in its pH following the subsequent addition of either an acid or a base. A suitable buffering component for use in the film of the present invention would be a buffering component which is an effective buffer within a pH range of from 3.0 to 5.5. Preferably, said buffering component is an effective buffer within a pH range of from 3.8 to 5.5. Examples of suitable buffering components include, but are not limited to: phosphates, sulfates, citrates and acetates. The buffer may be a salt of a monovalent cation, such as sodium, potassium or ammonium salts. Particularly preferred buffering components include citric acid and sodium dihydrogen phosphate. Without wishing to be bound by any particular theory, it is believed that adrenaline has a low stability towards oxidation at a pH of greater than 5.5. Further, without wishing to be bound by any particular theory, it is believed that alginate tends to gel at a pH of less than 3.8.

The film may comprise from 0.1% to 10% by weight of the buffering component, typically 0.2% to 8% by weight, typically from 0.3% to 6% by weight, typically from 0.5% to 5% by weight. Alternatively, the film may not additionally comprise a buffering component.

The film may additionally comprise any suitable excipient, such as one or more fillers or plasticizers. The film may comprise both a plasticizer and a filler. Alternatively, the film may comprise just one of a plasticizer or a filler. It is preferred that the film comprises a plasticizer. Under some circumstances it may be desirable that the film does not comprise a filler. It is particularly preferred that the film comprises a plasticizer but does not comprise a filler. The film may additionally include a taste-masking agent or a flavouring agent. The taste-masking agent may be a sweetener.

The plasticizer, when present, may be selected from the group consisting of polyethylene glycol, glycerol, sorbitol, xylitol, and a combination thereof. Typically, the film comprises a plasticizer which is selected from the group consisting of glycerol, sorbitol, xylitol, and a combination thereof. Preferably, the film comprises a plasticizer which is selected from the group consisting of glycerol, sorbitol, and a combination thereof. More preferably, the film comprises both glycerol and sorbitol as plasticizers. Most preferably, the film comprises glycerol, sorbitol and xylitol. The film may comprise from 0% to 40% by weight of each plasticizer present, preferably from 1% to 35% by weight of each plasticizer, more preferably from 2% to 30% by weight of each plasticizer, and most preferably from 3% to 25% by weight of each plasticizer. Without wishing to be bound by any particular theory, it is believed that the addition of plasticizers, e.g. a combination of glycerol, sorbitol and xylitol, increases the flexibility and pliability of the films, reducing brittleness. It is believed this makes the films easier to handle and use.

The filler, when present, may be e.g. microcrystalline cellulose or titanium dioxide. A suitable amount of filler may be from 0% to 20% by weight, e.g. from 0.1% to 10% by weight, of the total pharmaceutical composition.

The flavouring agent, when present, may for example be selected from the group consisting of acacia, anise oil, caraway oil, cardamom, cherry syrup, cinnamon, citric acid syrup, clove oil, cocoa, coriander oil, ethyl vanillin, fennel oil, ginger, glycerine, glycyrrhiza, honey, lavender oil, lemon oil, mannitol, nutmeg oil, orange oil, orange flower water, peppermint oil, raspberry, rose oil, rosewater, rosemary oil, sarsaparilla syrup, spearmint oil, thyme oil, tolu balsam syrup, vanilla, wild cherry syrup, and mixtures thereof. The film may comprise from 0.001% to 10% by weight of each flavouring agent present, preferably from 0.01% to 5% by weight of each flavouring agent, and most preferably from 0.1% to 3% by weight of each flavouring agent.

The film may additionally comprise an acidifying agent or a basifying agent. An "acidifying agent", as defined herein, refers to a chemical compound that alone or in combination with other compounds can be used to acidify a pharmaceutical composition. A "basifying agent", as defined herein, refers to a chemical compound that alone or in combination with other compounds can be used to basify a pharmaceutical composition.

Typically, the film comprises an basifying agent. Typically, the basifying agent is an alkali. Examples of suitable basifying agents include, but are not limited to: sodium hydroxide, lithium hydroxide, potassium hydroxide, magnesium hydroxide, and calcium hydroxide. A preferable basifying agent is sodium hydroxide. Alternatively, the film may comprise an acidifying agent. Examples of suitable acidifying agents include, but are not limited to: acetic acid, dehydro acetic acid, ascorbic acid, benzoic acid, boric acid, citric acid, edetic acid, hydrochloric acid, isostearic acid, lactic acid, nitric acid, oleic acid, phosphoric acid, sorbic acid, stearic acid, sulfuric acid, tartaric acid, and undecylenic acid. A preferable acidifying agent is phosphoric acid.

A film according to the present invention is produced via the drying of a film-forming solution (vide infra). Typically, a sufficient amount of acidifying agent or basifying agent is added to adjust the pH of the film-forming solution (before this is dried to form the film) to a pH of from 3.0 to 5.5, preferably to a pH of from 3.8 to 5.5.

The film may additionally comprise any suitable permeation enhancer. A "permeation enhancer", as defined herein, refers to a chemical compound that alone or in combination with other compounds can be used to aid the uptake of a further substance across an epithelium or other biological membrane. In particular, the term "permeation enhancer" is used herein to refer to a chemical compound that alone or in combination with other compounds can be used to aid the uptake of a further substance across the buccal mucosa. Permeation enhancers can typically be divided into two different categories, paracellular (para) or transcellular (trans) permeability enhancers, according to their mechanism of action. Paracellular permeation enhancers are those which aid the uptake of a further substance through the intercellular space between the cells in an epithelium or other biological membrane. Transcellular permeation enhancers are those which aid the uptake of a further substance through the cells in an epithelium or other biological membrane, wherein the further substance passes through both the apical and basolateral cell membranes in the epithelium or other biological membrane.

Typically, the film may comprise one or more paracellular permeation enhancers. Alternatively, the film may comprise one or more transcellular permeation enhancers. Alternatively, the film may comprise at least one paracellular permeation enhancer and at least one transcellular permeation enhancer.

Typically, the permeation enhancer, if present, is one or more compounds selected from the group consisting of: non-ionic, cationic, anionic or zwitterionic surfactants (e.g. caprylocaproyl polyoxyl-8 glyceride, sodium lauryl sulfate, cetyltrimetyl ammonium bromide, decyldimethyl ammonio propane sulfonate); bile salts (e.g. sodium deoxycholate); fatty acids (e.g. hexanoic acid, hetptanoic acid, oleic acid); fatty amines; fatty ureas; fatty acid esters (e.g. methyl laurate, methyl palmitate); substituted or unsubstituted nitrogen-containing heterocyclic compounds (e.g. methyl pyrrolidone, methyl piperazine, azone); terpenes (e.g. limonene, fenchone, menthone, cineole); sulfoxides (e.g. dimethylsulfoxide, DMSO); ethylenediaminetetraacetic acid (EDTA); and combinations thereof. Preferably, the permeation enhancer, if present, is selected from the group consisting of EDTA, oleic acid, and combinations thereof.

Typically, the film may comprise EDTA. Without wishing to be bound by any particular theory, EDTA is believed to act as a paracellular permeation enhancer by transiently affecting tight junctions interconnecting membrane cells, and subsequently increasing paracellular or pore transport. EDTA is also believed to act as a transcellular permeation enhancer by interaction with phospholipid headgroups and increasing membrane fluidity [5]. Alternatively, the film may comprise oleic acid. Without wishing to be bound by any particular theory, oleic acid is believed to act as a transcellular permeation enhancer by interacting with the polar head groups of phospholipids in or on cell membranes, and increasing cell membrane flexibility, thereby promoting transcellular drug permeability. Oleic acid has been shown to demonstrate enhanced permeability with porcine buccal epithelium at a concentration of 1-10% [6].

The film may additionally comprise a self-emulsifying drug delivery system (SEDDS) or resulting emulsion thereof. Such a system may preferably be a self-microemulsifying drug delivery system (SMEDDS) or resulting emulsion thereof or a self-nanoemulsifying drug delivery system (SNEDDS) or resulting emulsion thereof. Self-microemulsifying drug delivery systems are microemulsion preconcentrates or anhydrous forms of microemulsion. Self-nanoemulsifying drug delivery systems are nanoemulsion preconcentrates or anhydrous forms of nanoemulsion. These systems are typically anhydrous isotropic mixtures of oil (e.g. tri-, di- or mono-glycerides or mixtures thereof) and at least one surfactant (e.g. SPAN® (sorbitan monooleate), TWEEN® (polysorbate)), which, when introduced into aqueous phase under conditions of gentle agitation, spontaneously form an oil-in-water (O/W) microemulsion or nanoemulsion (respectively). SNEDDS systems typically form an emulsion with a globule size less than 200 nm [7]. SEDDS (e.g. SMEDDS or SNEDDS) may also contain coemulsifier or cosurfactant and/or solubilizer in order to facilitate emulsification (e.g. micoremulsification or nanoemulsification) or improve the drug incorporation into the SEDDS (e.g. SMEDDS or SNEDDS). Typically, the SEDDS (e.g. SMEDDS or SNEDDS) components is selected from the group consisting of: a mixture of TWEEN® (polysorbate) with one or more glycerides and a hydrophilic cosolvent; a mixture of TWEEN® (polysorbate) with a low HLB cosurfactant and a hydrophilic cosolvent; a mixture of a polyethyleneglycol (PEG), Labrasol and Chremophore EL; a mixture of polyethyleneglycol (PEG), Labrasol and Kolliphore EL; and a mixture of polyethyleneglycol (PEG), Labrasol, Chremophore EL and Chremophore RH40. The PEG may be any suitable polyethyleneglycol such as PEG with an average molecular weight of from 100 to >1000 Da, preferably from 200 to 800 Da, more preferably from 300 to 600 Da, and most preferably about 400.

The term "glyceride", as defined herein, refers to any ester formed between glycerol and one or more fatty acids. The term "glyceride" may be used interchangeably with the term "acylglycerol". Typically, the glyceride is a monoglyceride, a diglyceride or a triglyceride. Preferably, the glyceride is a triglyceride. Typically, the glyceride is a simple glyceride. The term "simple glyceride" refers to a diglyceride in which the two fatty acids are the same as one another, or a triglyceride in which the three fatty acids are the same as one another. Alternatively, the glyceride is a mixed glyceride. The term "mixed glyceride" refers to a diglyceride in which the two fatty acids are different one another, or a triglyceride in which either one of the three fatty acids is different to the other two, or all three of the fatty acids are different to one another. Therefore, the glyceride is typically a monoglyceride, a simple diglyceride, a simple triglyceride, a mixed diglyceride, or a mixed triglyceride. Preferably, the glyceride is a simple triglyceride or a mixed triglyceride.

A "hydrophilic cosolvent", as defined herein, is any solvent that is miscible with water. Examples of suitable hydrophilic cosolvents include, but are not limited to: glycerol, ethanol, 2-(2-ethoxyethoxyethanol), PEG-400 and propylene glycol.

The term "low HLB cosurfactant", as defined herein, refers to any lipid falling within class IIIA, IIIB or IV of the lipid formulation classification system described by C. W. Pouton [8].

Typically, the film may additionally comprise any suitable chelating agent. A chelating agent may be added to the film to act as a preservative. A "chelating agent", as defined herein, refers to a chemical compound that is a multidentate ligand that is capable of forming two or more separate bonds to a single central atom, typically a metal ion. Examples of suitable chelating agents include, but are not limited to: ethylenediaminetetraacetic acid (EDTA), ethylene glycol-bis(3-aminoethyl ether)-N,N,N',N'-tetraacetic acid (EGTA), 1,2-bis(ortho-aminophenoxy)ethane-N,N,N',N'-tetraacetic acid (BAPTA), citric acid, phosphonic acid, glutamic acid, histidine, malate, and derivatives thereof. Preferably, the chelating agent, if present, is ethylenediaminetetraacetic acid (EDTA). The film may comprise from 0.001% to 4% by weight of each chelating agent present. Preferably, the film may comprise from 0.001% to 0.1% by weight of each chelating agent present.

Typically, the film may additionally comprise any suitable antimicrobial agent. An "antimicrobial agent", as defined herein, is any compound that kills microorganisms or prevents their growth. Examples of suitable antimicrobial agents include, but are not limited to: benzyl alcohol; benzalkonium chloride; benzoic acid; methyl-, ethyl- or propyl-paraben; and quarternary ammonium compounds. The film may comprise from 0.001% to 4% by weight of each antimicrobial agent present. Preferably, the film may comprise from 0.001% to 0.1% by weight of each antimicrobial agent present.

EDTA may therefore be present in a film according to the present invention as an antioxidant, as a permeation enhancer or as a chelating agent. Typically, if EDTA is present, the EDTA acts as all of an antioxidant, a permeation enhancer and a chelating agent. Alternatively, if EDTA is present, the EDTA may act only as an antioxidant. Alternatively, if EDTA is present, the EDTA may act only as a permeation enhancer. Alternatively, if EDTA is present, the EDTA may act only as a chelating agent.

Optionally, the film may additionally comprise at least one inorganic salt. Said inorganic salt may be any salt acceptable for use in the preparation of a medicament. Examples of such salts include, but are not limited to, the halides, oxides, hydroxides, sulfates, carbonates, phosphates, nitrates, acetates and oxamates of the alkali metals, alkaline earth metals, aluminium, zinc and ammonium. Typically, said inorganic salt may be selected from the group consisting of sodium chloride, potassium chloride, magnesium chloride, calcium chloride, and ammonium chloride. Preferably, the inorganic salt is sodium chloride. Typically, the inorganic salt is present in the film in a total concentration of at least 0.05 wt %, preferably in a concentration of from 0.1 to 5 wt %, more preferably from 0.2 to 2 wt %, yet more preferably from 0.25 to 1 wt %, and most preferably about 0.5 wt %. Alternatively, the film does not comprise any inorganic salt. In such an embodiment, the film typically comprises the neutral (i.e. unionized) form of the API.

Typically, the film may additionally comprise at least one antioxidant, at least one excipient, optionally at least one basifying agent or acidifying agent, optionally at least one permeation enhancer, optionally at least one pharmaceutically acceptable solvent, optionally at least one buffering component, and optionally a SEDDS (e.g. SMEDDS or SNEDDS). For example, the film may comprise at least one antioxidant, at least one excipient, optionally at least one basifying agent or acidifying agent, optionally at least one permeation enhancer, and optionally at least one buffering component. Preferably, the film may comprise at least one antioxidant, glycerol, sorbitol, optionally at least one basifying agent or acidifying agent, optionally at least one permeation enhancer, and optionally at least one buffering component. More preferably, the film may comprise at least one antioxidant, glycerol, sorbitol, and optionally at least one basifying agent. Even more preferably, the film may comprise: an antioxidant selected from ascorbic acid, sodium bisulfite and a combination thereof; glycerol; sorbitol; and optionally at least one basifying agent, preferably sodium hydroxide. Still more preferably, the film may comprise: ascorbic acid; glycerol; sorbitol; and optionally at least one basifying agent, preferably sodium hydroxide. Most preferably, the film may comprise: ascorbic acid; sodium bisulfite; glycerol; sorbitol; and optionally at least one basifying agent, preferably sodium hydroxide.

Preferably, the film according to the present invention comprises from 25% to 99% by weight of the alginate salt of a monovalent cation or the mixture of alginate salts containing at least one alginate salt of a monovalent cation, from 0% to 20% by weight of water, from 0.001% to 75% by weight of the API, from 0.01% to 10% by weight of at least one antioxidant, from 0% to 40% by weight of glycerol, from 0% to 40% by weight of sorbitol, optionally from 0% to 40% by weight of xylitol, optionally a basifying agent or an acidifying agent, optionally from 0.01% to 5% by weight of a permeation enhancer, optionally from 0.1% to 10% by weight of a SEDDS (e.g. SMEDDS or SNEDDS), and optionally from 0.001% to 4% by weight of a chelating agent. More preferably, the film according to the present invention comprises from 30% to 91% by weight of the alginate salt of a monovalent cation or the mixture of alginate salts containing at least one alginate salt of a monovalent cation, from 9% to 11% by weight of water, from 0.2% to 45% by weight of the API, from 0.01% to 10% by weight of at least one antioxidant, from 10% to 20% by weight of glycerol, from 10% to 20% by weight of sorbitol, optionally from 10% to 20% by weight of xylitol, and optionally a basifying agent or an acidifying agent, and wherein the ratio of total antioxidants present in the film to API present in the film (by weight) is from 0.5:1 to 10:1.

Alternatively, the film according to the present invention consists of from 25% to 99% by weight of the alginate salt of a monovalent cation or the mixture of alginate salts containing at least one alginate salt of a monovalent cation, from 0% to 20% by weight of water, from 0.001% to 75% by weight of the API, from 0.1% to 10% by weight of at least one antioxidant, from 0% to 40% by weight of glycerol, from 0% to 40% by weight of sorbitol, optionally from 0% to 40% by weight of xylitol, optionally a basifying agent or an acidifying agent, optionally from 0.01% to 5% by weight of a permeation enhancer, optionally from 0.1% to 10% by weight of a SEDDS (e.g. SMEDDS or SNEDDS), and optionally from 0.001% to 4% by weight of a chelating agent. Alternatively, the film according to the present invention consists of from 30% to 91% by weight of the alginate salt of a monovalent cation or the mixture of alginate salts containing at least one alginate salt of a monovalent cation, from 9% to 11% by weight of water, from 0.2% to 45% by weight of the API, from 0.1% to 10% by weight of at least one antioxidant, from 10% to 20% by weight of glycerol, from 10% to 20% by weight of sorbitol, optionally from 10% to 20% by weight of xylitol, and optionally a basifying agent or an acidifying agent, and wherein the ratio of total antioxidants present in the film to API present in the film (by weight) is from 0.5:1 to 10:1.

A film according to the invention preferably has a thickness before drying of 200 to 2000 μm, more preferably from 300 to 1750 μm, even more preferably from 400 to 1500 μm, and most preferably about 1000 μm.

A film according to the invention preferably has a surface area on each of its two largest faces of from 0.1 to 20 cm$^2$, more preferably from 0.5 to 15 cm$^2$, even more preferably from 1 to 10 cm$^2$ and most preferably from 2 to 6 cm$^2$. Preferably, the surface area of each of the two largest faces of the film is about 3 cm$^2$.

The skilled person, having regard for the desired time of dissolution for a given application, will be able to select a suitable film thickness and surface area by simply preparing films of a range of different thicknesses and surface areas and testing the resultant films to measure the dissolution time.

The mechanical properties of a film according to the invention are very satisfactory. In particular, the film is flexible (i.e. it permits bending and folding without breaking), and has a high tensile strength. Importantly, the film of the present invention is not a gel, since the alginate polymer strands are not cross-linked with one another. The film of the invention is bioadhesive; that is to say that the film comprises a natural polymeric material (alginate) which can act as an adhesive. The film is adhesive to moist surfaces, such as mucosa. In particular, the film is adhesive to mucosa of the oral cavity, such as mucosa in the buccal, labial, sublingual, ginigival or lip areas, the soft palate and the hard palate.

The film according to the invention may be provided with printed text matter or printed images thereon, e.g. a brand name, a trade mark, a dosage indication or a symbol.

Administration and Uses of the Films in Treatment

In general, films of the present invention are administered to a human patients so as to deliver to the patient a therapeutically effective amount of the active pharmaceutical ingredient (API), preferably (−)-adrenaline or a pharmaceutically acceptable salt thereof, contained therein.

As used herein, the term "therapeutically effective amount" refers to an amount of the API which is sufficient to reduce or ameliorate the severity, duration, progression, or onset of a disorder being treated, prevent the advancement of a disorder being treated, cause the regression of, prevent the recurrence, development, onset or progression of a symptom associated with a disorder being treated, or enhance or improve the prophylactic or therapeutic effect(s) of another therapy. The precise amount of API administered to a patient will depend on the type and severity of the disease or condition and on the characteristics of the patient, such as general health, age, sex, body weight and tolerance to drugs. It will also depend on the degree, severity and type of the disorder being treated. The skilled artisan will be able to determine appropriate dosages depending on these and other factors.

As used herein, the terms "treat", "treatment" and "treating" refer to the reduction or amelioration of the progression, severity and/or duration of a disorder being treated, or the amelioration of one or more symptoms (preferably, one or more discernible symptoms) of a disorder being treated resulting from the administration of a film according to the invention to a patient.

Typically, a film according to the present invention is provided for use in the treatment of a human patient. Typically, the film according to the invention is provided for use in the treatment of a condition selected from the group consisting of anaphylaxis, superficial bleeding, cardiac arrest, hypotension, septic shock, neurogenic shock, asthma, narcolepsy, obesity, nasal congestion, sinus congestion, Eustachian tube congestion, vasomotor rhinitis, allergic rhinitis, croup, sinusitis, otitis media, tracheobronchitis, hyperemia, edema, priapism, attention deficit hyperactivity disorder (ADHD), depression, chronic pain, bronchoconstriction, chronic obstructive pulmonary disease (COPD), hyperkalemia, preterm labour, bradycardia, and heart block.

Typically, the compound of Formula (I) is adrenaline and the film according to the invention is provided for use in the treatment of a condition selected from the group consisting of anaphylaxis, superficial bleeding, and cardiac arrest.

Alternatively, the compound of Formula (I) is noradrenaline and the film according to the invention is provided for use in the treatment of a condition selected from the group consisting of hypotension, septic shock, and neurogenic shock.

Alternatively, the compound of Formula (I) is ephedrine and the film according to the invention is provided for use in the treatment of a condition selected from the group consisting of hypotension, asthma, narcolepsy, obesity, and nasal congestion.

Alternatively, the compound of Formula (I) is pseudoephedrine and the film according to the invention is provided for use in the treatment of a condition selected from the group consisting of nasal congestion, sinus congestion, Eustachian tube congestion, vasomotor rhinitis, allergic rhinitis, croup, sinusitis, otitis media, tracheobronchitis, hyperemia, edema, and priapism.

Alternatively, the compound of Formula (I) is amphetamine and the film according to the invention is provided for use in the treatment of a condition selected from the group consisting of attention deficit hyperactivity disorder (ADHD), narcolepsy, obesity, depression, and chronic pain.

Alternatively, the compound of Formula (I) is salbutamol and the film according to the invention is provided for use in the treatment of a condition selected from the group consisting of asthma, bronchoconstriction, chronic obstructive pulmonary disease (COPD), and hyperkalemia.

Alternatively, the compound of Formula (I) is terbutaline and the film according to the invention is provided for use in the treatment of a condition selected from the group consisting of asthma, bronchoconstriction, and preterm labour.

Alternatively, the compound of Formula (I) is orciprenaline and the film according to the invention is provided for use in the treatment of a condition selected from the group consisting of asthma and bronchoconstriction.

Alternatively, the compound of Formula (I) is isoprenaline and the film according to the invention is provided for use in the treatment of a condition selected from the group consisting of bradycardia, heart block, and asthma.

Preferably, the film according to the invention is provided for use in the treatment of anaphylaxis, superficial bleeding and/or cardiac arrest. Typically, therefore, the film according to the invention is provided for use in the treatment of anaphylaxis. Alternatively, the film according to the invention is provided for use in the treatment of superficial bleeding. Alternatively, the film according to the invention is provided for use in the treatment of cardiac arrest.

The present invention provides a film according to the invention for use in the treatment of anaphylaxis. The effects of anaphylaxis in a patient may be severe. The effects of anaphylaxis may include one or more of the following: an itchy rash; throat or tongue swelling; shortness of breath; vomiting; lightheadedness; and low blood pressure. These symptoms typically develop over a period of minutes to hours. In the most severe cases, the effects of anaphylaxis can cause death of the patient.

The present invention provides a film according to the invention for use in the treatment of superficial bleeding. Superficial bleeding is caused by superficial wounds. These are minor cuts, abrasions and punctures that affect one or both of the outer two layers of the skin, i.e. the epidermis and the dermis.

The present invention provides a film according to the invention for use in the treatment of cardiac arrest. Cardiac arrest is a sudden loss of blood flow resulting from the failure of the heart to effectively pump blood. The effects of cardiac arrest are often severe. The effects of cardiac arrest may include one or more of the following: loss of consciousness; abnormal or absent breathing; chest pain; shortness of breath; and nausea. If not treated within minutes, cardiac arrest often leads to death of the patient.

Therefore, the present invention provides a film according to the invention for use in the treatment or amelioration of symptoms selected from the group consisting of: an itchy rash; throat or tongue swelling; shortness of breath; vomiting; lightheadedness; low blood pressure; bleeding from superficial wounds; loss of consciousness; abnormal or absent breathing; chest pain; shortness of breath; nausea; and combinations thereof.

Typically, the patient to be treated is an adult. Alternatively, the patient to be treated may be a child. The patient to be treated may be an elderly patient. The patient to be treated may be a child suffering from allergies.

Typically, the film is administered to the oral cavity of the patient. The film is preferably applied to an oral mucosa in the buccal or labial or sublingual areas or to the soft palate. The film is typically applied by the patient themselves. Alternatively, the film is administered to the patient by another person, e.g. a medical practitioner, a nurse, a carer, a social worker, a colleague of the patient or a family member of the patient.

The film is bioadhesive and adheres to the surface of the oral cavity upon application. After application, the alginate film begins to dissolve, releasing the active pharmaceutical ingredient. Typically, the film fully dissolves in a time period of from 0.1 to 60 minutes or more after application to the mucosa of the oral cavity. Preferably, the film fully dissolves in a time period of from 0.5 to 30 minutes, more preferably from 1 to 20 minutes, still more preferably from 3 to 10 minutes, and most preferably from 3 to 5 minutes after application to the mucosa of the oral cavity.

Without wishing to be bound by any particular theory, it is believed that as the film dissolves within the oral cavity, the active pharmaceutical ingredient which is concomitantly released may enter the bloodstream by one or both of two different routes: (a) via absorption across the oral mucosa directly into the bloodstream (the "oral transmucosal route"); and (b) via swallowing into the stomach and subsequent absorption across the epithelium of the intestines into the bloodstream. Typically the peak plasma concentration of the API in a patient exceeds 1 ng/mL. This peak plasma concentration may be achieved within 120 minutes from adhesion of the film to the mucosa of the oral cavity, preferably within 60 minutes from adhesion, more preferably within 45 minutes, even more preferably within 30 minutes or 20 minutes from adhesion, and most preferably within 10 minutes from adhesion.

Typically, a single film is applied to the patient, generally to the mucosa of the oral cavity, at a given time. However, in some cases it may be desirable to apply two films simultaneously to achieve the correct dose for an individual patient. When the API is adrenaline, and it is being used to treat acute anaphylaxis, the recommended dosage for adults is between 0.6 and 3 mg adrenaline per anaphylactic episode. When the API is adrenaline, and it is being used to treat acute anaphylaxis, the recommended dosage for infants and children is from 0.3 to 1.5 mg adrenaline per anaphylactic episode. [1] In some cases it may be desirable to apply more than two films simultaneously to achieve the correct dose for an individual patient, for example, three, four, five, six, seven, eight, nine, ten or more.

The present invention also therefore provides a method of treating a condition in a human patient, wherein said method comprises administration of at least one film according to the invention to the oral cavity of the human patient, optionally wherein the condition to be treated is anaphylaxis, superficial bleeding or cardiac arrest.

The present invention also provides the use of a film according to the invention for the manufacture of a medicament for the treatment of a condition in a human patient, optionally wherein the condition to be treated is anaphylaxis, superficial bleeding or cardiac arrest.

The present invention also provides a product comprising one or more films according to the invention, and packaging. Each of the films may individually be wrapped within a pouch, or multiple films may be wrapped together within the same pouch. Optionally, said pouch is made from PET-lined aluminium. The product may further comprise instructions for use of the film. These instructions may contain information on the recommended frequency or timing of use of the film by a patient, how to use remove the film from its pouch or packaging, how to adhere the film to a mucous membrane, and where within the oral cavity to adhere the film to a mucous membrane.

Any film or films of the present invention may also be used in combination with one or more other drugs or pharmaceutical compositions in the treatment of disease or conditions for which the films of the present invention and/or the other drugs or pharmaceutical compositions may have utility.

The one or more other drugs or pharmaceutical compositions may be administered to the patient by any one or more of the following routes: oral, systemic (e.g. transdermal, intranasal, transmucosal or by suppository), or parenteral (e.g. intramuscular, intravenous or subcutaneous). Compositions of the one or more other drugs or pharmaceutical compositions can take the form of tablets, pills, capsules, semisolids, powders, sustained release formulations, solutions, suspensions, elixirs, aerosols, transdermal patches, bioadhesive films, or any other appropriate compositions. The choice of formulation depends on various factors such as the mode of drug administration (e.g. for oral administration, formulations in the form of tablets, pills or capsules are preferred) and the bioavailability of the drug substance.

Manufacture of the Films

The films according to the invention may be manufactured by preparing a film-forming solution by addition and mixing of the constituent components of the film, distributing this solution onto a solid surface, and permitting the solution to dry on the surface to form a film. To distribute a solution or composition onto a solid surface the solution or composition may simply be poured onto and/or spread evenly over the surface, e.g. by use of a draw-down blade or similar equipment.

A typical method includes the process steps of:
(a) optionally, mixing at least one antioxidant in water;
(b) mixing the API in water, or in the solution obtained in step (a), and optionally subsequently adjusting the pH of the solution to the desired level by addition of an appropriate acid or base, typically a diluted aqueous acid or alkali, more typically a diluted aqueous alkali, and preferably adjusting the pH of the solution to from 3.8 to 5.5;
(c) optionally, mixing one or more excipients into the solution obtained in step (b);
(d) adding the alginate salt of monovalent cation under suitable conditions to result in the formation of a viscous cast;

(e) optionally, leaving the cast to de-aerate;
(f) pouring the cast onto a surface and spreading the cast out to the desired thickness, e.g. about 1 mm;
(g) drying the cast layer, typically at a temperature of from 30 to 60° C. until the residual water content of the film is from 0 to 20% by weight and a solid film is formed; and
(h) optionally, cutting the solid film into pieces of the desired size, further optionally placing these pieces into pouches, preferably wherein the pouches are made from PET-lined aluminium, sealing the pouches and further optionally, labelling them.

Accordingly, an exemplary method for making the films of the present invention includes the process steps of:
(a) mixing at least one antioxidant in water, optionally wherein the antioxidant is selected from the group consisting of ascorbic acid, citric acid, sodium bisulfite, sodium metabisulfite, butyl hydroxitoluene, and combinations thereof,
(b) mixing the API, preferably adrenaline or a pharmaceutically acceptable salt thereof, more preferably adrenaline tartrate, in the solution obtained in step (a), and optionally subsequently adjusting the pH of the solution to the desired level by addition of an appropriate acid or base, typically a diluted aqueous acid or alkali, more typically a diluted aqueous alkali, and preferably adjusting the pH of the solution to from 3.8 to 5.5;
(c) optionally, adding further water and/or one or more plasticizers and/or one or more fillers into the solution obtained in step (b) under further mixing;
(d) adding the alginate salt of monovalent cation under suitable conditions to result in the formation of a viscous cast, e.g. by mixing for about 30 minutes or until a lump free dispersion is achieved;
(e) optionally, leaving the cast to de-aerate, typically for from 5 to 14 hours;
(f) pouring the cast onto a surface, e.g. a plate, preferably a glass plate, and spreading the cast out to the desired thickness, e.g. about 1 mm, typically by means of an applicator;
(g) drying the cast layer, typically at a temperature of from 30 to 60° C., and preferably from 35 to 45° C., until the residual water content of the film is from 0 to 20% by weight, preferably from 5 to 15% by weight, and more preferably from 9 to 11% by weight and a solid film is formed; and
(h) optionally, cutting the solid film into pieces of the desired size, further optionally placing these pieces into pouches, preferably wherein the pouches are made from PET-lined aluminium, sealing the pouches and further optionally, labelling them.

An alternative method for manufacturing a film according to the invention includes the process steps of:
(a) mixing one or more excipients in water;
(b) separately, dissolving the API in water, or an aqueous solution containing one or more antioxidants, and optionally adjusting the pH of the solution to the desired level by addition of an appropriate acid or base, typically a diluted aqueous acid or alkali, more typically a diluted aqueous alkali, and preferably adjusting the pH of the solution to from 3.8 to 5.5;
(c) mixing the solution obtained in step (a) with the alginate salt of monovalent cation, e.g. for about 10 minutes;
(d) adding the solution obtained in step (b) to the solution obtained in step (c) under suitable conditions to result in the formation of a viscous cast, e.g. by mixing for about 20 minutes or until a lump free dispersion is achieved;
(e) optionally, leaving the cast to de-aerate, typically for from 5 to 14 hours;
(f) pouring the cast onto a surface, e.g. a plate, preferably a glass plate, and spreading the cast out to the desired thickness, e.g. about 1 mm, typically by means of an applicator;
(g) drying the cast layer, typically at a temperature of from 30 to 60° C., and preferably from 35 to 45° C., until the residual water content of the film is from 0 to 20% by weight, preferably from 5 to 15% by weight, and more preferably from 9 to 11% by weight; and
(h) optionally, cutting the solid film into pieces of the desired size, further optionally placing these pieces into pouches, preferably wherein the pouches are made from PET-lined aluminium, sealing the pouches and further optionally, labelling them.

Typically, in the method for manufacturing a film according to the invention, when an antioxidant is present in the film, the antioxidant is dissolved in aqueous solution prior to the addition of the API.

In an alternative variant of any of the above methods, after the viscous cast is poured onto a surface, it is first spread out to a thickness of about 2 mm by means of an applicator with a slit height of about 2 mm, and is then subsequently spread out to a thickness of about 1 mm by means of an applicator with a slit height of about 1 mm.

Typically, the alginate salt(s) are added to the API-containing water solution. Alternatively, the API and the alginate salt(s) are both dissolved together in solution. Alternatively, the API may be added to the alginate solution so as to give an emulsion or suspension of the API in the alginate solution. Alternatively, the film-forming composition of the invention may comprise both dissolved and non-dissolved active ingredients. For example, a film-forming composition may comprise a combination of active ingredient dissolved in the alginate solution and active ingredient suspended in the solution.

Additional API may be applied to the surface of the film before or after drying, e.g. as an aerosol spray onto a dry or wet film. An active ingredient may also be applied as a powder onto the surface of the film. A flavouring agent may additionally be applied in such a way.

The publications, patent publications and other patent documents cited herein are entirely incorporated by reference. Herein, any reference to a term in the singular also encompasses its plural. Where the term "comprising", "comprise" or "comprises" is used, said term may substituted by "consisting of", "consist of" or "consists of" respectively, or by "consisting essentially of", "consist essentially of" or "consists essentially of" respectively. Any reference to a numerical range or single numerical value also includes values that are about that range or single value. Any reference to a compound of Formula (I), e.g. adrenaline, also encompasses a physiologically acceptable salt thereof unless otherwise indicated. Any reference to alginate encompasses any physiologically acceptable salt thereof unless otherwise indicated. Unless otherwise indicated, any % value is based on the relative weight of the component or components in question.

EXAMPLES

The following are Examples that illustrate the present invention. However, these Examples are in no way intended to limit the scope of the invention. References to "adrenaline" or a pharmaceutically acceptable salt thereof throughout this Examples section refer specifically to the (−) enantiomer of adrenaline, i.e. (−)-adrenaline, or the pharmaceutically acceptable salt thereof, unless it is stated otherwise. References to "tartrate" throughout this Examples section refer specifically to the L-(+)-isomer of tartaric acid or a salt thereof, unless it is stated otherwise.

Example 1: Preparation of Adrenaline-Containing Films

Two basic film formulation protocols were developed. One film formulation protocol produced adrenaline-containing films without pH adjustment. The other film formulation protocol produced adrenaline-containing films in which the pH of the film formulation prior to coating and drying was adjusted to about 5.

Preparation of Adrenaline Buccal Films with pH Adjusted to 5

Batch formulae comprising adrenaline tartrate as the API at 1 mg/dose are set out in Table 1, and batch formulae comprising adrenaline tartrate as the API at 10 mg/dose are set out in Table 2. Each formulation comprises either ascorbic acid and/or sodium bisulfite. This component is believed to act as an antioxidant. The ratio of antioxidant to API is provided. Calculations are based on yields of 1000 doses/batch (dose size=3 cm$^2$).

TABLE 1

Batch formulae for production of adrenaline films adjusted to pH 5 containing 1 mg/dose of adrenaline tartrate.

| Component | Batch formulae for target dose strengths of 1 mg/dose adrenaline films (pH adjusted to 5) Molar ratio AA/Na—B/AT | | | Function |
|---|---|---|---|---|
| | 4/0/1 | 0/5/1 | 4/5/1 | |
| Adrenaline tartrate (g) | 2 | 2 | 2 | API |
| Ascorbic acid (g) | 4 | 0 | 4 | Antioxidant |
| Sodium bisulfite (g) | 0 | 3 | 3 | Antioxidant |
| Water (mL) | 300 | 300 | 300 | Solvent |
| Sorbitol (g) | 10.5 | 10.5 | 10.5 | Plasticizer |
| Glycerol (g) | 10.5 | 10.5 | 10.5 | Plasticizer |
| Sodium alginate (g) | 37.5 | 37.5 | 37.5 | Film-forming polymer |
| Sodium hydroxide (diluted) | q.s. to pH 5 | q.s. to pH 5 | q.s. to pH 5 | pH adjustment |

AA = ascorbic acid; Na—B = sodium bisulfite; AT = adrenaline tartrate; q.s. = quantum satis.

TABLE 2

Batch formulae for production of adrenaline films adjusted to pH 5 containing 10 mg/dose of adrenaline tartrate.

| Component | Batch formulae for target dose strengths of 10 mg/dose adrenaline films (pH adjusted to 5) Molar ratio AA/Na—B/AT | | | Function |
|---|---|---|---|---|
| | 4/0/1 | 0/5/1 | 4/5/1 | |
| Adrenaline tartrate (g) | 20 | 20 | 20 | API |
| Ascorbic acid (g) | 40 | 0 | 40 | Antioxidant |
| Sodium bisulfite (g) | 0 | 30 | 30 | Antioxidant |
| Water (mL) | 300 | 300 | 300 | Solvent |
| Sorbitol (g) | 10.5 | 10.5 | 10.5 | Plasticizer |
| Glycerol (g) | 10.5 | 10.5 | 10.5 | Plasticizer |
| Sodium alginate (g) | 37.5 | 37.5 | 37.5 | Film-forming polymer |
| Sodium hydroxide (diluted) | q.s. to pH 5 | q.s. to pH 5 | q.s. to pH 5 | pH adjustment |

AA = ascorbic acid; Na—B = sodium bisulfite; AT = adrenaline tartrate; q.s. = quantum satis.

The films were produced according to the following procedure:

Sodium bisulfite or ascorbic acid or a mix of sodium bisulfite and ascorbic acid was dissolved in the majority of the purified water under mixing, followed by the addition of adrenaline tartrate.

The glycerol and sorbitol were added to the solution under mixing.

The pH of the solution was adjusted to 5 by addition of a requisite quantity of diluted sodium hydroxide.

The batch volume was increased to the correct total amount by addition of the remainder of the purified water.

The sodium alginate was added under mixing for about 30 minutes or until a lump free dispersion was achieved, resulting in a viscous cast.

The cast was left overnight for de-aeration.

The cast was poured onto a glass plate and spread out to a thickness of 1 mm by means of an applicator.

The cast layer was dried in a drying cabinet heated to approximately 40° C. until a residual water content of about 10% by weight was achieved and a solid film was formed.

The solid film was cut into pieces measuring 15×20 mm with a knife.

The resulting films were placed individually into aluminium/polyethylene terephthalate (PET) pouches, sealed with a heat sealer and labelled.

Preparation of Adrenaline Buccal Films without pH Adjustment

Batch formulae comprising adrenaline tartrate as the API at 3 mg/dose with no pH adjustment prior to coating and drying are set out in Table 3. Each formulation comprises either ascorbic acid and/or sodium bisulfite. This component is believed to act as an antioxidant. The ratio of antioxidant to API is provided. One of the formulations comprising sodium bisulfite additionally comprises xylitol. Calculations are based on yields of 1000 doses/batch (dose size=3 cm$^2$).

The films were produced according to the following procedure:

Sodium bisulfite or ascorbic acid or a mix of sodium bisulfite and ascorbic acid was dissolved in the majority of the purified water under mixing, followed by the addition of adrenaline tartrate.

The glycerol and sorbitol (an xylitol, if present) were added to the solution under mixing.

The sodium alginate was added under mixing for about 30 minutes or until a lump free dispersion was achieved, resulting in a viscous cast.

The cast was left overnight for de-aeration.

The cast was poured onto a glass plate and spread out to a thickness of 1 mm by means of an applicator.

The cast layer was dried in a drying cabinet heated to approximately 40° C. until a residual water content of about 10% by weight was achieved and a solid film was formed.

The solid film was cut into pieces measuring 15×20 mm with a knife.

The resulting films were placed individually into aluminium pouches, sealed with a heat sealer and labelled.

Example 2: Physical Evaluation of Adrenaline-Containing Films

After manufacture, each of the batches of adrenaline-containing films prepared as described above in Example 1 was evaluated with respect to the following criteria:

TABLE 3

Batch formulae for production of adrenaline films without pH adjustment containing 3 mg/dose of adrenaline tartrate.

| | Batch formulae for target dose strengths of 3 mg/dose adrenaline films (no pH adjustment) Molar ratio AA/Na—B/AT | | | | |
|---|---|---|---|---|---|
| Component | 3/0/1 | 0/2/1 | 0/2/1 | 1/1/1 | Function |
| Adrenaline tartrate (g) | 5.5 | 5.5 | 5.5 | 5.5 | API |
| Ascorbic acid (g) | 9 | 0 | 0 | 2.9 | Antioxidant |
| Sodium bisulfite (g) | 0 | 3.4 | 3.4 | 1.7 | Antioxidant |
| Water (mL) | 200 | 230 | 230 | 230 | Solvent |
| Sorbitol (g) | 7 | 7 | 7 | 7 | Plasticizer |
| Glycerol (g) | 7 | 7 | 7 | 7 | Plasticizer |
| Xylitol (g) | 0 | 0 | 5 | 0 | Plasticizer |
| Sodium alginate (g) | 26.7 | 26.7 | 26.7 | 26.7 | Film-forming polymer |

AA = ascorbic acid; Na—B = sodium bisulfite; AT = adrenaline tartrate.

| Property | Criteria |
|---|---|
| 1. Cast texture: | lump free, homogenous viscous cast (visual inspection) free of bubbles prior to coating (visual inspection) |
| 2. Residual moisture*: | 9-11% (in process control) |
| 3. Film appearance: | translucent, transparent and colour homogenous (visual inspection) smooth and flat surface structure (visual inspection) pliable and flexible (visual inspection) |
| 4. Dose weight homogeneity: | weighing of doses randomly selected within a film batch |
| 5. Adrenaline content**: | RP-HPLC analysis on the changes of dose strengths after stability studies |

*Residual moisture: IR-induced water vaporization combined with real-time weight measurement was used. Percentage of change in weight at start until no further change was observed as the measure of residual moisture.
**Adrenaline content and homogeneity: Reverse phase high-performance liquid chromatography (RP-HPLC) separation with detection at 280 nm was used. Amount of adrenaline/dose was calculated using an adrenaline standard curve. [9]

Evaluation of Adrenaline Buccal Films with pH Adjusted to 5

Adrenaline was fully dissolved in the liquid (water) phase, and lump free, homogenous (yellowish) viscous casts could be prepared with each individual batch formula/protocol with pH adjustment as described above in Example 1. Air bubbles generated during preparation of the casts and which introduce inhomogeneity in the films, were removed by leaving the cast overnight at room temperature for passive de-aeration prior to coating.

All prepared films had smooth and flat surface structures with flexible properties when dried to a water content of 9-11%.

Quantitative determination of adrenaline in films was performed on RP-HPLC in isocratic mode. Ammonium acetate was used as mobile phase and the UV detection was made at 280 nm.

Evaluation of Adrenaline Buccal Films with No pH Adjustment

Lump free, (yellowish) viscous casts could be prepared with each individual batch formula/protocol without pH adjustment as described above in Example 1. Most of the air bubbles generated during preparation of the casts were removed by leaving the cast overnight at room temperature for passive de-aeration prior to coating.

Except for some air bubbles, all prepared films had smooth and flat surface structures with flexible properties when dried to a water content of 9-11%. The flexible properties can be further improved by adding xylitol as an additional plasticizer.

Example 3: Stability Studies on Adrenaline-Containing Films

Stability studies were also carried out to determine the stability of the adrenaline API within the buccal films prepared in Example 1. As mentioned above, adrenaline is prone to degradation via oxidation and it is desirable to minimize this degradation (i.e. optimize the stability of the buccal films).

Stability Studies on Adrenaline Buccal Films with pH Adjusted to 5

Initial stability studies were carried out on the 10 mg/dose adrenaline buccal film adjusted to a pH of 5 prior to coating and drying, and which contained only ascorbic acid as an antioxidant (i.e. the formulation set out in column 2 of Table 2, in Example 1 above).

FIG. 1 shows the effect of temperature on the oxidation process of said adrenaline films stabilized by ascorbic acid. The adrenaline buccal films to be tested were stored at room temperature (RT) and 40° C. respectively, and adrenaline content per dose was analysed after 0, 7, 18, 41 and 83 days. It is clear from these results that the oxidation process of adrenaline films containing ascorbic acid can be accelerated by the increased temperature. Adrenaline films were almost stable at room temperature (RT) after 83 days, while a gradual degradation occurred for adrenaline films stored at 40° C., in which a loss of about 30% adrenaline content after 83 days was observed.

Stability Studies on Adrenaline Buccal Films without pH Adjustment pH measurements and stability studies were carried out on each of the four adrenaline buccal film formulations prepared without pH adjustment (i.e. the formulations set out in Table 3, in Example 1 above). The results of these studies are set out in Table 4 below.

TABLE 4

The pH of the casts of batch formulae prepared without pH adjustment but having different antioxidants and plasticizers added, and the amount of adrenaline API present in each of the formulations at an initial time point and after three weeks. Standard deviations are provided in parentheses (no. samples tested in each assay = 5).

| | | Formulation from Table 3 | | |
|---|---|---|---|---|
| | | 0/2/1 | | |
| Molar ratio AA/Na—B/AT | 3/0/1 | Without xylitol | With xylitol | 1/1/1 |
| pH of the cast | 3.8 | 4.3 | 4.1 | 4.0 |
| Assay adrenaline (mg/dose) initial film samples | 2.8 (0.1) | 3.1 (0.1) | — | 2.9 (0.2) |

TABLE 4-continued

The pH of the casts of batch formulae prepared without pH adjustment but having different antioxidants and plasticizers added, and the amount of adrenaline API present in each of the formulations at an initial time point and after three weeks. Standard deviations are provided in parentheses (no. samples tested in each assay = 5).

| | Formulation from Table 3 | | | |
|---|---|---|---|---|
| | | 0/2/1 | | |
| Molar ratio AA/Na—B/AT | 3/0/1 | Without xylitol | With xylitol | 1/1/1 |
| Assay adrenaline (mg/dose) after 3 weeks | 2.5 (0.1) | 1.9 (0.1) | — | 2.8 (0.1) |
| Assay adrenaline (μm/mg film) after 3 weeks | 60.0 (2.0) | 43.6 (0.4) | — | 62.1 (1.0) |

AA = ascorbic acid; Na—B = sodium bisulfite; AT = adrenaline tartrate.

It was observed that the pH of all the prepared casts (containing different stabilizer(s)) was greater than 3.8 without any external pH adjustment. This is beneficial, because sodium alginate can be transformed to alginic acid and begin to gel at a pH below 3.8. Thus, acceptable casts containing adrenaline as API can be prepared without the need for external pH adjustment.

Stability studies based on these batch formulas were performed by evaluation of the adrenaline content per dose in each formulation at an initial time point and after storage for 3 weeks at room temperature. As set out in Table 5, the stability studies show that adrenaline films comprising ascorbic acid as the sole antioxidant were more stable than adrenaline films comprising sodium bisulfite as the sole antioxidant after 3 weeks at RT. This could likely be explained by the relatively lower pH of the ascorbic acid-containing cast and/or the superior antioxidative property of ascorbic acid compared with sodium bisulfite. However, the greatest stabilizing effect on adrenaline was observed for the adrenaline films containing both ascorbic acid and sodium bisulfite, which surprisingly suggests that a synergic effect arises from combination of both of these antioxidants in the films.

The dose-weight variations obtained in this study were considered acceptable for sample preparation in lab scale and the homogeneity data (mg adrenaline/mg film) showed good consistency within batches.

CONCLUSIONS

The results in Examples 1 to 3 show the possibility to formulate stable adrenaline buccal film formulations. The main conclusions of this study are summarized below.

- Lump free, homogenous viscous casts with few air bubbles were obtained, by allowing the cast to de-aerate for over 15 hours.
- The prepared films were homogenous and had a smooth and flat surface. They were pliable and flexible and considered as being easy to handle and administer for the patient.
- The dose weight variations obtained in this study were considered acceptable for sample preparation in lab-scale and the homogeneity data (mg Adrenaline/mg film) showed good consistency within batches.
- For films in which pH in the pre-cast solution was adjusted to 5, Adrenaline films were almost stable at room temperature (RT) after 83 days while a gradual degradation occurred for adrenaline films stored at 40° C.
- For films at around pH 4, adrenaline films with ascorbic acid were more stable than with the sodium bisulfite at RT. However, the synergic effect of using both ascorbic acid and sodium bisulfite has the best stabilizing effect to Adrenaline in films.

Example 4: Effect of Ascorbic Acid:Sodium Bisulfite Ratio on Film Stability

The physical and chemical stability of twenty-five adrenaline alginate based buccal film formulations containing ascorbic acid and/or sodium bisulfite as antioxidants were tracked under ambient conditions (room temperature and relative humidity (R.H.)) and accelerated conditions (40° C./75% R.H. and 50° C./75% R.H.).

The compositions tested in this study are described in Table 5. The formulations containing a combination of plasticizers and stabilizers and the compositions were prepared at pH4.1±0.2.

TABLE 5

Composition of individual antioxidant-containing films tested in this study.

| Batch # | #50 | #51 | #52 | #53 | Function |
|---|---|---|---|---|---|
| Adrenaline | 1 mg | 1 mg | 1 mg | 1 mg | API |
| Ascorbic acid | 0.05 mg | 0.10 mg | 0.25 mg | 0.5 mg | Stabilizer/antioxidant |
| Sodium bisulfite | — | — | — | — | Stabilizer/antioxidant |
| Sodium alginate | c. 13.4 mg | c. 13.4 mg | c. 13.4 mg | c. 13.4 mg | Film forming agent |
| Sorbitol | c. 3.5 mg | c. 3.5 mg | c. 3.5 mg | c. 3.5 mg | Plasticizer |
| Glycerol | c. 3 mg | c. 3 mg | c. 3 mg | c. 3 mg | Plasticizer |
| Water | c. 2 mg | c. 2 mg | c. 2 mg | c. 2 mg | Solvent |

TABLE 5-continued

Composition of individual antioxidant-containing films tested in this study.

| Batch # | #54 | #55 | #56 | #57 | Function |
|---|---|---|---|---|---|
| Adrenaline | 1 mg | 1 mg | 1 mg | 1 mg | API |
| Ascorbic acid | — | — | — | — | Stabilizer/antioxidant |
| Sodium bisulfite | 0.03 mg | 0.06 mg | 0.15 mg | 0.30 mg | Stabilizer/antioxidant |
| Sodium alginate | c. 13.4 mg | c. 13.4 mg | c. 13.4 mg | c. 13.4 mg | Film forming agent |
| Sorbitol | c. 3.5 mg | c. 3.5 mg | c. 3.5 mg | c. 3.5 mg | Plasticizer |
| Glycerol | c. 3 mg | c. 3 mg | c. 3 mg | c. 3 mg | Plasticizer |
| Water | c. 2 mg | c. 2 mg | c. 2 mg | c. 2 mg | Solvent |

| Batch # | #58 | #59 | #60 | #61 | Function |
|---|---|---|---|---|---|
| Adrenaline | 1 mg | 1 mg | 1 mg | 1 mg | API |
| Ascorbic acid | 0.05 mg | 0.05 mg | 0.05 mg | 0.05 mg | Stabilizer/antioxidant |
| Sodium bisulfite | 0.03 mg | 0.06 mg | 0.15 mg | 0.30 mg | Stabilizer/antioxidant |
| Sodium alginate | c. 13.4 mg | c. 13.4 mg | c. 13.4 mg | c. 13.4 mg | Film forming agent |
| Sorbitol | c. 3.5 mg | c. 3.5 mg | c. 3.5 mg | c. 3.5 mg | Plasticizer |
| Glycerol | c. 3 mg | c. 3 mg | c. 3 mg | c. 3 mg | Plasticizer |
| Water | c. 2 mg | c. 2 mg | c. 2 mg | c. 2 mg | Solvent |

| Batch # | #62 | #63 | #64 | #65 | Function |
|---|---|---|---|---|---|
| Adrenaline | 1 mg | 1 mg | 1 mg | 1 mg | API |
| Ascorbic acid | 0.10 mg | 0.10 mg | 0.10 mg | 0.10 mg | Stabilizer/antioxidant |
| Sodium bisulfite | 0.03 mg | 0.06 mg | 0.15 mg | 0.30 mg | Stabilizer/antioxidant |
| Sodium alginate | c. 13.4 mg | c. 13.4 mg | c. 13.4 mg | c. 13.4 mg | Film forming agent |
| Sorbitol | c. 3.5 mg | c. 3.5 mg | c. 3.5 mg | c. 3.5 mg | Plasticizer |
| Glycerol | c. 3 mg | c. 3 mg | c. 3 mg | c. 3 mg | Plasticizer |
| Water | c. 2 mg | c. 2 mg | c. 2 mg | c. 2 mg | Solvent |

| Batch # | #66 | #67 | #68 | #69 | Function |
|---|---|---|---|---|---|
| Adrenaline | 1 mg | 1 mg | 1 mg | 1 mg | API |
| Ascorbic acid | 0.25 mg | 0.25 mg | 0.25 mg | 0.25 mg | Stabilizer/antioxidant |
| Sodium bisulfite | 0.03 mg | 0.06 mg | 0.15 mg | 0.30 mg | Stabilizer/antioxidant |
| Sodium alginate | c. 13.4 mg | c. 13.4 mg | c. 13.4 mg | c. 13.4 mg | Film forming agent |
| Sorbitol | c. 3.5 mg | c. 3.5 mg | c. 3.5 mg | c. 3.5 mg | Plasticizer |
| Glycerol | c. 3 mg | c. 3 mg | c. 3 mg | c. 3 mg | Plasticizer |
| Water | c. 2 mg | c. 2 mg | c. 2 mg | c. 2 mg | Solvent |

| Batch # | #70 | #71 | #72 | #73 | Function |
|---|---|---|---|---|---|
| Adrenaline | 1 mg | 1 mg | 1 mg | 1 mg | API |
| Ascorbic acid | 0.5 mg | 0.5 mg | 0.5 mg | 0.5 mg | Stabilizer/antioxidant |
| Sodium bisulfite | 0.03 mg | 0.06 mg | 0.15 mg | 0.30 mg | Stabilizer/antioxidant |
| Sodium alginate | c. 13.4 mg | c. 13.4 mg | c. 13.4 mg | c. 13.4 mg | Film forming agent |
| Sorbitol | c. 3.5 mg | c. 3.5 mg | c. 3.5 mg | c. 3.5 mg | Plasticizer |
| Glycerol | c. 3 mg | c. 3 mg | c. 3 mg | c. 3 mg | Plasticizer |
| Water | c. 2 mg | c. 2 mg | c. 2 mg | c. 2 mg | Solvent |

The films were packed in Alu/PET pouches immediately after preparation. All samples were protected from light and stored under ambient conditions (room temperature and humidity) and accelerated conditions (40° C./75% R.H. and 50° C./75% R.H.).

Analysis Schedule and Methods

The formulations were analyzed according to the stability program set out in Table 6. The stability of the adrenaline buccal film prototypes were followed for 12 weeks. The analytical methods and specification limits applied are described in Table 7.

TABLE 6

Stability program used in this study

| Time points | Date | Room temperature and R.H. | 40° C./75% R.H. | 50° C./75% R.H. |
|---|---|---|---|---|
| Initial | 2018 Dec. 21 | A-D | A-D | A-D |
| 2 weeks | 2019 Jan. 4 | A-B | A-B | A-B |
| 4 weeks | 2019 Jan. 18 | A-D | A-D | A-D |

TABLE 6-continued

Stability program used in this study

| Time points | Date | Room temperature and R.H. | 40° C./75% R.H. | 50° C./75% R.H. |
|---|---|---|---|---|
| 8 weeks | 2019 Feb. 2 | A-D | A-D | A-D |
| 12 weeks | 2019 Mar. 15 | A-D | A-D | A-D |

TABLE 7

Stability analysis method and specifications applied in this study.

| Item | Analysis | Method description | Limits |
|---|---|---|---|
| A | Assay | Measurement of mg adrenaline/mg film using HPLC-RPC | ±5-10% |
| B | Related substances | Determination of impurity content by HPLC-RPC | TBD |
| C | Appearance | Visual inspection. Graded on a 1-5 scale: 1: Completely inhomogeneous film. 2: Film with a lot of visible spots. 3: Film with some visible spots. 4: Mostly homogenous film. 5: Homogeneous film. | 4-5 approved 1-3 not approved |
| D | Pliability | Film will be bent 5 times: 1: Very brittle and rigid. 2: Rigid and brittle 3: Rigid 4: Somewhat rigid. 5: Soft and flexible. | 4-5 approved 1-3 not approved |
| E | Appearance crystals | Polarized light microscopy | N/A |

The HPLC-RPC (high performance liquid chromatography-reversed phase chromatography) method used (developed by Klaria Pharma Holding AB, Uppsala, Sweden) is as follows:

Solvent mixture A was prepared by dissolving 5 g of potassium dihydrogen phosphate in 1000 mL MilliQ water using a magnetic stirrer. The pH was then adjusted to 5.5 with 1 mol/L sodium hydroxide.

Solvent mixture B was prepared by mixing solvent mixture A with acetonitrile in a ratio of 13:87 (by volume)

A stock solution of 300 µg/mL adrenaline bitartrate was prepared by weighing 30 mg of adrenaline bitartrate and dissolving in 100 g of solvent mixture B.

Adrenaline bitartrate standards were prepared according to the dilution schedule of the stock solution shown in Table 8 below.

TABLE 8

Preparation of adrenaline bitartrate standards

| Standard | Dilution | Adrenaline bitartrate conc. (µg/mL) | Adrenaline conc. (µg/mL) |
|---|---|---|---|
| Blank | Mobile phase | 0 | 0 |
| 1 | 1:4 dilution of stock solution with diluent | 60 | 33 |
| 2 | 1:2 dilution of stock solution with diluent | 100 | 55 |
| 3 | 1:1 dilution of stock solution with diluent | 150 | 82.5 |
| 4 | Stock solution | 300 | 165 |

To prepare a test sample for 1 mg API dose/film, 20 g of solvent mixture B was added to a 100 mL beaker. Two test films were weighed and dissolved in the solvent mixture B using magnetic stirrer for 10 minutes. An aliquot of sample solution was filtered through a 0.45 µm HPLC grade filter. The first 2-3 mL of solution was discarded and approximately 1 mL sample solution was then collected.

To prepare a test sample for 3 mg API dose/film, the same protocol was employed, except that the amount of solvent mixture B used was 60 g.

HPLC was performed with the following settings: column used=ReproSil-Pur 120 C18-AQ; flow rate=1.0 mL/min; injection volume (sample loop)=20 µL; run time=15 min.; detection wavelength=210 nm; column temperature=35° C.

The column was equilibrated with at least 5 column volumes in mobile phase at a flow rate of 1 mL/min.

The analysis was performed as a gradient run, as follows (Mobile Phase A=acetonitrile:solvent mixture A (5:95, by volume) and connected to pump A1; Mobile Phase B=acetonitrile:solvent mixture A (45:55, by volume) and connected to pump B2):

| Time (min) | % mobile phase A | % mobile phase B |
|---|---|---|
| 0 | 95 | 5 |
| 10 | 67 | 33 |
| 11 | 95 | 5 |
| 15 | 95 | 5 |

Samples were run through the HPLC in the following order: (1) blank; (2) blank; (3) blank; (4) standard 1; (5) standard 2; (6) standard 3; (7) standard 4; (8) sample 1; (9) sample 2; (10) continue with samples through to last sample; (11) blank; (12) standard 1; (13) standard 2; (14) standard 3; (15) standard 4; (16) stop.

After data collection, the standard samples were used to produce a calibration curve, against which the sample data could then be measured to determine the concentration of adrenaline and impurities in the samples.

Approximate relative retention time (RRT) for the known impurities using current RP-HPLC method are provided in Table 9 below.

TABLE 9

Relative retention time for the specified impurities. RRT calculated versus the retention time of the main peak.

| Specific impurities | RRT |
| --- | --- |
| Norepinephrine (imp. B) | 0.92 |
| Adrenalone (imp. C) | 1.12 |
| Adrenaline Sulfonic Acid (imp. F) | 0.89 |

Study Results—after 2- and 4-Week Storage
Physical Changes

Judgment of appearance and pliability were performed by visual inspection according to Table 7. All the formulations passed the appearance and pliability specification initially.

After 4 weeks storage under both ambient and accelerated conditions, all the studied formulations passed the pliability specification with no signs of crystallization of adrenaline in any of the studied film formulations. However, adrenaline films containing ascorbic acid turned pale yellow after 4-week storage at 50° C./75% R.H. The colour changes are thought to be correlated to the ascorbic acid content and storage temperature. No colour change was noticed in any of the formulations after 4-week storage at ambient and 40° C./75% R.H. A gradient of color change was seen as the content of ascorbic acid increased (e.g. batch numbers 57, 50, 51, 52 and 53 respectively displayed an increasingly intense yellow colour).

Chemical Changes

The chemical stability of the studied formulations were tested after 2 and 4 weeks at ambient, 40° C./75% R.H. and 50° C./75% R.H. conditions via HPLC.

Under ambient conditions, no significant differences in chemical stability were observed after 2 weeks between film formulations with and without stabilizer(s) (i.e. antioxidant (s)). A slight increase in the content of impurity F was detected after 4 weeks in formulations containing one of either bisulfite or ascorbic acid, whilst less or even no impurity F was detected in film formulations containing both stabilizers. In general, all the studied formulations were relatively stable at ambient condition in which the content of total impurities was below 1.0% after 4 weeks storage.

Under accelerated conditions (40° C./75% R.H. and 50° C./75% R.H.), the concentration of impurities increased with the concentration of stabilizers in the formulation. An increasing trend of impurity F can be seen in film formulations containing only bisulfite as stabilizer, while the content of two unknown impurities at RRT 2.86 and 3.16 increased with the concentration of ascorbic acid in film formulations. The addition of ascorbic acid to bisulfite-containing film formulations can inhibit the formation of impurities F (RRT 0.89) and C (RRT 1.14). Bisulfite mixed with ascorbic acid at low concentration (e.g. 0.05 in molar ratio to adrenaline) has an improved stabilizing effect. A smaller number of impurities and generally lower content thereof were observed in these formulations. However, a high concentration of ascorbic acid (i.e. 0.25 and 0.5 in molar ratio to adrenaline) had a sub-optimal effect on the chemical stability, resulting in higher content of total impurities.

Study Results—after 8-Week Storage
Physical Changes

Under ambient conditions, all the studied formulations passed the appearance and pliability specification in accordance to the limits listed in Table 7.

Under accelerated conditions (40° C./75% R.H. and 50° C./75% R.H.), a colour change of adrenaline films was noticed. The change in color was mainly correlated to the concentration of ascorbic acid in formulation and the storage temperature. A gradient of colour change was observed as the content of ascorbic acid increased, and was more pronounced after storage at higher temperature.

Chemical Changes

In general, all the studied formulations were relatively stable at ambient conditions in which the content of total impurities was below 1.0% after 8-week storage. An improved stabilizing effect can be obtained (content of total impurities<0.6%) for formulations containing bisulfite. A small amount of impurity F (RRT 0.89) was observed in formulation containing either bisulfite or ascorbic acid, while no impurity F can be seen in film formulations including both stabilizers. Formation of impurity at RRT 3.16 occurred in some formulations containing ascorbic acid.

Figure 2:
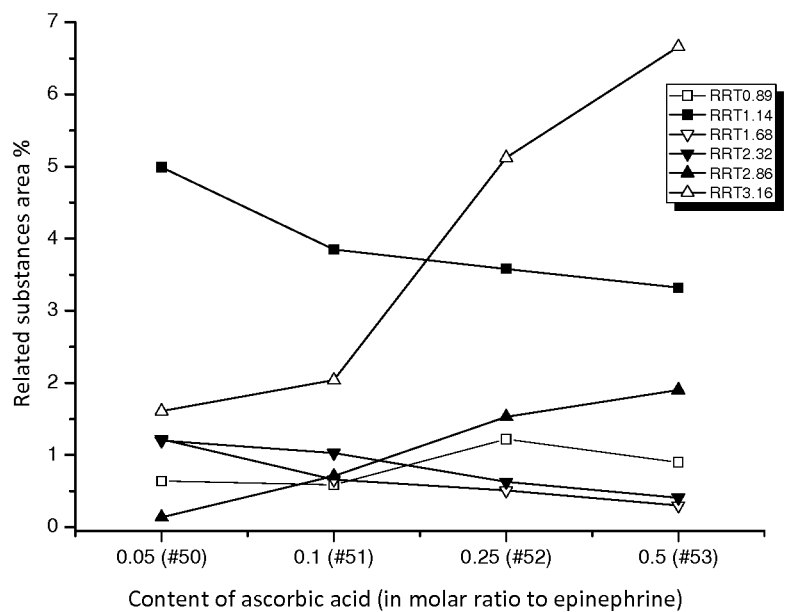
FIG. 2 shows the relative substance area (%) for impurities having a relative retention time (RRT) of 0.89, 1.14, 1.68, 2.32, 2.86 and 3.16 for formulations #50, #51, #52 and #53 with increasing molar ratio of ascorbic acid to molar ratio of adrenaline. Films were stored for 8 weeks at 40° C./75% R.H.
Figure 3:
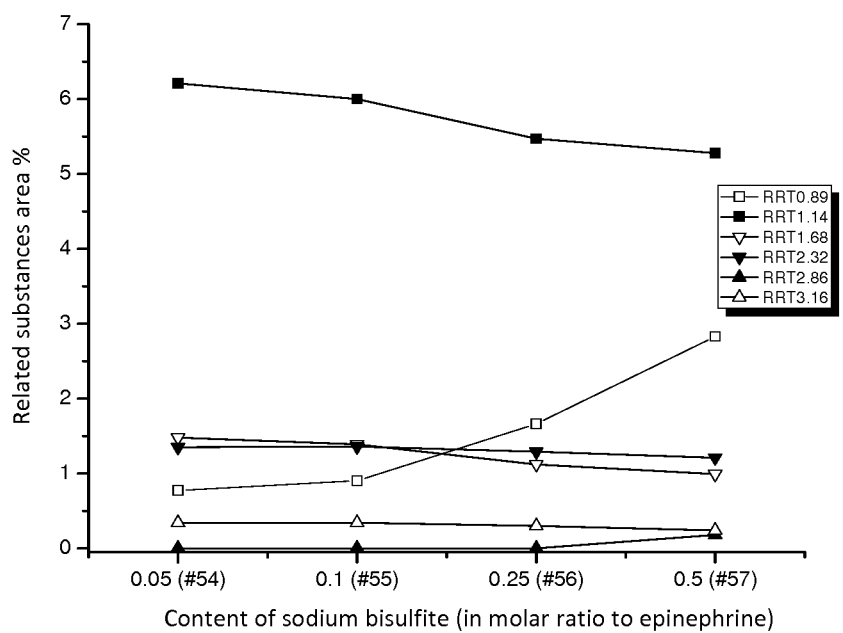
FIG. 3 shows the relative substance area (%) for impurities having an RRT of 0.89, 1.14, 1.68, 2.32, 2.86 and 3.16 for formulations #54, #55, #56 and #57 with increasing molar ratio of sodium bisulfite to molar ratio of adrenaline. Films were stored for 8 weeks at 40° C./75% R.H.

Under accelerated conditions (40° C./75% R.H. and 50° C./75% R.H.), the content of total impurities increased with the concentration of ascorbic acid in formulation, while the impact of the bisulfite concentration was not significant. Ascorbic acid at a high concentration (e.g. 0.5 in molar ratio to adrenaline) resulted in a higher content of total impurities than formulation with no stabilizers (i.e. batch #74). The content of impurities at RRT 2.86 and 3.16 increased with the increased ascorbic acid concentration in the formulation, while the content of impurities at RRT 1.14, 1.68 and 2.32 decreased with increased ascorbic acid concentration. Moreover, the formation of impurity F (RRT 0.89) can be found in all the studied formulations, but an increasing amount of impurity F can be seen in film formulations with increased bisulfite content. The effect of ascorbic acid and sodium bisulfite concentration on each of the measured impurities at 40° C./75% R.H. can be seen in FIGS. 2 and 3.

Study Results—after 12-Week Storage
Physical Changes

Under ambient conditions (room temperature), all formulations passed the appearance and pliability specification according to the limits listed in Table 7. No colour change of any of the adrenaline-containing films was observed.

Under accelerated conditions (40° C./75% R.H. and 50° C./75% R.H.), a colour change of some of the films was noticed and was more severe than colour changes observed after 8-week storage. A gradient of colour change was still observed as the content of ascorbic acid increased, and it was more obvious after storage at higher temperature. The impact of bisulfite content on the color change was not significant.

Chemical Changes

Under ambient conditions, all the studied formulations were relatively stable. The content of total impurities in most studied formulations were below 1.0%, except for #56 (1.77%) and #57 (1.36%) which was mainly a result of formation of impurity F (RRT 0.89). Additionally, a small amount of impurity at RRT 3.16 could be found in formulations containing ascorbic acid.

Figure 4:
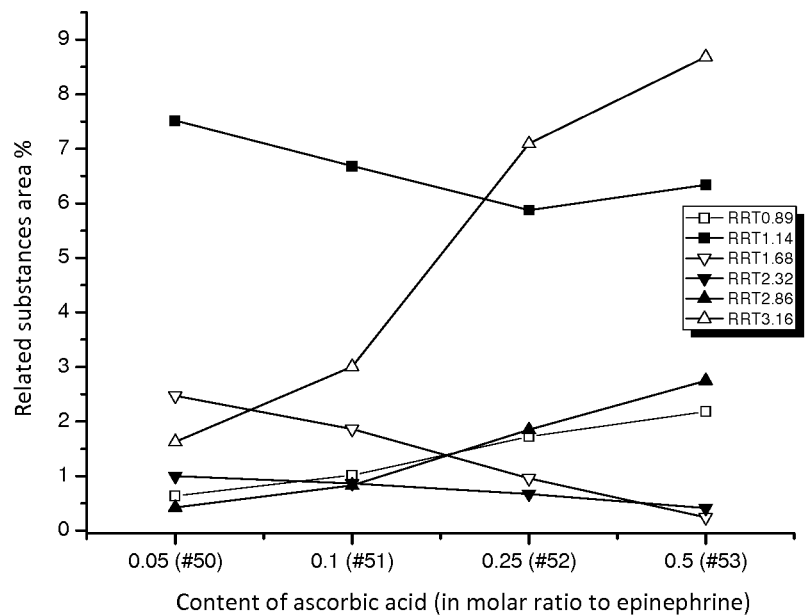
FIG. 4 shows the relative substance area (%) for impurities having an RRT of 0.89, 1.14, 1.68, 2.32, 2.86 and 3.16 for formulations #50, #51, #52 and #53 with increasing molar ratio of ascorbic acid to molar ratio of adrenaline. Films were stored for 12 weeks at 40° C./75% R.H.
Figure 5:
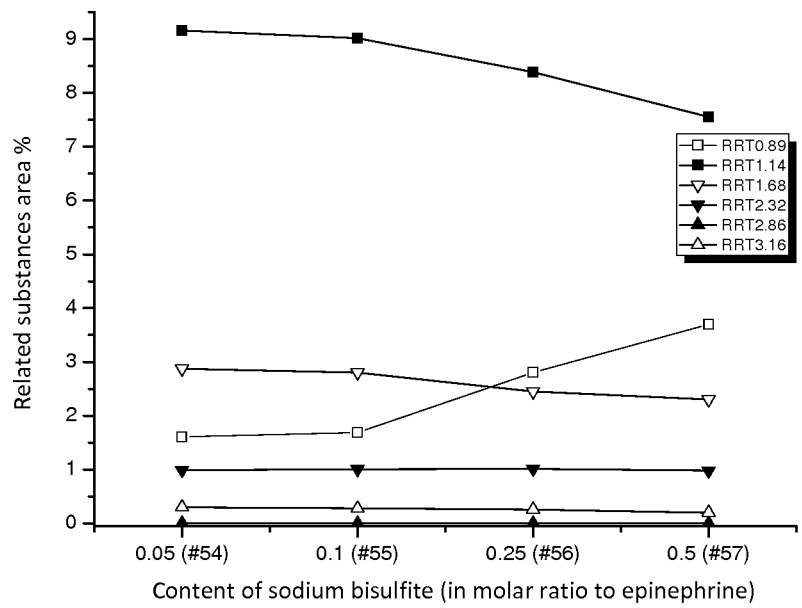
FIG. 5 shows the relative substance area (%) for impurities having an RRT of 0.89, 1.14, 1.68, 2.32, 2.86 and 3.16 for formulations #54, #55, #56 and #57 with increasing molar ratio of sodium bisulfite to molar ratio of adrenaline. Films were stored for 12 weeks at 40° C./75% R.H.

Under accelerated conditions (40° C./75% R.H. and 50° C./75% R.H.), similar trends were found compared to results after 8 weeks storage (see FIGS. 4 and 5 for data on films stored at 40° C./75% R.H.). Impurity content was much higher in all formulations after storage at 40° C./75% R.H. than at 50° C./75% R.H. The content of total impurities increased with ascorbic acid concentration in formulation, while no clear trend was noticed with increasing sodium bisulfite content. Regarding individual impurities, the content of impurities at RRT 2.86 and 3.16 increased with the increased content of ascorbic acid in formulation, while the content of impurities at RRT 1.14, 1.68 and 2.32 decreased with the increased content of ascorbic acid (see FIGS. 4 and 5). An increasing amount of impurity F can be seen in film formulations with increased bisulfite content.

Example 5: Effect of EDTA Addition on Stability

In general the adrenaline formulations studied in Example 4 were stable after 4 weeks storage at ambient conditions. Most of the formulations containing ascorbic acid and sodium bisulfite (in molar ratio to adrenaline ranging between 0.05 and 0.5) have shown a stabilizing effect compared to the control. However, it was noticed that formation of impurities at RRT 0.89 (Imp. F) and 3.16 accelerated with increasing concentration of stabilizers in the formulations after 4-week storage. The formation of these impurities is probably caused by sulfonation reaction of adrenaline with sodium bisulfite and aided by a possible pro-oxidant activity of higher concentrations of ascorbic acid:

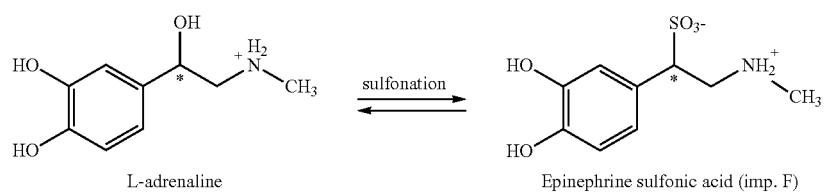

L-adrenaline     sulfonation ⇌     Epinephrine sulfonic acid (imp. F)

As the formation of these impurities accelerated at higher molar ratio between stabilizers and adrenaline, formulations with stabilizers at low molar ratio to adrenaline (≤0.05) were investigated in order to further optimize the film stability Thus, in this example study, the molar ratio of sodium bisulfite and ascorbic acid to adrenaline in the formulations were reduced, and EDTA added as an additional stabilizing agent. As a more commonly used sulfite source in pharmaceutics, sodium metabisulfite was also employed in place of sodium bisulfite. Fourteen adrenaline buccal formulations at pH 4.1±0.2 were thus investigated under cold storage conditions (5° C.), ambient conditions (room temperature and humidity) and accelerated conditions (40° C./75% R.H. and 50° C./75% R.H.). Both 1 mg and 3 mg adrenaline films were investigated. The formulations prepared in this study are set out in Table 10 below.

TABLE 10

Compositions of the studied formulations.

| Batch # | #79 | #80 | #81 | #82 | #83 | Batch # |
|---|---|---|---|---|---|---|
| Adrenaline | 3 mg | 3 mg | 3 mg | 3 mg | 3 mg | API |
| Ascorbic acid | — | 0.07 mg | — | 0.03 mg | 0.07 mg | Stabilizer/Antioxidant |
| Sodium metabisulfite | — | — | 0.004 mg | 0.004 mg | 0.004 mg | Stabilizer/Antioxidant |
| EDTA | — | — | — | — | — | Stabilizer/Antioxidant |
| Sodium alginate | c. 13 mg | c. 13 mg | c. 13 mg | c. 13 mg | c. 13 mg | Film forming agent |
| Sorbitol | c. 3 mg | c. 3 mg | c. 3 mg | c. 3 mg | c. 3 mg | Plasticizer |
| Glycerol | c. 3 mg | c. 3 mg | c. 3 mg | c. 3 mg | c. 3 mg | Plasticizer |
| Water | c. 3 mg | c. 3 mg | c. 3 mg | c. 3 mg | c. 3 mg | Solvent |

| Batch # | #84 | #85 | #86 | #87 | #88 | Function |
|---|---|---|---|---|---|---|
| Adrenaline | 3 mg | 3 mg | 3 mg | 3 mg | 3 mg | API |
| Ascorbic acid | 0.144 mg | 0.07 mg | 0.144 mg | — | 0.07 mg | Stabilizer/Antioxidant |
| Sodium metabisulfite | 0.004 mg | 0.015 mg | 0.015 mg | 0.05 mg | 0.004 mg | Stabilizer/Antioxidant |
| EDTA | — | — | — | — | 0.002 mg | Stabilizer/Antioxidant |
| Sodium alginate | c. 13 mg | c. 13 mg | c. 13 mg | c. 13 mg | c. 13 mg | Film forming agent |
| Sorbitol | c. 3 mg | c. 3 mg | c. 3 mg | c. 3 mg | c. 3 mg | Plasticizer |
| Glycerol | c. 3 mg | c. 3 mg | c. 3 mg | c. 3 mg | c. 3 mg | Plasticizer |
| Water | c. 3 mg | c. 3 mg | c. 3 mg | c. 3 mg | c. 3 mg | Solvent |

| Batch # | #89 | #90 | #91 | #92 | Function |
|---|---|---|---|---|---|
| Adrenaline | 3 mg | 3 mg | 3 mg | 1 mg | API |
| Ascorbic acid | — | 0.07 mg | — | 0.02 mg | Stabilizer/Antioxidant |
| Sodium metabisulfite | 0.05 mg | 0.004 mg | 0.05 mg | 0.001 mg | Stabilizer/Antioxidant |
| EDTA | 0.002 mg | 0.078 mg | 0.078 mg | — | Stabilizer/Antioxidant |
| Sodium alginate | c. 13 mg | c. 13 mg | c. 13 mg | c. 13 mg | Film forming agent |
| Sorbitol | c. 3 mg | c. 3 mg | c. 3 mg | c. 3 mg | Plasticizer |
| Glycerol | c. 3 mg | c. 3 mg | c. 3 mg | c. 3 mg | Plasticizer |
| Water | c. 3 mg | c. 3 mg | c. 3 mg | c. 3 mg | Solvent |

The films were packed in Alu/PET pouches immediately after preparation. All samples were protected from light and stored under cold storage conditions (5° C.), ambient conditions (room temperature and humidity) or accelerated conditions (40° C./75% R.H. and 50° C./75% R.H.).
Analysis Schedule and Methods The formulations were analyzed according to the stability program set out in Table 11. The stability of the adrenaline buccal film prototypes were followed for 12 weeks. The analytical methods and specification limits applied are as described above in Table 7.

TABLE 11

Stability program used in this study

| Time points | Date | 5° C. | Ambient | 40° C./75% R.H. |
|---|---|---|---|---|
| Initial | 2019 Jan. 17 | A-E | A-E | A-E |
| 2 weeks | 2019 Jan. 31 | A-D | A-D | A-D |
| 4 weeks | 2019 Feb. 14 | A-D | A-D | A-D |
| 8 weeks | 2019 Mar. 14 | A-D | A-D | A-D |
| 12 weeks | 2019 Apr. 11 | A-D | A-E | A-D |

Approximate relative retention time (RRT) for the known impurities using current RP-HPLC method are provided in Table 9 above.
Study Results—Initial Films Fourteen formulations were prepared with different stabilizer compositions and cast pH. Viscosity was measured prior to coating. Although viscosity is generally higher in casts at pH close to 4, all formulations can easily be coated and form homogenous films. Absence of reflective spots under polarized microscope indicated absence of crystals in freshly made films.

Formation of impurity F (RRT 0.89) was detected in most film formulations without ascorbic acid (#79, #81 and #87). It is suspected that the sulfonation reaction is retarded by the presence of ascorbic acid.
Study Results—after 2- and 4-Week Storage
Physical Changes All formulations passed the appearance and pliability specification according to the limits listed in Table 7.
Chemical Changes Under cold storage conditions (+5° C.), no impurity content was found in most formulations after 4-week storage. The only formulation that contained impurity was #92, in which impurity F was detected. Although the formation of impurity F is related to the sodium bisulfite concentration, the formulations with higher molar ratio of sodium bisulfite than #92 did not contain impurity F. A speculation is that the detected peak was a false positive due to errors in analytical method.

Under ambient conditions (room temperature), no impurity content was found after 4-week storage in formulations containing low concentration of stabilizers. Impurities at RRT 2.32 and 3.16 were formed in formulations with ascorbic acid at a molar ratio of ≥0.025 to adrenaline, i.e. #80, #84, #85 and #86. Formation of impurity F was found in #87 and #88.

Figure 6:
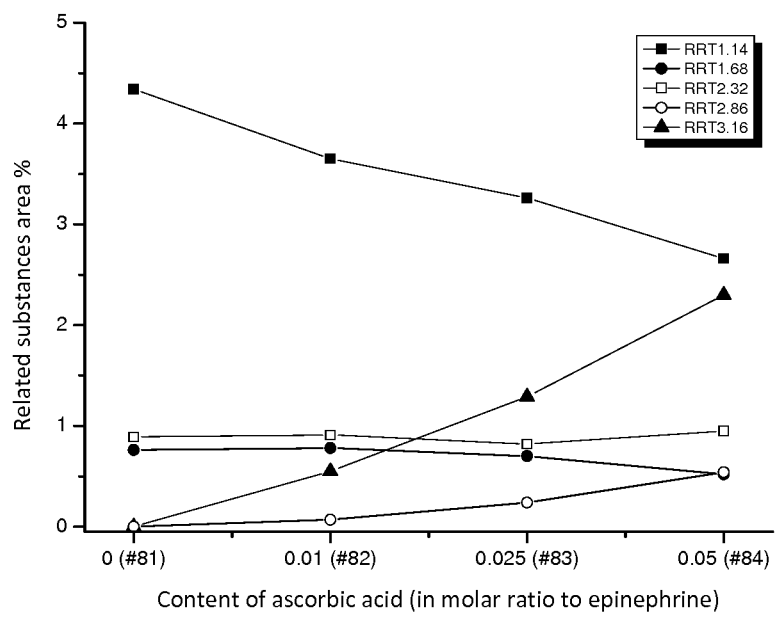
FIG. 6 shows the relative substance area (%) for impurities having an RRT of 1.14, 1.68, 2.32, 2.86 and 3.16 for formulations #81, #82, #83 and #84 with increasing molar ratio of ascorbic acid to molar ratio of adrenaline. Films were stored for 4 weeks at 40° C./75% R.H.

Impurity content was higher in all formulations after 4-week storage at 40° C./75% R.H. The amount of impurity at RRT 3.16 was observed to increase with increased content of ascorbic acid in formulation #81-84 (see FIG. 6). The impurity at RRT 2.86 increased slightly with increased content of ascorbic acid in formulation #81-84 (FIG. 6). However, with increasing content of ascorbic acid, the formation of impurity C (RRT 1.14) and impurity at RRT 1.68 was hindered. Considering both effects, it is anticipated that low content of ascorbic acid in combination with sodium metabisulfite should have an effect in reducing the total impurity content.

Figure 7:
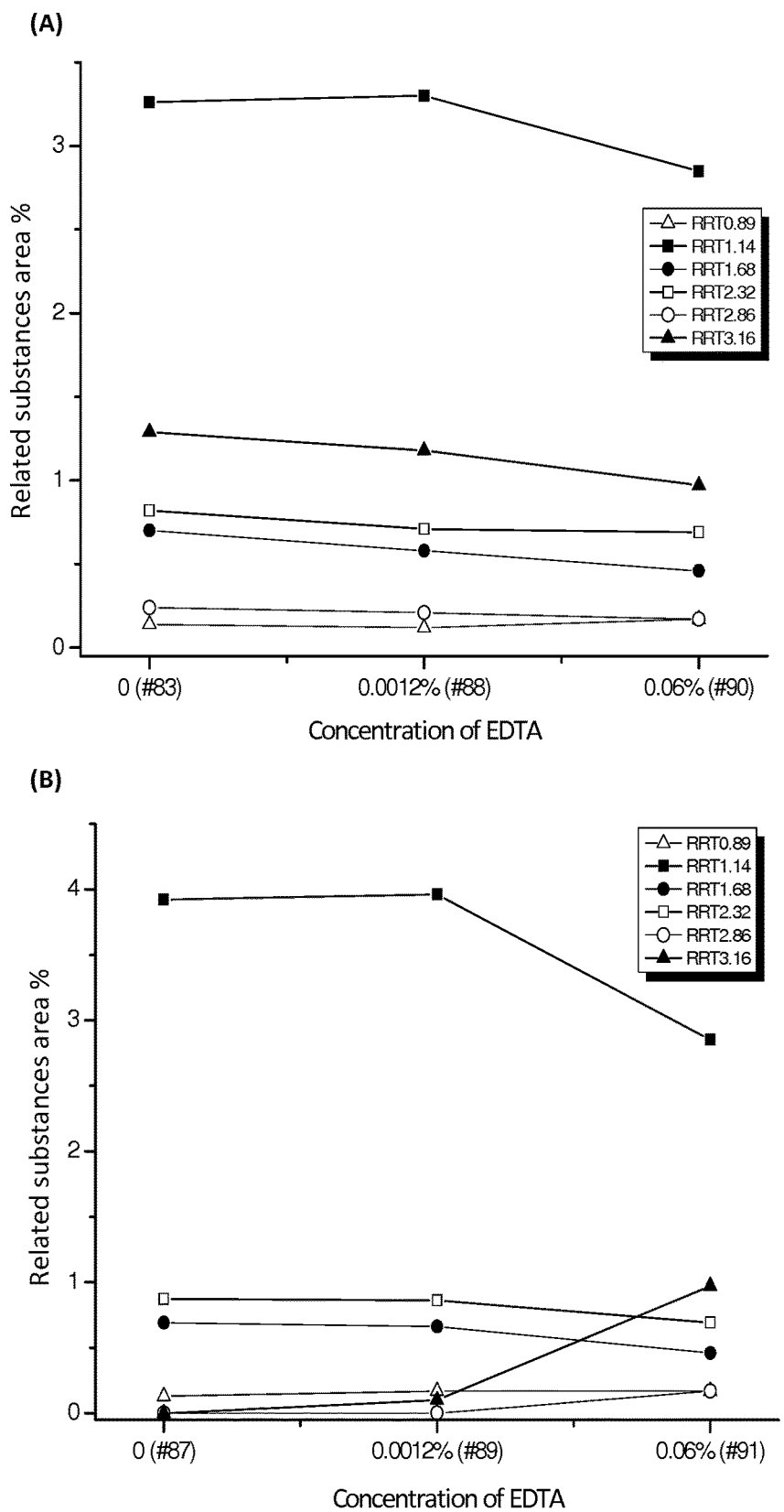
FIG. 7 shows (A) the relative substance area (%) for impurities having an RRT of 0.89, 1.14, 1.68, 2.32, 2.86 and 3.16 for formulations #83, #88 and #90 with increasing content of EDTA after 4-week storage at 40° C./75% R.H., and (B) the relative substance area (%) for impurities having an RRT of 1.14, 1.68, 2.32, 2.86 and 3.16 for formulations #87, #89 and #91 with increasing content of EDTA after 4-week storage at 40° C./75% R.H.

As shown in FIGS. 7 A&B, the EDTA content at 0.06% in the cast is observed to retard formation of impurity C (RRT 1.14).

No clear trend can be observed on the stability of the formulations with increasing sodium metabisulfite content.
Study Results—after 8-Week Storage
Physical Changes All formulations passed the appearance and pliability specification according to the limits listed in Table 7.
Chemical Changes Under cold storage conditions (+5° C.), no impurity content was found in all formulations after 8-week storage.

Under ambient conditions (room temperature), a low content of impurity F (between 0.05%-0.2%) was found in some of the formulations, i.e. #79, #80, #81, #82, #88, #89 and #92.

Figure 8:
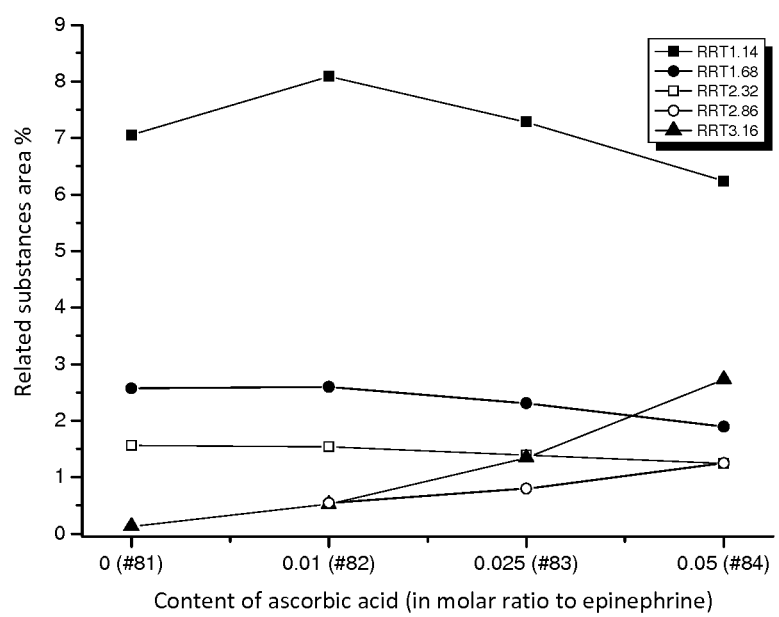
FIG. 8 shows the relative substance area (%) for impurities having an RRT of 1.14, 1.68, 2.32, 2.86 and 3.16 for formulations #81, #82, #83 and #84 with increasing molar ratio of ascorbic acid to molar ratio of adrenaline. Films were stored for 8 weeks at 40° C./75% R.H.
Figure 9:
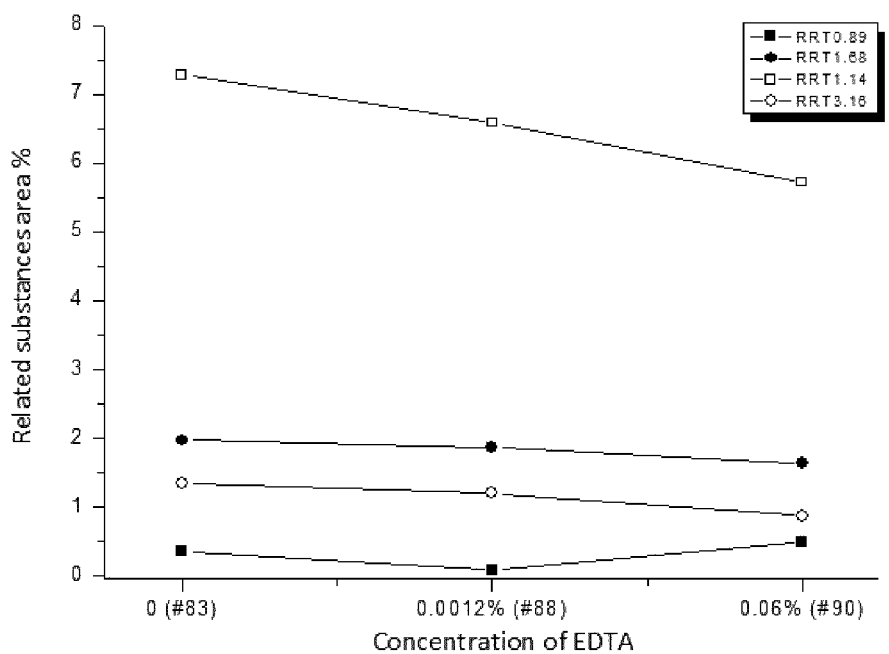
FIG. 9 shows (A) the relative substance area (%) for impurities having an RRT of 0.89, 1.14, 1.68 and 3.16 for formulations #83, #88 and #90 with increasing content of EDTA after 8-week storage at 40° C./75% R.H., and (B) the relative substance area (%) for impurities having an RRT of 1.14, 1.68 and 3.16 for formulations #87, #89 and #91 with increasing content of EDTA after 8-week storage at 40° C./75% R.H.
Figure 9:
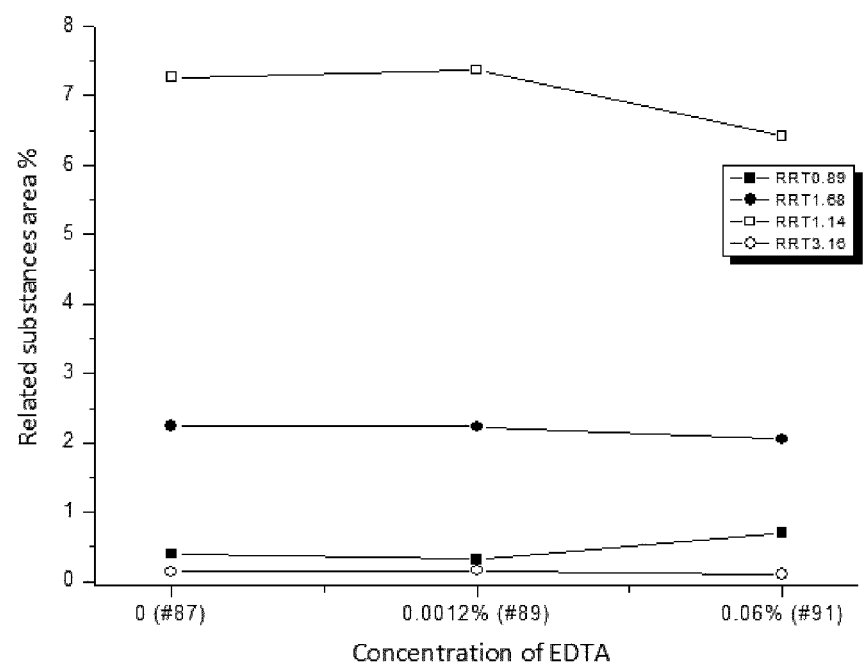

Under accelerated conditions (40° C./75% R.H.), the same trends were observed as in the results after 4-week storage. The content of impurities at RRT 2.86 and 3.16 increased with an increasing amount of ascorbic acid in formulation #81-84 (FIG. 8). EDTA content at 0.06% in cast retards the formation of impurity C (RRT 1.14) (FIGS. 9 A&B).
Study Results—after 12-Week Storage
Physical Changes Formulations stored under cold storage and ambient conditions passed the appearance and pliability specification according to the limits listed in Table 7. No crystal has been found in all formulations after 12-week storage under cold storage and ambient conditions.

At 40° C./75% R.H., crystallization has been noticed in the 3 mg adrenaline formulations (#79-#91) after 12-week storage. However, no crystals were found in the 1 mg formulation (#92), indicating crystallization may be dose-dependent.
Chemical Changes Under cold storage conditions (+5° C.), no impurity content was found in any of the formulations after 12-week storage.

Under ambient conditions (room temperature), an unknown impurity (RRT 2.32) was found at low content (between 0.05%-0.14%) in most of the formulation. Another unknown impurity (RRT 3.16) was found in formulations with relatively higher concentration of ascorbic acid, i.e. #80, #84, #86 #88 and #90.

Figure 10:
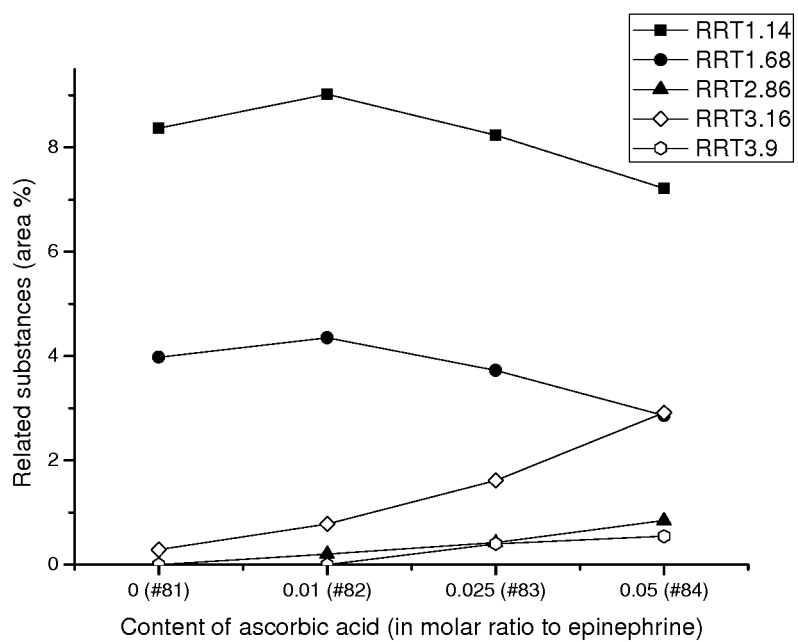
FIG. 10 shows the relative substance area (%) for impurities having an RRT of 1.14, 1.68, 2.86, 3.16 and 3.9 with increasing molar ratio of ascorbic acid to molar ratio of adrenaline in the formulations #81, #82, #83 and #84. Films were stored for 12 weeks at 40° C./75% R.H.
Figure 11:
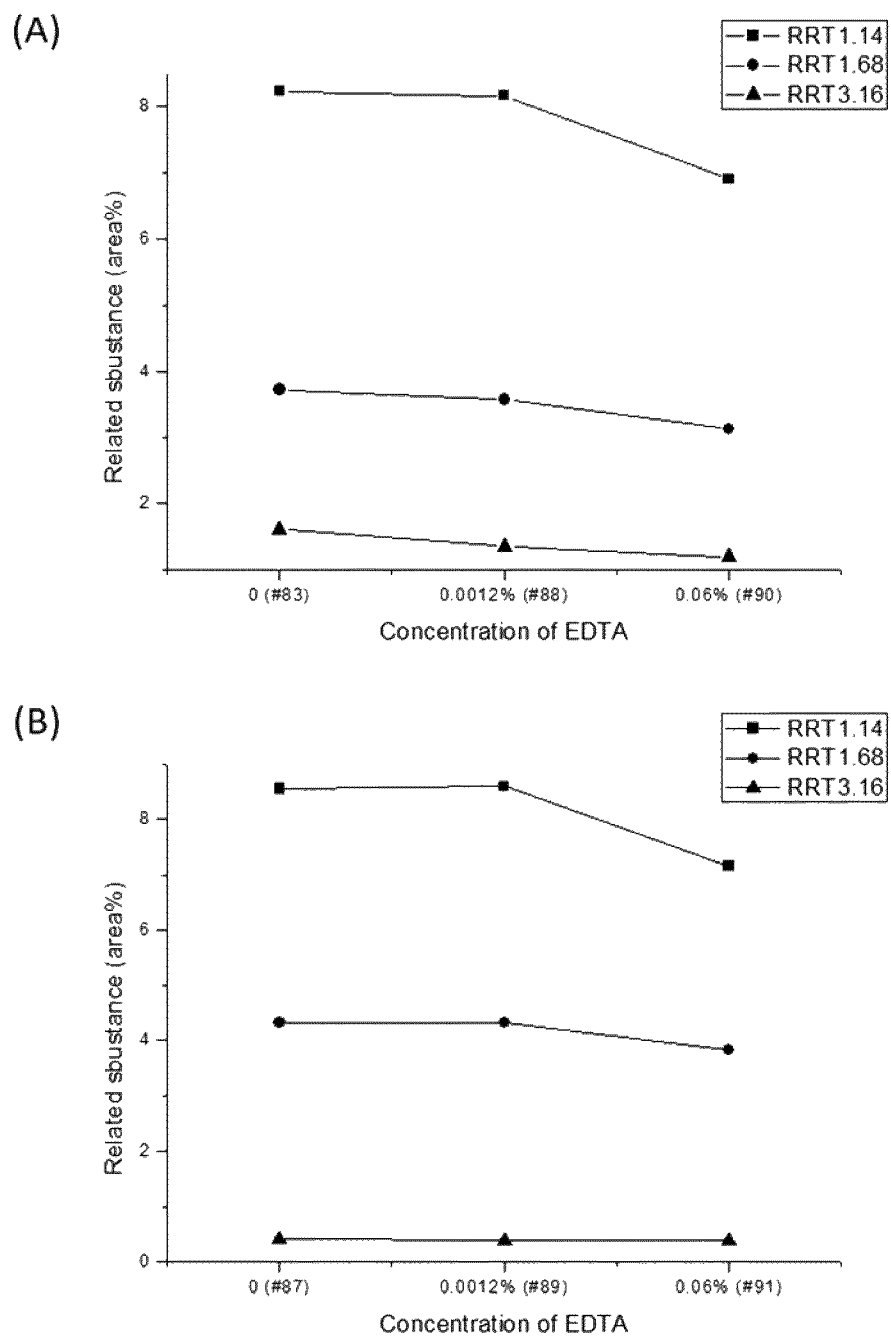
FIG. 11 shows (A) the relative substance area (%) for impurities having an RRT of 1.14, 1.68 and 3.16 for formulations #83, #88 and #90 with increasing content of EDTA after 12-week storage at 40° C./75% R.H., and (B) the relative substance area (%) for impurities having an RRT of 1.14, 1.68 and 3.16 for formulations #87, #89 and #91 with increasing content of EDTA after 12 weeks of storage at 40° C./75% R.H.

Under accelerated conditions (40° C./75% R.H.), some new unknown impurities at RRT 1.2, 2.06 and 3.9 appeared in some formulations. The content of impurities at RRT 2.86, 3.16 and 3.9 increased with the increasing content of ascorbic acid in formulations #81-84 (see FIG. 10). The formation of impurity C (RRT 1.14) and unknown impurity at RRT 1.68 were slightly hindered with a higher content of ascorbic acid in the formulations. Formulations with EDTA content at 0.06% in cast showed slightly lower content of impurity C (RRT 1.14) and unknown impurities at RRT 1.68 and 3.16 (see FIGS. 11 A&B) than the formulations with 0.0012% EDTA.

Example 6: Further Optimization of Film Stability

In Example 4, it was noted that ascorbic acid and sodium bisulfite displayed a stabilizing effect in the adrenaline buccal formulations. However, some impurities were observed to increase in concentration at higher ascorbic acid concentrations (although were still present at a relatively low, i.e. an acceptable, amount). Further, it was noted in Example 5 that decreasing the total amount of antioxidants present in the film may lead to a reduced amount of these particular impurities, but also to an increased level of impurities resulting from oxidation of adrenaline. To optimize the film formulations, it seems that a balance between the antioxidation effect and related impurity formation should be reached for the mixture of stabilizers employed, i.e. ascorbic acid, sodium metabisulfite and EDTA.

In this example study, the physical and chemical stability of eighteen 3 mg adrenaline buccal formulations under cold storage conditions (5° C.), long-term storage conditions (25° C./60% R.H.), intermediate storage conditions (30° C./65% R.H.) and accelerated storage conditions (40° C./75% R.H.) were further optimized. Study design was influenced by the results of Examples 4 and 5. A summary of the effects of each of the three stabilizer components that can be established from Examples 4 and 5 is as follows:

Sodium metabisulfite: The formulations with the lowest total impurity content after 4-week storage under ambient and accelerated conditions were the ones containing no or 0.05 sodium bisulfite in molar ratio to epinephrine in Example 4, i.e. #54 and #58. Therefore, the content of bisulfite in the formulation in this study contains ≤0.05 in molar ratio to adrenaline.

Ascorbic acid: Due to the pro-oxidant effect of ascorbic acid at higher concentrations, it is anticipated that a lower concentration of ascorbic acid could result in a reduced amount of impurities having an RRT of 2.86 and 3.16 (and thus a reduction in the total content of impurities). A lower concentration of ascorbic acid (that would likely result overall in a reduced antioxidative effect on adrenaline) should be mitigated by inclusion of other stabilizing agents.

EDTA: An EDTA content of 0.06% in the cast showed a positive effect on retarding formation of impurity C (RRT 1.14) in Example 5. A higher concentration of EDTA in cast, i.e. 0.12%, will thus also be explored in this study.

Three formulations with lowest total impurity content under accelerated conditions in Examples 4 and 5 were selected as the base formulations for this study, i.e. formulations #54, #58 and #81. Based on these formulations, variant concentration of ascorbic acid and EDTA was investigated. Eighteen buccal formulations containing a combination of stabilizers at pH 3.9±0.2 were prepared. Compositions of the studied formulations are given in Table 12.

TABLE 12

Compositions of the studied formulations.

| Batch # | #100 | #101 | #102 | #103 | #104 | Function |
|---|---|---|---|---|---|---|
| Adrenaline | 3 mg | 3 mg | 3 mg | 3 mg | 3 mg | API |
| Ascorbic acid | — | — | — | 0.003 mg | 0.003 mg | Stabilizer/Anitoxidant |
| Sodium metabisulfite | 0.004 mg | 0.004 mg | 0.004 mg | 0.004 mg | 0.004 mg | Stabilizer/Anitoxidant |
| EDTA | — | 0.078 mg | 0.156 mg | — | 0.078 mg | Stabilizer/Anitoxidant |
| Sodium alginate | c. 13 mg | c. 13 mg | c. 13 mg | c. 13 mg | c. 13 mg | Film forming agent |
| Sorbitol | c. 3 mg | c. 3 mg | c. 3 mg | c. 3 mg | c. 3 mg | Plasticizer |
| Glycerol | c. 3 mg | c. 3 mg | c. 3 mg | c. 3 mg | c. 3 mg | Plasticizer |
| Water | c. 3 mg | c. 3 mg | c. 3 mg | c. 3 mg | c. 3 mg | Solvent |

| Batch # | #105 | #106 | #107 | #108 | #109 | Function |
|---|---|---|---|---|---|---|
| Adrenaline | 3 mg | 3 mg | 3 mg | 3 mg | 3 mg | API |
| Ascorbic acid | 0.003 mg | — | — | — | 0.003 mg | Stabilizer/Anitoxidant |
| Sodium metabisulfite | 0.004 mg | 0.05 mg | 0.05 mg | 0.05 mg | 0.05 mg | Stabilizer/Anitoxidant |
| EDTA | 0.156 mg | — | 0.078 mg | 0.156 mg | — | Stabilizer/Anitoxidant |
| Sodium alginate | c. 13 mg | c. 13 mg | c. 13 mg | c. 13 mg | c. 13 mg | Film forming agent |
| Sorbitol | c. 3 mg | c. 3 mg | c. 3 mg | c. 3 mg | c. 3 mg | Plasticizer |
| Glycerol | c. 3 mg | c. 3 mg | c. 3 mg | c. 3 mg | c. 3 mg | Plasticizer |
| Water | c. 3 mg | c. 3 mg | c. 3 mg | c. 3 mg | c. 3 mg | Solvent |

| Batch # | #110 | #111 | #112 | #113 | #114 | Function |
|---|---|---|---|---|---|---|
| Adrenaline | 3 mg | 3 mg | 3 mg | 3 mg | 3 mg | API |
| Ascorbic acid | 0.003 mg | 0.003 mg | 0.03 mg | 0.03 mg | 0.03 mg | Stabilizer/Anitoxidant |
| Sodium metabisulfite | 0.05 mg | 0.05 mg | 0.05 mg | 0.05 mg | 0.05 mg | Stabilizer/Anitoxidant |
| EDTA | 0.078 mg | 0.156 mg | — | 0.078 mg | 0.156 mg | Stabilizer/Anitoxidant |
| Sodium alginate | c. 13 mg | c. 13 mg | c. 13 mg | c. 13 mg | c. 13 mg | Film forming agent |
| Sorbitol | c. 3 mg | c. 3 mg | c. 3 mg | c. 3 mg | c. 3 mg | Plasticizer |
| Glycerol | c. 3 mg | c. 3 mg | c. 3 mg | c. 3 mg | c. 3 mg | Plasticizer |
| Water | c. 3 mg | c. 3 mg | c. 3 mg | c. 3 mg | c. 3 mg | Solvent |

| Batch # | #115 | #116 | #117 | Function |
|---|---|---|---|---|
| Epinephrine | 3 mg | 3 mg | 3 mg | API |
| Ascorbic acid | 0.15 mg | 0.15 mg | 0.15 mg | Stabilizer/Antioxidant |
| Sodium metabisulfite | 0.05 mg | 0.05 mg | 0.05 mg | Stabilizer/Antioxidant |
| EDTA | — | 0.078 mg | 0.156 mg | Stabilizer/Antioxidant |
| Sodium alginate | c. 13 mg | c. 13 mg | c. 13 mg | Film forming agent |
| Sorbitol | c. 3 mg | c. 3 mg | c. 3 mg | Plasticizer |
| Glycerol | c. 3 mg | c. 3 mg | c. 3 mg | Plasticizer |
| Water | c. 3 mg | c. 3 mg | c. 3 mg | Solvent |

The films were packed in Alu/PET pouches immediately after preparation. Films from batch #110 and batch #114 were also packed in Alu/PET pouches purged with $N_2$. All samples were protected from light and stored under cold storage conditions (5° C.), long-term storage conditions (25° C./60% R.H.), intermediate storage conditions (30° C./65% R.H.) and accelerated storage conditions (40° C./75% R.H.).

Analysis Schedule and Methods

The formulations were analyzed according to the stability program set out in Table 13. The stability of the adrenaline buccal film prototypes were followed for 8 weeks. The analytical methods and specification limits applied are as described above in Table 7.

TABLE 13

Stability program used in this study

| Time points | Date | 5° C. | 25° C./60% R.H. | 30° C./65% R.H. | 40° C./75% R.H. |
|---|---|---|---|---|---|
| Initial | 2019 Feb. 21 | A-E | A-E | A-E | A-E |
| 2 weeks | 2019 Mar. 7 | A-D | A-D | A-D | A-D |
| 4 weeks | 2019 Mar. 21 | A-D | A-D | A-D | A-D |
| 8 weeks | 2019 Apr. 17 | A-E | A-E | A-E | A-E |

The HPLC method used to evaluate samples was developed by Recipharm (Uppsala, Sweden) and differs from the method used to evaluate samples in Examples 4 and 5 above. This HPLC-RPC method is as follows:

An Agilent 100 series liquid chromatographic system was used consisting of a binary pump, degasser, autosampler, thermostatic column compartment and a diode array UV detector was used for analysis. The HPLC column was a YMC-Triart PFP (150×3.0 mm, 3 μm), YMC co. The filter membrane was from Membrane Solutions, MS® Nylon Syringe Filter diameter 30 mm, Pore size 0.45 μm. The Vortex-Mix was UK plug VWR.

Buffer solution A was prepared by dissolving 5.0 g of potassium dihydrogen phosphate and 2.6 g of sodium octane sulfonate monohydrate in 1000 mL water using a magnetic stirrer. It was necessary to stir for at least 10 minutes to achieve complete dissolution. The pH was then adjusted to 4.0 with o-phosphoric acid solution.

Stock solutions of adrenaline, impurities B, C, D, E, F, D, L-adrenochrome and excipients (E1, E2, E3, E4 and E5) were prepared at the concentration of 1 mg/mL. All impurities and excipients were dissolved in HCl 1 M/Buffer A/MeOH in the ratio 1/8/1 (v/v/v). The three solution must be added separately following the order HCl 1 M/Buffer A/MeOH. Adrenaline was prepared directly in sample diluent. The stock solutions were then diluted at the concentrations of 50, 5 and 0.5 μg/mL using sample diluent. A mix of all compounds was also prepared at the concentration about 50 μg/ml.

Each compound was injected separately and in the mixture solution. Retention time and relative retention time are measured and will be used for identification of API and the impurities. Resolution between peaks was be measured. Due to the low stability of D, L-adrenochrome, this impurity was prepared and immediately injected.

To prepare a test sample for 1 mg API dose/film, 2 test films were accurately weighed and then transferred in a 10 mL volumetric flask and 5 mL of Buffer A was added. The solution was then vortexed for 5 minutes and 1.0 mL of MeOH was added. Mixing was continued for 2 minutes. Buffer A was added to reach a final volume of 10 mL. The solution was filtered with a 0.45 μm filter. The first 3 mL was discarded and the next 1 mL was collected in an amber 1 mL vial.

To prepare a test sample for 3 mg API dose/film, 2 test films were accurately weighed and then transferred in a 30 mL volumetric flask and 18 mL of Buffer A was added. The solution was then vortexed for 5 minutes and 3 mL of MeOH was added. Mixing was continued for 2 minutes. Buffer A was added to reach a final volume of 30 mL. The solution was filtered with a 0.45 μm filter. The first 3 mL was discarded and the next 1 mL was collected in an amber 1 mL vial.

HPLC was performed with the following settings: flow rate=0.8 mL/min; injection volume=5.0 μL; run time=30 min.; detection wavelength=210±4 nm; column temperature=50° C.; injection temperature=25° C.; needle wash solvent=solvent mix of buffer A (pH 4.0):MeOH of 9:1 (v/v), 1 time; dilution solvent=90% mobile phase A:10% mobile phase B (v/v).

The column was equilibrated and then the analysis was performed as a gradient run, as follows (Mobile Phase A=buffer solution A; Mobile Phase B=MeOH):

| Time (min) | % mobile phase A | % mobile phase B |
|---|---|---|
| 0 | 100 | 0 |
| 2 | 100 | 0 |
| 16 | 45 | 55 |
| 20 | 45 | 55 |
| 21 | 100 | 0 |
| 30 | 100 | 0 |

After data collection, the standard samples were used to produce a calibration curve, against which the sample data could then be measured to determine the concentration of adrenaline and impurities in the samples.

Using this method, the approximate relative retention time (RRT) for identified impurities are set out in Table 14 below.

TABLE 14

Relative retention time for the specified impurities. RRT calculated versus the retention time of the main peak.

| Specific impurities | RRT |
|---|---|
| Impurity B (Norepinephrine) | 0.73 |
| Impurity C (Adrenalone) | 1.17 |
| Impurity D | 1.66 |
| Impurity E | 1.78 |
| Impurity F (Epinephrine Sulfonic Acid) | 0.15 |
| D, L-Adrenochrome | 0.42 |

Study Results—Initial Films

Eighteen formulations were prepared with different stabilizer compositions at pH 3.9±0.2. Viscosity was measured prior to coating. All formulations could easily be coated and formed homogenous films. Absence of reflective spots under polarized microscope indicated absence of crystals in freshly made films. Except for batch #115, no impurities was found in the studied formulations initially. A high content of unknown impurity (RRT 1.04) was found in batch #115, which was probably caused by the unexpected degradation of adrenaline during the sample preparation.

Study Results—after 2- and 4-Week Storage

Physical Changes

All formulations passed the appearance and pliability specification according to the limits listed in Table 7.

Chemical Changes

Under cold storage conditions (+5° C.) and long-term storage conditions (25° C./60% R.H.), low content of total impurity (<0.5%) was found in most of the formulations. Higher content of total impurity was observed in formulations #112 and #115, which was mainly attributed to the impurity at RRT 1.04. It is suspected that the detected peak in #112 was a false positive due to errors in analytical method.

After 4-weeks storage at intermediate storage conditions (30° C./65% R.H.), low content of total impurity (≤1%) can be found in some of the formulations, i.e. #110, #114, #107, #108, #111. However, under accelerated storage conditions (40° C./75% R.H.), almost all the studied formulation (except for #113) showed higher content of total impurity (>3.5%). The content of total impurity for #113 was 3.4% at 40° C., which is still within an acceptable limit.

Formulations with sodium metabisulfite content at 0.05 (in molar ratio to epinephrine) showed a better stabilizing effect than at 0.025. A combination of higher amounts of sodium metabisulfite and lower concentration of ascorbic acid (≤0.01 in molar ratio to epinephrine) resulted in a lower total impurity content. The impurity at RRT 0.77 can be observed in film formulations with an ascorbic acid content>0.01 in molar ratio to epinephrine.

The addition of EDTA showed a positive effect on retarding formation of impurity at RRT 1.04. According to the results for #110 and #110$N_2$, #114 and #114$N_2$, the impact of the storage atmosphere ($N_2$ or air) on the chemical stability was not significant after 4 weeks of storage.

Study Results—after 8-Week Storage

Physical Changes

Formulations stored at cold storage conditions (5° C.), long-term conditions (25° C./60% R.H.) and intermediate conditions (30° C./65% R.H.) passed the appearance and pliability specification according to the limits listed in Table 7. Some crystals were observed in some formulations after storage at 25° C./60% R.H. or 30° C./65% R.H.

After 8-week storage at 40° C./75% R.H. all formulations became opaque and crystallization was observed under the polarized microscope.

Chemical Changes

No impurity was detected in the studied formulations except for in batch #115 after 8-week storage at cold storage conditions (5° C.). As the impurities at RRT 1.04 and 1.07 were detected initially, it is suspected these impurities are a result of contamination during film preparation.

At ambient conditions (25° C./60% R.H.), a low content of total impurity (<1%) was observed for most formulations after 8-week storage. No impurity was detected in formulations #105, #107, #113 and #114.

Figure 12:
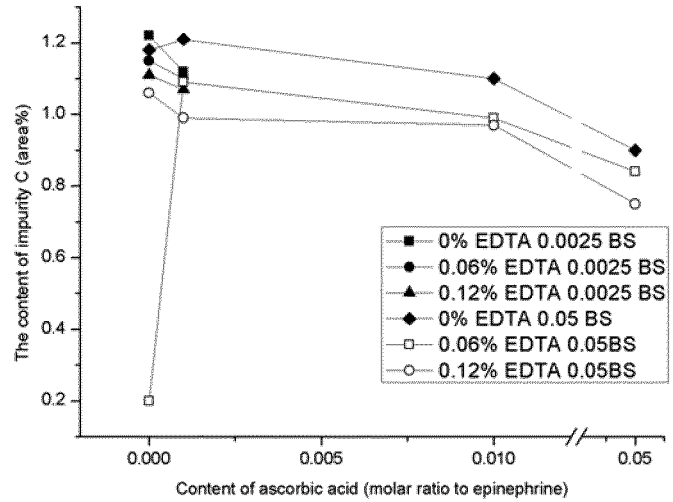
FIG. 12 shows (A) the content of impurity C (RRT 1.15) with increasing content of ascorbic acid (in molar ratio to epinephrine); note that there is a break in x-axis between 0.01 to 0.05, and (B) the content of impurity C (RRT 1.15) with increasing concentration of EDTA (%). AA=ascorbic acid; BS=sodium metabisulfite.
Figure 12:
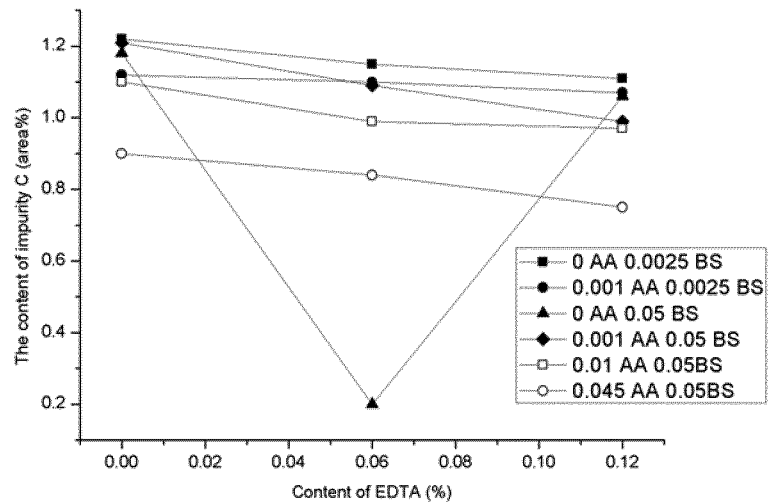

The total impurity content was <2% in all formulations except for batch #115 stored at intermediate conditions (30° C./65% R.H.). Impurity C (RRT 1.15) and an unknown impurity at RRT 1.56 were the major impurities found in the formulations. The content of both these impurities doubled since the previous time point (4 weeks). Increasing the content of ascorbic acid (from 0 to 0.05 in molar ratio to epinephrine) and EDTA (from 0 to 0.12%) can slightly retard the formation of impurity C (RRT 1.15) (see FIGS. 12 A&B).

Figure 13:
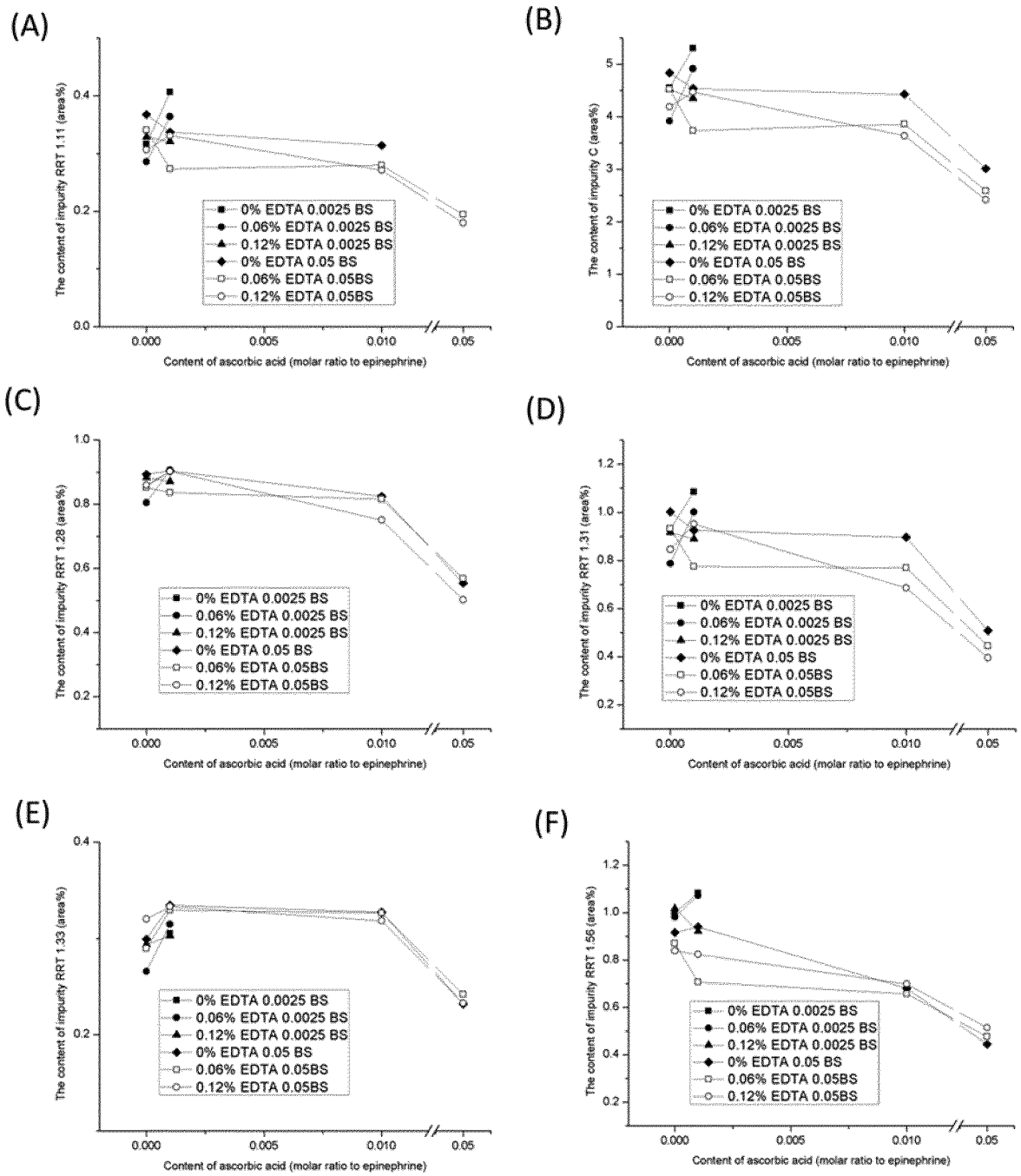
FIG. 13 shows (A) the content of impurity at RRT 1.11, (B) impurity C (RRT 1.15), (C) impurity at RRT 1.28, (D) impurity at RRT 1.31, (E) impurity at RRT 1.33, and (F) impurity at RRT 1.56 with increasing content of ascorbic acid (in molar ratio to epinephrine); note that there is a break in x-axis between 0.01 to 0.05. AA=ascorbic acid; BS=sodium metabisulfite.
Figure 14:
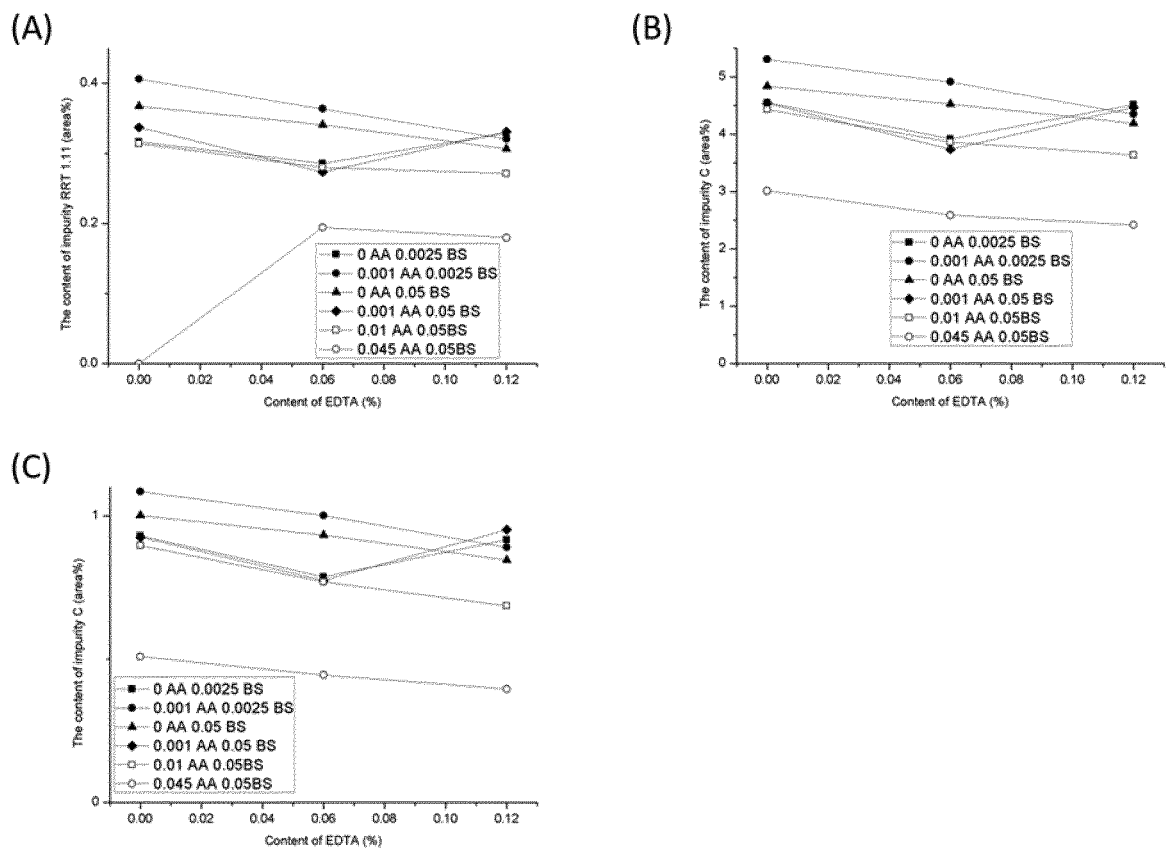
FIG. 14 shows (A) the content of impurity at RRT 1.11, (B) impurity C (RRT 1.15), and (C) impurity at RRT 1.31 with increasing concentration of EDTA (%). AA=ascorbic acid; BS=sodium metabisulfite.

A greater number of impurities and higher total impurity concentration was observed in the formulations stored at accelerated conditions (40° C./75% R.H.). Higher ascorbic acid content in the film suppressed the growth of all impurities having an RRT of 1.11, 1.15, 1.28, 1.31, 1.33 and 1.56 (FIG. 13 A-F). However, impurities at RRT 0.72 and 0.77 were found in formulations with ascorbic acid at 0.05 in molar ratio to adrenaline, i.e. #115, #116 and #117. A lower content of impurity C (RRT 1.15) and unknown impurities RRT 1.11 and 1.31 were found in the formulations with higher concentration of EDTA 0.12% than that in those without EDTA (see FIG. 14 A-C).

CONCLUSIONS

In conclusion, it has been observed that the presence of ascorbic acid, sodium metabisulfite and EDTA can all improve the stability of adrenaline-containing buccal film formulations. However, for the most optimal films, a balance should be struck between preventing adrenaline oxidation and suppressing formation of impurities which result from the stabilizing additives themselves. In particular, it seems that limiting the concentration of ascorbic acid to 0.01 or less (in a molar ratio to adrenaline) in combination with higher concentrations of sodium metabisulfite (0.05 or greater, in a molar ratio to adrenaline) and EDTA (0.06 wt % or greater; or 0.03 or greater, in a molar ratio to adrenaline) is particularly beneficial.

REFERENCES

[1] McLean-Tooke A P, Bethune C A, Fay A C, Spickett G P. Adrenaline in the treatment of anaphylaxis: what is the evidence? BMJ, 2003, 327 (7427): 1332-1335.
[2] Upfal, J. The Australian Drug Guide. 2007, 7$^{th}$ Ed., pub. Black Inc.
[3] Simons F. Epinephrine absorption in children with a history of anaphylaxis. *J Clin Immunol*, 1998, 101: 33-37.
[4] Tuleu, C. et al. Short term stability of pH-adjusted lidocaine-adrenaline epidural solution used for emergency caesarean section. *International Journal of obstetric anesthesia*, 17.2, 118-122.
[5] Prachayasittikul, V.; Isarankura-Na-Ayudhya, C.; Tantimongcolwat, T.; Nantasenamat, C.; Galla, H. J. EDTA-induced Membrane Fluidization and Destabilization: Biophysical Studies on Artificial Lipid Membranes. *Acta biochimica et biophysica Sinica*, 2007, 39(11), 901-913.
[6] Managaro and Wertz, "The Effects of Permeabilizers on the In Vitro Penetration of Propranolol Through Porcine Buccal Epithelium", *Mil Med*, 1996, 161 (11), 669-672.
[7] Date, A. A.; Desai, N.; Dixit, R.; Nagarsenker, M. Self-nanoemulsifying Drug Delivery Systems: Formulation Insights, Applications and Advances. *Nanomedicine*, 2010, 5(10), 1595-1616.
[8] Pouton, C. W. Formation of poorly water-soluble drugs for oral administration: Physicochemical and physiological issues and the lipid formulation classification system. *European Journal of Pharmaceutical Sciences*, 2006, 29(3-4), 278-287.
[9] European Pharmacopoeia Commission & European Directorate for the Quality of Medicines & Healthcare. *European Pharmacopoeia*, 2013, Council of Europe, Vol. 1, 1490-1492.

The invention claimed is:

1. A film suitable for administration to an oral cavity comprising:
  (i) an alginate salt of a monovalent cation or a mixture of alginate salts containing at least one alginate salt of a monovalent cation, wherein said alginate salt is a sodium alginate or a potassium alginate;
  (ii) an active pharmaceutical ingredient (API) which is adrenaline or a pharmaceutically acceptable salt thereof;
  (iii) an antioxidant selected from the group consisting of sodium metabisulfite, sodium bisulfite, and combinations thereof; and
  (iv) at least one plasticizer which is selected from sorbitol, glycerol, or both sorbitol and glycerol, further wherein the alginate salt of a monovalent cation (a) comprises from 25 to 35% by weight of β-D-mannuronate and from 65 to 75% by weight of α-L-guluronate, and (b) has a weight average molecular weight of from 30,000 g/mol to 90,000 g/mol, wherein the film is stable for 83 days at room temperature.

2. The film according to claim 1, wherein the API is (−)-adrenaline or a pharmaceutically acceptable salt thereof.

3. The film according to claim 1, wherein the API is the tartrate salt of adrenaline.

4. The film according to claim 1, wherein the alginate salt of a monovalent cation is a sodium alginate.

5. The film according to claim 1, wherein the film comprises from 25% to 99% by weight of the alginate salt of a monovalent cation or the mixture of alginate salts containing at least one alginate salt of a monovalent cation, from 0% to 20% by weight of water, and from 0.001% to 75% by weight of the API.

6. The film according to claim 1, wherein the film comprises from 29% to 93% by weight of the alginate salt of a monovalent cation or the mixture of alginate salts containing at least one alginate salt of a monovalent cation, from 5% to 15% by weight of water, and from 0.15% to 50% by weight of the API.

7. The film according to claim 1, wherein the film comprises from 0.01 to 10% by weight of the antioxidant.

8. The film according to claim 1, wherein the film comprises sodium metabisulfite or sodium bisulfite and at least one further antioxidant.

9. The film according to claim 1, wherein the ratio of total antioxidants present in the film to total API present in the film, by weight, is from 0.01:1 to 10:1.

10. The film according to claim 8, wherein the film comprises (i) ascorbic acid and (ii) sodium bisulfite or sodium metabisulfite.

11. The film according to claim 1, wherein the film further comprises a basifying agent.

12. The film according to claim 1, wherein the film comprises up to 40% by weight of sorbitol, and up to 40% by weight of glycerol.

13. A method of treating anaphylaxis, superficial bleeding, or cardiac arrest in a human patient, wherein said method comprises administration of at least one film according to claim 1 to said human patient.

14. The method of claim 13, wherein the film is administered to the oral cavity of the human patient.

15. A method of manufacturing a film according to claim 1, said method comprising:
  (a) either:
    (i) mixing the API in water, or in a solution comprising water and at least one antioxidant selected from the group consisting of sodium metabisulfite, sodium bisulfite, and combinations thereof;
    (ii) mixing one or more excipients into the solution obtained; and
    (iii) adding the alginate salt of monovalent cation to result in the formation of a cast;
  or alternatively:
    (iv) mixing one or more excipients in water;
    (v) separately, dissolving the API in water, or an aqueous solution containing at least one antioxidant selected from the group consisting of sodium metabisulfite, sodium bisulfite, and combinations thereof;
    (vi) mixing the solution obtained in (iv) with the alginate salt of monovalent cation; and
    adding the solution obtained in (v) to the solution obtained in (vi) to result in the formation of a cast;
  (b) leaving the cast to de-aerate;
  (c) pouring the cast onto a surface and spreading the cast out to the desired thickness; and
  (d) drying the cast layer until the residual water content of the film is from 0 to 20% by weight and a solid film is formed.

16. The method of claim 15, wherein after the cast is poured onto a surface, it is first spread out to a thickness of about 2 mm by means of an applicator with a slit height of about 2 mm, and is then subsequently spread out to a thickness of about 1 mm by means of an applicator with a slit height of about 1 mm.

17. The film according to claim 8, wherein the film comprises citric acid and sodium metabisulfite.

18. The film according to claim 1, wherein the film comprises both sorbitol and glycerol.

19. The film according to claim 1, wherein the film comprises sorbitol, glycerol, sodium metabisulfite and citric acid.

20. The film according to claim 6, wherein the film comprises from 0.01% to 10% by weight of each antioxidant present and from 3% to 25% by weight of each plasticizer present.

21. The method of claim 13, wherein the method is a method of treating anaphylaxis.

22. The film of claim 1, wherein the ratio of total antioxidants present in the film to total API present in the film, by weight, is from 0.25:1 to 10:1.

23. The film of claim 1, wherein the film comprises sodium metabisulfite or sodium bisulfite, and wherein said sodium metabisulfite or said sodium bisulfite is in a molar amount of from 0.001 to 1.0 per mole of the API present in the film.

24. The film according to claim 3, wherein the API is the tartrate salt of (−)-adrenaline.

25. The film according to claim 9, wherein the ratio of total antioxidants present in the film to total API present in the film, by weight, is from 0.5:1 to 10:1.

26. The film according to claim 11, wherein the basifying agent is aqueous sodium hydroxide.

* * * * *